(12) United States Patent
Toner et al.

(10) Patent No.: US 6,759,245 B1
(45) Date of Patent: Jul. 6, 2004

(54) CELL CULTURE SYSTEMS AND METHODS FOR ORGAN ASSIST DEVICES

(75) Inventors: Mehmet Toner, Wellesley, MA (US); Arno W. Tilles, Cambridge, MA (US); Ulysses J. Balis, Peabody, MA (US); Martin L. Yarmush, Newton, MA (US); Maury D. Cosman, Woburn, MA (US); Paul A. Dimilla, Dover, MA (US)

(73) Assignees: The General Hospital Corporation, Boston, MA (US); Organogenesis Inc., Canton, MA (US)

( * ) Notice: Subject to any disclaimer, the term of this patent is extended or adjusted under 35 U.S.C. 154(b) by 0 days.

(21) Appl. No.: 09/599,891

(22) Filed: Jun. 21, 2000

Related U.S. Application Data

(60) Provisional application No. 60/140,125, filed on Jun. 21, 1999, provisional application No. 60/140,239, filed on Jun. 21, 1999, and provisional application No. 60/181,634, filed on Feb. 10, 2000.

(51) Int. Cl.$^7$ ............................................ C12N 5/00
(52) U.S. Cl. ................ 435/401; 435/284.1; 435/297.1; 435/297.2; 435/402; 435/395; 435/399
(58) Field of Search ................................ 435/401, 402, 435/395, 399, 284.1, 297.1, 297.2

(56) References Cited

U.S. PATENT DOCUMENTS

| | | | |
|---|---|---|---|
| 3,238,031 A | | 3/1966 | Nikoll ............................ 65/94 |
| 3,997,396 A | * | 12/1976 | Delente |
| 4,834,819 A | | 5/1989 | Todo et al. ................ 156/73.1 |
| 4,853,324 A | | 8/1989 | Viles et al. ..................... 435/2 |
| 4,937,196 A | | 6/1990 | Wrasidlo et al. |
| 5,026,649 A | * | 6/1991 | Lyman et al. |
| 5,162,225 A | * | 11/1992 | Sager et al. |
| 5,190,878 A | | 3/1993 | Wilhelm |
| 5,270,192 A | | 12/1993 | Li et al. ...................... 435/174 |
| 5,290,684 A | | 3/1994 | Kelly .......................... 435/29 |
| 5,416,022 A | | 5/1995 | Amiot |
| 5,459,069 A | | 10/1995 | Palsson et al. |
| 5,585,011 A | | 12/1996 | Saaski et al. ................... 216/2 |
| 5,602,026 A | * | 2/1997 | Dunn et al. |
| 5,605,835 A | | 2/1997 | Hu et al. ................. 435/297.2 |
| 5,622,857 A | | 4/1997 | Goffe ......................... 435/378 |
| 5,643,794 A | | 7/1997 | Liu et al. ................. 435/289.1 |
| 5,656,349 A | | 8/1997 | Gomi et al. ............... 428/65.3 |
| 5,658,797 A | | 8/1997 | Bader ....................... 435/284.1 |
| 5,660,728 A | | 8/1997 | Saaski et al. ............... 210/251 |
| 5,827,729 A | | 10/1998 | Naughton et al. ........ 435/297.2 |
| 6,228,607 B1 | | 5/2001 | Kersten et al. .............. 435/41 |

FOREIGN PATENT DOCUMENTS

| | | |
|---|---|---|
| EP | 0 363 262 A1 | 4/1990 |
| WO | WO 96/34087 | 10/1996 |
| WO | WO 00/56870 | 9/2000 |

OTHER PUBLICATIONS

Bader et al. "A Novel Bioreactor Design for In Vitro Reconstruction of In Vivo Liver Characteristics" Artif. Organs, 19(4):368–374, (1995).
Ellis et al. "Pilot–Controlled Trial of the Extracorporeal Liver Assist Device in Acute Liver Failure" Hepatology, 24(6):1446–1451, (1996).
Ledezma et al. "Numerical Model of Fluid Flow and Oxygen Transport in a Radial–Flow Microchannel Containing Hepatocytes" J. Biomechanical Engineering, 121:58–64, (1999).
Nyberg et al. "Extracorporeal Application of a Gel–Entrapment, Bioartificial Liver: Demonstration of Drug Metabolism and Other Biochemical Functions" Cell Transplantation, 2:441–452, (1993).
Rozga et al. "Development of a Hybrid Bioartificial Liver" Annals of Surgery, 217(5):502–511, (1993).
Sussman et al. "Extracorporeal Liver Support" J Clin Gastroenterol, 18(4):320–324, (1994).
Taguchi et al. "Development of a Bioartificial Liver with Sandwiched–Cultured Hepatocytes Between Two Collagen Gel Layers" Artificial Organs, 20(2):178–185, (1996).
Uchino et al. "A Hybrid Bioartificial Liver Composed of Multiplated Hepatocyte Monolayers" Asaio Transactions, 34(4):972–977, (1988).
Watanabe et al. "Clinical Experience With a Bioartificial Liver in the Treatment of Severe Liver Failure" Annals of Surgery, 225(5):484–494, (1997).
Yarmush et al. "Assessment of Artificial Liver Support Technology" Cell Transplantation, 1:323–341, (1992).
Smith MD, et al., "Development and characterization of a hybrid artificial liver bioreactor with integral membrane oxygenation," In: Bioartificial Liver Support Systems. The Critical Issues, Crepaldi G, Demetriou AA, Muraca M, Eds. 1997 Rome: CIC Edizioni Internazionali, pp. 27–35.
Watanabe et al. (1997) Clinical experience with a bioartificial liver in the treatment of severe liver failure. Annals of Surgery. vol. 225, No. 5, pp. 484–494.*

* cited by examiner

Primary Examiner—Leon B. Lankford, Jr.
(74) Attorney, Agent, or Firm—Fish & Richardson P.C.

(57) ABSTRACT

The invention features modular cell culturing devices including one or more flat-plate modules, and is based on the discovery that if the flows of liquid medium and oxygenated fluid are separated by a gas-permeable, liquid-impermeable membrane, and the cells are grown attached to the liquid side of the membrane, the device can be used to culture cells with transport of oxygen through the membrane (i.e., direct oxygenation), without regard for the flow rate of the liquid medium passing through the device. The new flow-through cell culturing devices can thus be used to culture cells, e.g., hepatocytes, with high levels of cell function in organ, e.g., liver, assist systems, for production of cells, for production of cell-derived products, such as, proteins or viruses, or for systems to treat biological liquids to remove toxins, such as, ammonia, or add cell-synthesized products, or both.

18 Claims, 26 Drawing Sheets

CELL CULTURE SYSTEMS AND METHODS FOR ORGAN ASSIST DEVICES

CROSS REFERENCE TO RELATED APPLICATIONS

This application claims priority from U.S. Provisional Application No. 60/140,125, filed Jun. 21, 1999, U.S. Provisional Application No. 60/140,239, filed on Jun. 21, 1999, and U.S. Provisional Application No. 60/181,634, filed on Feb. 10, 2000. The contents of these applications are incorporated herein by reference in their entirety.

FIELD OF THE INVENTION

The invention relates to systems and methods of culturing cells in organ assist devices.

BACKGROUND OF THE INVENTION

Over 43,000 Americans die each year from liver disease, making it the tenth leading disease-related cause of death in the U.S. When liver disease progresses to liver failure, the mortality is 80% unless a compatible donor organ is found. As with other organs, there is a critical shortage of donor livers. Over 12,000 patients are currently listed as transplant candidates, but fewer than half that number of donor livers become available each year. Treatment with a liver assist device (LAD) would decrease the mortality associated with liver failure by stabilizing patients so that they are suitable candidates for a transplant, by supporting them until a suitable donor liver becomes available, and/or by preventing deterioration to the point where a liver transplant is required. Improving the pre-operative health of these patients would also increase transplant success, thereby decreasing the frequency of retransplantation and easing the demand for donor organs.

In cases of sudden or hepatic failure, which often occurs as a result of viral infection or toxicity, treatment with a LAD would eliminate the need for a transplant by supporting these individuals until their own livers regenerate. Liver transplantation is currently the most expensive organ transplant procedure. Successful development of a LAD would consequently provide major benefits to the US in reduced deaths and health-care costs.

Extracorporeal devices for temporary liver support have been investigated since the 1960s. Two strategies have been explored in the development of liver assist devices: (1) non-biological devices based on hemoperfusion on sorbents, hemodialysis across selectively-permeable membranes, and plasma exchange (Malchesky, "Non-biological liver support: historic overview," Artif. Organs, 18:342–347, 1994); and (2) biological devices that incorporate cells or cellular components (Yarmush et al., "Assessment of artificial liver support technology," Cell Trans., 1:323–341, 1992).

Non-biological devices have shown only limited efficacy, confirming that synthetic materials cannot replace the range and level of complex metabolic functions normally performed by the liver. On the other hand, a biological LAD in which hepatocytes are seeded on the outer surface of hollow fibers and blood or plasma circulates through the lumen of these fibers was proposed almost 25 years ago by Wolf and colleagues (Wolf et al., "Bilirubin conjugation by an artificial liver composed of cultured cells and synthetic capillaries," Tran. Amer. Soc. Artif. Int. Organs, 21:16–23, 1975).

Current biological LAD designs use the inverse of this concept today. Modern designs are often based on providing critical liver function by supporting high-density hepatocyte suspensions in hollow fibers, with circulation of blood or plasma outside the fibers. In this design, intermittent extracorporeal liver function is to be provided until the patient recovers through liver regeneration or until a transplant becomes available. However, the hollow fiber design is limited by several factors, including: a) inadequate mass transport, particularly of oxygen, b) lack of understanding of hepatocyte function in an in vitro environment, c) randomized tissue architecture for support of cell viability and function, and d) constraints of void volume on the perfusion circuit for the device.

Hollow fibers have been chosen for LADs on the basis of ready availability rather than demonstrated ability to support hepatocyte function. Perfusion of high-density hepatocyte cultures in hollow fibers has shown a lack of convincing benefit due to, among other reasons, transport limitations that undermine their support of high-density cultures. Such limitations are particularly acute for oxygen, which is required for both basic metabolic function as well as for initial steps in detoxification. Perfusion of oxygenated plasma or medium through or around a network of hollow fibers fails to address this problem because these aqueous liquids are poor carriers for oxygen and the associated distances for transport are relatively large. Modifications to the core hollow-fiber design (e.g., the use of a woven network of three independent sets of capillaries providing integral oxygenation) significantly complicate fabrication and incompletely address underlying transport limitations. They also lack the ability to orient hepatocytes in a more organotypic laminar configuration.

SUMMARY OF THE INVENTION

The invention features modular cell culturing devices comprised of one or more flat-plate modules. The invention is based on the discovery that if the flows of liquid medium and an oxygenated fluid are separated by a gas-permeable, liquid-impermeable membrane, and the cells are grown cultured on the liquid side of the membrane, the device can be used to culture cells with transport of oxygen through the membrane to the cells with independent control of the flow rate of the liquid passing through the device. The new flow-through cell culturing devices can thus be used to culture cells, e.g., hepatocytes, with high levels of cell function in organ, e.g., liver, assist systems, for production of cells, for production of cell-derived products, such as proteins or viruses, or for systems to treat biological liquids to remove toxins, such as ammonia, add cell-synthesized products, or both.

In general, the invention features methods and devices for the culture of cells that provide direct oxygenation of cells through planar, gas-permeable membranes. When the apparatus is seeded with the appropriate cells and is incorporated into a device, the device can be used to treat a patient with an organ, such as the liver, in need of functional assistance.

The invention features methods for culturing cells including: providing a gas-permeable, liquid-impermeable membrane having a first surface and a second surface; seeding cells on the first surface of the gas-permeable, liquid-impermeable membrane; contacting the cells with a nutrient-containing culture medium; providing an oxygenated fluid to the second surface of the gas-permeable, liquid-impermeable membrane at a pressure sufficient to provide transmembrane oxygenation to the cells seeded on the first surface; and culturing the cells under conditions that promote viability and function of the cells.

The device can be seeded with hepatocytes, e.g., porcine, equine, ovine, bovine, rabbit, rat, canine, feline, or murine hepatocytes. Additionally, the device can be seeded with human hepatocytes. The device can be seeded with 2 to 20 billion hepatocytes. The hepatocytes can be seeded directly onto the gas-permeable, liquid-impermeable membrane and then coated with collagen. Alternatively, the gas-permeable, liquid-impermeable membrane can be coated with collagen, and the hepatocytes can be seeded directly onto the collagen-coated membrane. Cells can seeded across the entire membrane from above the membrane.

In one embodiment, the oxygen contained in the oxygenated fluid is at or above the critical partial pressure of oxygen.

In one embodiment, the cells are preserved. The cells can be preserved by cryopreservation, hypothermic storage, or lyophilization.

The gas-permeable, liquid-impermeable membrane material can be made of, e.g., polystyrene, polyolefin, polyethylene, polypropylene, polyvinylidene fluoride, polycarbonate, hydrophobic-treated nylon, polyurethane, polyester, layered styrene-butadiene-styrene/ethyl vinyl acetate/styrene-butadiene-styrene, or layered styrene-butadiene-styrene/polyethylene.

The first surface of the gas-permeable, liquid-impermeable membrane can be treated, e.g., corona treated. In another embodiment, the first surface of the gas-permeable, liquid-impermeable membrane is collagen coated.

In one embodiment, the concentration of oxygen in the oxygenated fluid is between about 0% to about 90% oxygen. Additionally, the concentration of oxygen in the oxygenated fluid can be between about 19% to about 60%, or 40% to about 60%, oxygen. The concentration of oxygen in the oxygenated fluid can be controlled to promote or downregulate cell function.

In one embodiment, the nutrient-containing culture medium is perfused. Additionally, the method can further include filtering blood plasma.

The invention also features a flow-through cell culturing device including a housing with an oxygenated fluid inlet and an oxygenated fluid outlet, a liquid inlet and a liquid outlet, and first and second walls to form a chamber; a gas-permeable, liquid-impermeable membrane arranged between the first and second walls to separate the chamber into an oxygenated fluid compartment comprising an oxygenated fluid entry and an oxygenated fluid exit, and a liquid compartment comprising a liquid entry and liquid exit; and a liquid-permeable membrane arranged between a wall and the gas-permeable, liquid-impermeable membrane to separate the liquid compartment into a cell compartment and a liquid perfusion compartment, wherein the oxygenated fluid inlet and oxygenated fluid outlet are arranged such that oxygenated fluid entering the oxygenated fluid inlet flows into the oxygenated fluid entry and through the oxygenated fluid compartment and exits the oxygenated fluid compartment through the oxygenated fluid exit and the housing through the oxygenated fluid outlet, and wherein the liquid inlet and liquid outlet are arranged such that liquid entering the liquid inlet flows into the liquid entry and through the liquid-perfusion compartment and exits the liquid-perfusion compartment through the liquid exit and the housing through the liquid outlet.

In one embodiment, wherein in use, cells are seeded onto the gas-permeable, liquid-impermeable membrane, and the space between the gas-permeable, liquid-impermeable and liquid-permeable membranes is greater than the size of a cell. In addition, wherein in use, cells can be seeded onto either of the gas-permeable, liquid-impermeable membrane or the liquid-permeable membrane, and the space between the gas-permeable, liquid-impermeable and liquid-permeable membranes is about equal to the size of one cell. Additionally, wherein in use, cells can be seeded onto the gas-permeable, liquid-impermeable membrane, and onto the liquid-permeable membrane, and the space between the gas-permeable, liquid-impermeable and liquid permeable membranes is about equal to the size of two adjacent cells.

The device can further include a liquid-permeable hollow fiber arranged in the liquid compartment. Additionally, the housing can be arranged to enable stacking of one device on top of another device.

The invention also includes a liver assist system including a flow-through cell culturing device of the invention; a first conduit for conducting plasma from a patient to the housing inlet; a second conduit for conducting plasma from the cell culturing device to the patient; and a pump for moving plasma through the conduits and cell culturing device. The system can further include a plasma separator to remove blood cells from whole blood to provide plasma that is passed through the cell culturing device. The system can additionally include a bubble trap, to remove bubbles from the plasma in the first conduit prior to entering the cell culturing device.

The invention also features a liver assist system including a flow-through cell culturing device of the invention; an immunoisolation device; a first conduit for conducting plasma from a patient to an immunoisolation device; a second conduit for conducting plasma from the immunoisolation device to the patient; a third conduit for conducting liquid medium from the cell culturing device to the immunoisolation device; and, a fourth conduit for conducting liquid medium from the immunoisolation device to the patient; and, a pump for moving plasma through the conduits and cell culturing device.

The invention also includes a method of filtering blood plasma. This method includes seeding a flow-through cell culturing device of the invention with hepatocytes; introducing blood plasma into the liquid inlet of the device; supplying an oxygenated fluid into the oxygenated fluid inlet of the device; allowing the oxygenated fluid to flow through the oxygenated fluid compartment and out of the device through the oxygenated fluid outlet; and allowing the blood plasma to flow through the device and exit through the liquid outlet, thereby filtering the blood plasma.

The invention also includes a method for treating a patient in need of liver assist. The method includes attaching the liver assist system of the invention to the blood flow of a patient and treating the patient.

The invention also features a flow-through cell culturing device including a housing with a liquid inlet and a liquid outlet, an oxygenated fluid inlet and an oxygenated fluid outlet, and first and second walls to form a chamber; and a gas-permeable, liquid-impermeable membrane arranged between the walls to separate the chamber into an oxygenated fluid compartment comprising an oxygenated fluid entry and an oxygenated fluid exit, and a liquid compartment comprising a liquid entry and liquid exit, wherein the gas-permeable, liquid-impermeable membrane is seeded with cells, wherein the liquid inlet and liquid outlet are arranged such that biological liquid entering the liquid inlet flows into the liquid entry and through the liquid compartment and exits the liquid compartment through the liquid exit and the housing through the liquid outlet, and wherein the oxygenated fluid inlet and oxygenated fluid outlet are arranged such that oxygenated fluid entering the oxygenated fluid inlet flows into the oxygenated fluid entry and through the oxygenated fluid compartment and exits the oxygenated fluid compartment through the oxygenated fluid exit and the housing through the oxygenated fluid outlet.

The gas-permeable, liquid-impermeable membrane can be porous or non-porous. The gas-permeable, liquid-impermeable membrane comprises polystyrene, a polyolefin, polyethylene, polypropylene, polyvinylidene fluoride, polyurethane, poly(styrene-butadiene-styrene), poly(ethyl vinylacetate), nylon, silicon rubber, poly (tetrafluoroethylene), or composites, mixtures, or copolymers thereof. The gas-permeable, liquid-impermeable membrane can be surface treated, e.g., with a corona discharge or a coating of extracellular matrix.

In one embodiment, a gel is disposed on the cells. Alternatively, a gel can be disposed on the gas-permeable, liquid-impermeable membrane. The gel can contain cells suspended within said gel.

The invention also features a method of filtering blood plasma including seeding a flow-through cell culturing device of the invention with hepatocytes; introducing blood plasma into the liquid inlet of the device; supplying an oxygenated fluid into the oxygenated fluid inlet of the device; allowing the oxygenated fluid to flow through the oxygenated fluid compartment and out of the device through the oxygenated fluid outlet; and allowing the blood plasma to flow through the device and exit through the liquid outlet, thereby filtering the blood plasma.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The new flow-through cell culturing devices and organ assist systems provide numerous advantages. The new devices allow various cells to be cultured with desirable levels of mass transport of oxygen and other nutrients, waste products, and beneficial products, while potentially reducing detrimental shear stress normally associated with higher levels of media flow. As a result, even relatively shear-sensitive cells such as hepatocytes can be cultured for extended periods of time at relatively low media flow rates with high levels of function. As a consequence, oxygenation and perfusion can be controlled independently. Further, these devices allow direct treatment of surfaces for promotion of cell attachment and function as well as more uniform distribution of cells within the devices in the form of laminar cultures that simulate the in vivo architecture of the liver. These features allow the new flow-through cell culturing devices to be used in organ, e.g., liver assist systems.

Clinical studies have shown that adequate liver function can be maintained in vivo with as little as 10% of the normal cell mass suggesting that an effective LAD would support at least $10^{10}$ hepatocytes with approximately in vivo levels of function.

Other features and advantages of the invention will be apparent from the following detailed description, and from the claims.

DETAILED DESCRIPTION

The new cell culturing devices enable the culture of relatively large numbers and high densities of cells, e.g., hepatocytes, in the devices while minimizing total void volume of liquid; allowing precise control, scalability and modularity; and separating medium flow (for supply of nutrients and soluble toxins and/or inducers, and removal of wastes and metabolic byproducts) from oxygenation. The new devices are inherently scalable and modular. The new devices allow separation of oxygenation from flow of biological liquids through the use of a gas-permeable but liquid-impermeable membrane on which the cells are grown or cultured directly.

Figure 1:
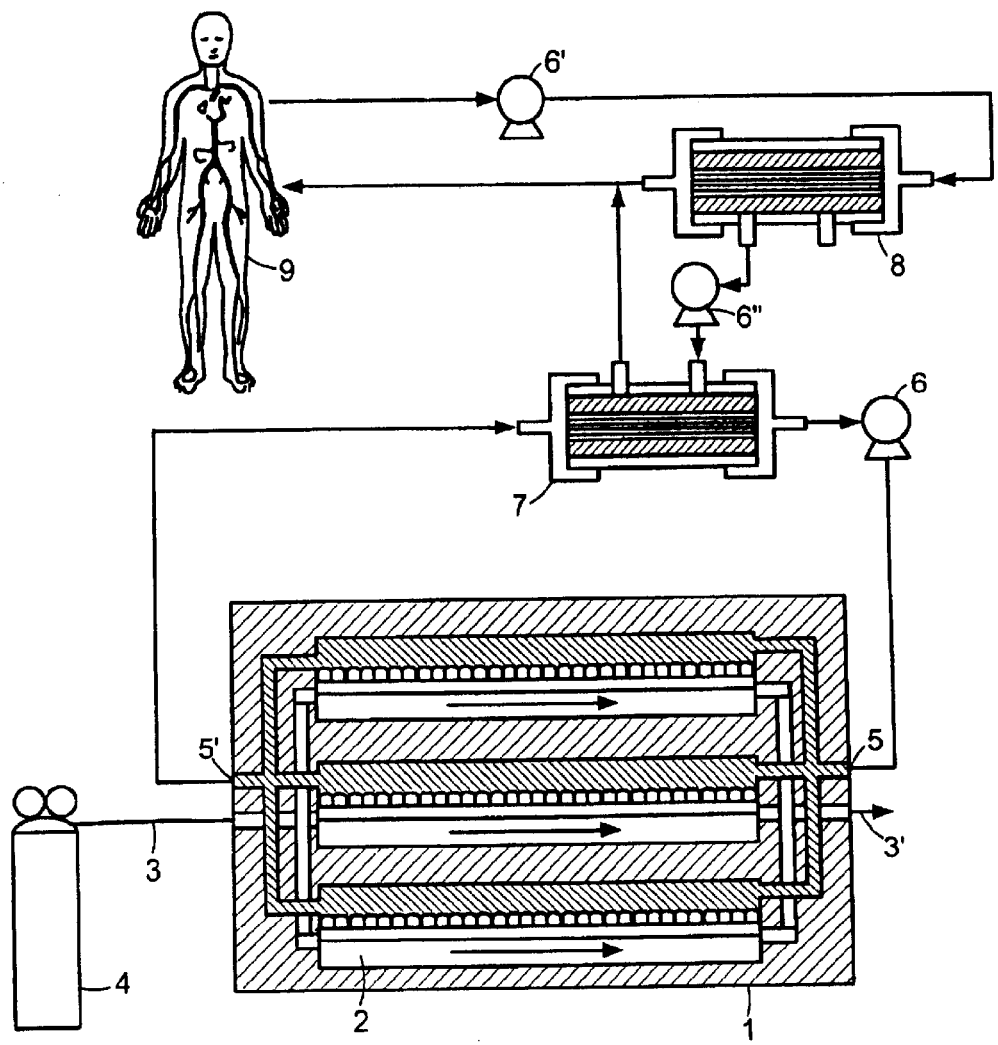
FIG. 1 is a schematic diagram of an extracorporeal liver support system.

FIG. 1 shows a schematic diagram of an extracorporeal liver support system in which the new cell culturing devices can be used. The system includes a bioreactor 1 with multiple cartridges 2. The bioreactor includes an oxygenated fluid inlet 3 for introducing an oxygenated fluid from an oxygenated fluid supply 4, an oxygenated fluid outlet 3', a liquid inlet 5 for introducing a biological liquid, supplied by pump 6 from immunoisolation unit 7, into the bioreactor, and a liquid outlet 5' for removing the biological liquid from the bioreactor for return to the immunoisolation unit 7. Blood from a patient 9 flows via pump 6' into a plasmapheresis unit 8, from which a portion of the plasma then flows into the immunoisolation unit 7, via pump 6". Treated plasma flows from the immunoisolation unit 7 and is mixed with blood from the plasmapheresis unit 8 prior to flowing back into the patient 9.

Figure 2:
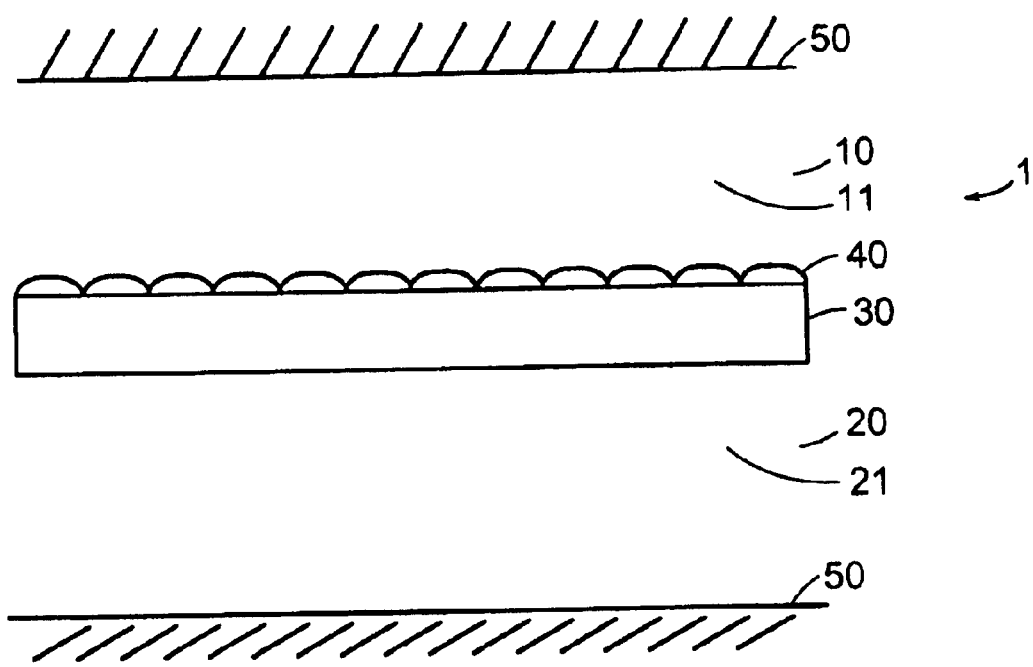
FIG. 2 is a schematic diagram of one embodiment of a "two-compartment" cell culturing device of the invention including a gas-permeable, liquid-impermeable membrane separating the two compartments.

The new cell culturing devices contain one or more two-compartment cartridges (or units). FIG. 2 shows one embodiment of a two-compartment cartridge that includes a chamber 1 having impermeable walls 50 and a gas-permeable, liquid-impermeable membrane 30 separating the chamber into two regions, or compartments, a first compartment 10, and a second compartment 20. The first compartment 10 is defined by one of the impermeable walls 50, the side walls of the chamber, and the gas-permeable, liquid impermeable membrane 30. The first compartment 10 is a "liquid compartment" containing a biological liquid 11, such as cell culture medium, a balanced salt solution, blood, or plasma, and cells 40. The cells 40 are substantially cultured on the membrane 30 and in contact with the biological liquid 11.

Walls are typically composed of cell-compatible plastic such as polystyrene and co-polymers that are thick to make them impermeable to liquids and gases, metals or composites thereof such as aluminum, stainless steel and other alloys. These materials can be used for other device components including fittings and manifolds.

The second compartment 20 is a "oxygenated fluid compartment" and is defined by the second of the impermeable walls 50, the side walls of the chamber, and the gas-permeable, liquid-impermeable membrane 30. An oxygenated fluid 21, typically a gas but also possibly a liquid, capable of carrying oxygen or an oxygenated gas and allowing the transport of oxygen through the gas-permeable, liquid-impermeable membrane 30, flows through the compartment 20. Oxygen is available to the cells in the liquid compartment from the oxygenated fluid compartment via the gas-permeable, liquid impermeable membrane 30. Oxygenated fluids can be gases or liquids and can include air, oxygen-enriched air, oxygen gas, mixtures of oxygen and other gases such as carbon dioxide, nitrogen, argon, helium and other gases commonly found in nature; liquids such as fluorocarbons, perfluorinated liquids, and aqueous solutions containing natural or synthetic hemoglobin or equivalents.

Although FIG. 2 depicts the chamber 1 divided such that the liquid compartment 10 is above the gas-permeable, liquid-impermeable membrane 30 and the oxygenated fluid compartment 20 is below the membrane, the chamber can be oriented in any direction as long as the membrane divides the chamber into two compartments. Preferably the height of each compartment is constant (although not necessarily the same for both compartments); however, the height of each compartment can be non-uniform, e.g., varying along the length and/or width of the compartment.

The biological liquid 11 in the first (liquid) compartment 10 supplies the cells 40 with basic nutrients for cell culture and carries away metabolites. The biological liquid also supplies the cells with toxins, aminated molecules, and other biological waste products to be metabolized and carries away detoxified products, secreted factors, and proteins. For in vitro culture of cells this biological liquid preferably is a medium designed for cell culture. The biological liquid is preferably supplied to and removed from the compartment interior through an opening. More preferably there are at least two openings (not shown in FIG. 2), one opening serving as an inlet opening to supply biological liquid from a biological liquid source and another opening serving as an outlet to discharge or drain the biological liquid. The openings communicate between the interior and exterior of the liquid compartment 10 by a port or manifold. Ports can be connected with other liquid compartments of other bioreactor units or cartridges in parallel, in series, or both, to create a flow circuit or loop for the perfusion of the biological liquid. The addition of other ports can serve as vents for air displacement during filling or as a means of draining the compartment when the other ports are attached to those of another unit.

The oxygenated fluid in the second (gas) compartment 20 is preferably supplied to and removed from the compartment interior through an opening. More preferably there are at least two openings (not shown in FIG. 2), one opening serving as an inlet opening to supply oxygenated fluid from an oxygenated fluid source 4 and another opening serving as an outlet to discharge or vent oxygenated fluid. The openings communicate between the interior and exterior of the oxygenated fluid compartment 20 by a port or manifold. Again, ports can be connected with other oxygenated fluid compartments of other bioreactor units or cartridges in parallel, in series, or both, to create a flow circuit or loop for the oxygenated fluid. Other ports for venting may also be added to the compartment wall.

The membrane 30 is gas-permeable and liquid-impermeable. Cells 40 may attach on any surface inside the liquid compartment, but it is preferred that the cell mass be substantially cultured on the membrane and that the membrane serves as a cell culture substrate. Cells exchange gas such as oxygen with the oxygenated fluid through the membrane. The membrane preferably is in a planar, flat-sheet configuration and extends in a plane to separate the liquid compartment 10 and the oxygenated fluid compartment 20. The membrane is gas-permeable to allow transport of oxygen and possibly other gases from the oxygenated fluid to the cells and from the cells to the oxygenated fluid. The membrane must be impermeable to liquid under pressures encountered in operation but permeable to gas in the range from about 0.1 mL/m²/day to about 1000 L/m²/day. The membrane must also be able to be sterilized, resistant to puncture, ripping, and wrinkling, and be able to be handled during manufacture of the device.

Membrane materials of one or more layers having the following characteristics are suitable for use in the invention: relatively permeable to oxygen and at least partially impermeable to water in the absence of large pressure differences across the membrane 30, relatively non-cytotoxic to cells on at least one side (such that the attachment and function of the cells is not limited by the material or that the material can be surface treated on one side such that the attachment and function of the cells is not limited by this surface-treated side of the material), and relatively non-degrading in the presence of the oxygenated fluid 21 and/or biological liquid 11. For double-sided materials the side facing the liquid compartment 10 must be relatively non-cytotoxic and relatively non-degrading in the presence of the biological liquid and the side facing the oxygenated fluid compartment 20 must be relatively non-degrading in the presence of the oxygenated fluid. Membrane materials having these characteristics can be easily obtained commercially or prepared using standard techniques.

Specific membrane materials suitable for use in the invention include single layers and multi-laminate composites of non-porous or microporous materials such as non-porous polystyrene, including 0.002-in thick polystyrene such as POLYFLEX® (from Plastics Suppliers); microporous polyolefin; microporous high-density polyethylene (HDPE), such as TYVEK®, particularly TYVEK® 1073 (DuPont); microporous polypropylene; microporous polyvinylidene fluoride; track-etched polycarbonate (with relatively small pores and no-wetted); hydrophobic-treated nylon; polyurethane; microporous polyester (with hydrophobic pores); other inorganic polymers, such as microporous inorganic polymers and non-porous silicone rubbers; co-extruded polystyrene and polyethylene; a three-layered co-extruded film of styrene-butadiene-styrene/ethyl vinyl acetate/styrene-butadiene-styrene (SBS/EVA/SBS); and a two-layered co-extruded film of styrene-butadiene-styrene/polyethylene (SBS/PE).

Oxygenation of cells 40 through the gas-permeable, liquid-impermeable membrane 30 requires that either the membrane itself be self-supporting (e.g., possess sufficient mechanical stiffness to withstand gravity, the weight of the membrane, the weight of the biological liquid if the biological liquid is oriented above the membrane, and any applied pressure differences across the membrane) or that the membrane be combined with or laminated onto a stiffer support material. This support material must be either sufficiently permeable, porous, or spatially distributed such that it presents no additional significant limitations to gas transport, particularly for oxygen, and also has the requisite mechanical properties. For example, the use of impermeable posts relatively widely spaced to support the membrane can satisfy these requirements.

In the culture of some cell types, oxygenation is by the cell culture medium. However, some cell types, such as hepatocytes, have oxygen requirements that are characteristically high compared to other cell types. The function of viable hepatocytes can also depend on oxygen tension. Another consideration which intensifies this type of problem in a cell culturing or organ assist device is the need to incorporate relatively large numbers and high densities of cells into the device while limiting volume of biological liquid.

The rate at which oxygen is consumed by the cells must be balanced by the transport of oxygen to the cells, either by transport of oxygen across the membrane or through the flowing biological liquid. The kinetics of oxygen consumption by the cells is given by the oxygen uptake rate (OUR), typically described in terms of Michaelis-Menten kinetics and expressed as moles of oxygen consumed per cell per unit time, multiplied by the cell number. The rate of transport of oxygen across the membrane is given by the product of the volumetric flow of oxygen per unit of partial pressure difference (expressed as volume of oxygen per unit area per unit time per unit partial pressure difference), the partial pressure difference across the membrane, and the projected area of the membrane. The rate of transport of oxygen through the biological liquid is given by the negative of the product of the diffusivity of oxygen in the biological fluid, the gradient in the concentration of oxygen perpendicular to the membrane at the surface of the membrane where the cells are cultured on, and the projected area of the membrane.

Minimum levels of oxygenation of cells maintained in the cell culturing device can be determined by balancing the transport of oxygen into the device with the rate of consumption of oxygen by cells within the device. For devices operated statically, i.e., without introducing new biological liquid into the device, the only mechanism of transport for oxygen is transmembrane. The rate of transmembrane transport is given by the product of the flux of oxygen across the membrane and the planar area of the membrane; the flux is itself a product of the permeability of the membrane, $P_m$, and the difference in concentration of oxygen across the membrane. The rate of consumption of oxygen is given by the OUR.

For devices operated statically the governing equation balancing transport and consumption is:

$$pO_{2,c} = RT\left(\frac{OUR}{P_m}\right),$$

where $pO_{2,c}$ is the critical partial pressure of oxygen for oxygenation, R is the gas constant, and T is temperature. Partial pressures of oxygen greater than this $pO_{2,c}$ provide sufficient oxygenation; partial pressures of oxygen below this $pO_{2,c}$ provide insufficient oxygenation. This equation can be used to design and operate such cell culturing devices 1 in the absence of flow of the biological liquid 11.

Figure 3:
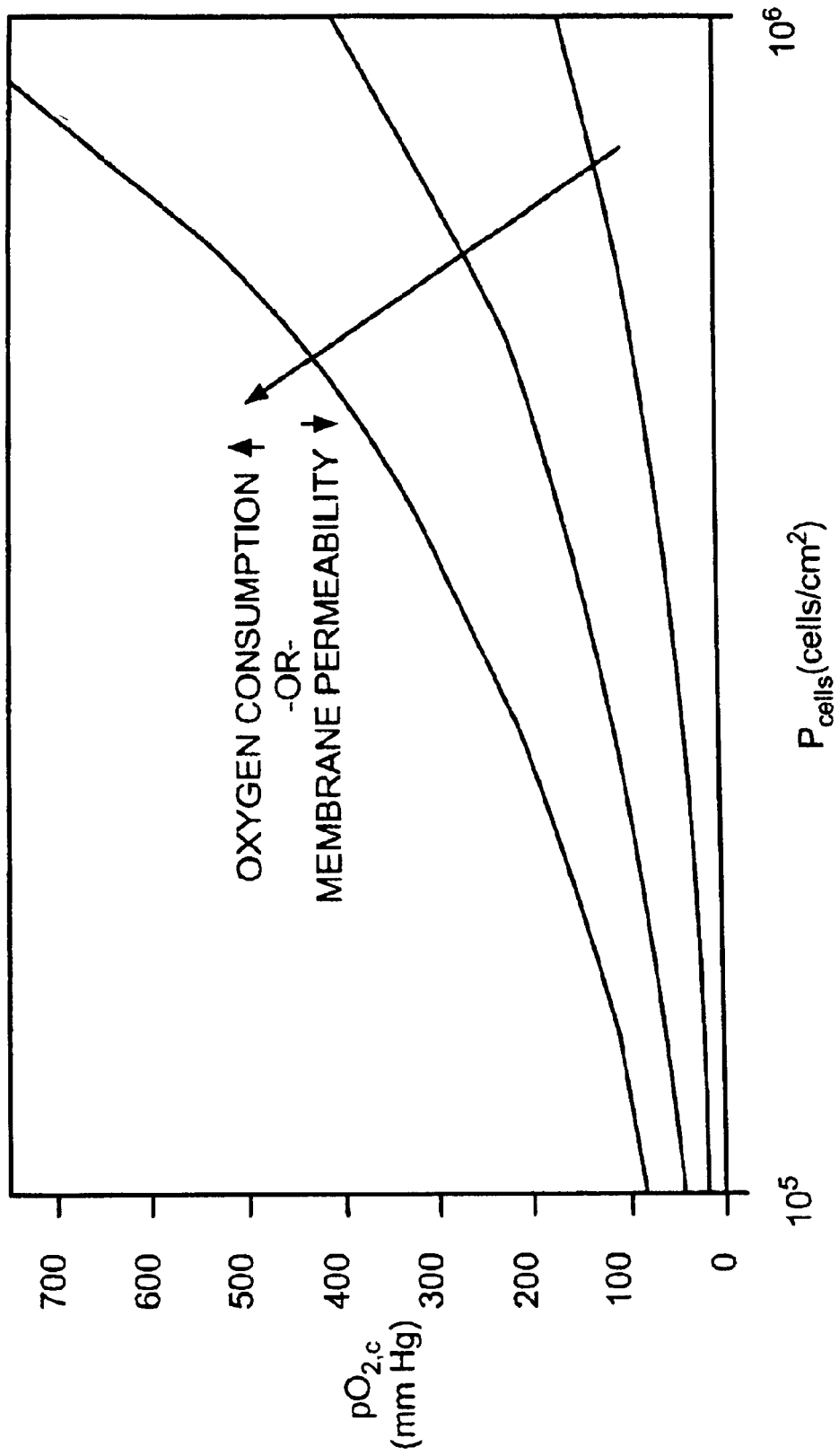
FIG. 3 is a graph showing the partial pressure of oxygen in the device feed gas necessary to achieve sufficient oxygenation, under transmembrane oxygenation, to balance the oxygen consumption rate of hepatocytes for a range of cell densities ($\rho_{cells}$) and for different membrane permeabilities to oxygen and/or cellular rates of oxygen consumption.

The governing equation for oxygenation is plotted in FIG. 3 for simulated data for devices comprising 0.002 in-thick polystyrene, available as Polyflex® from Plastics Suppliers (Columbus, Ohio), for which $P_m$ is on the order of $10^4$ mL/m²-day-atm, and operated at physiological temperatures (310 K) and for cellular rates of consumption of oxygen of $1\times10^{-16}$, $5\times10^{-16}$, and $1\times10^{-15}$ moles/cell-s. These values for consumption of oxygen are based on data for primary porcine hepatocytes presented in Balis et al., Metabolic Engineering, 1:1–14 (1999). These curves will shift towards the top and left when membranes with lower permeabilities to oxygen are used and towards the bottom and right when membranes with higher permeabilities to oxygen are used.

In contrast, when oxygenation is supplied to cells on a gas-impermeable support through the layer of quiescent biological liquid bathing them and a gas-permeable membrane in contact with that layer of biological liquid, the governing equation balancing transport and consumption of oxygen is:

$$pO_{2,c}^* = RT\left(\frac{OUR}{P_m}\right)\left(1 + \frac{hP_m}{SRTD}\right),$$

where h is the thickness of the layer of the biological liquid, S is the solubility of oxygen in the biological liquid, and D is the diffusivity of oxygen in the biological liquid. Because the transport resistance to oxygen will always be greater for this configuration, assuming a membrane with an identical $P_m$, this second configuration will always result in less oxygenation for a given concentration of oxygen.

The governing equations also will depend on the perfusion of medium. However, the basic trends between the two governing equations will not change with direction, volumetric flow rate, or any other characteristic of perfusion.

For example, greater control of oxygenation will always be possible, for membranes with identical permeabilities to oxygen, for direct transmembrane oxygenation of cells compared to sequential transmembrane and then transmedium oxygenation of cells, regardless of the rate of perfusion, provided that the directionality of oxygenation per se does not effect the cells.

Various other specific embodiments of two-compartment cell culturing devices with a gas-permeable, liquid-impermeable membrane will now be described. These embodiments are depicted schematically in FIGS. 4a–4i.

Figure 4A:
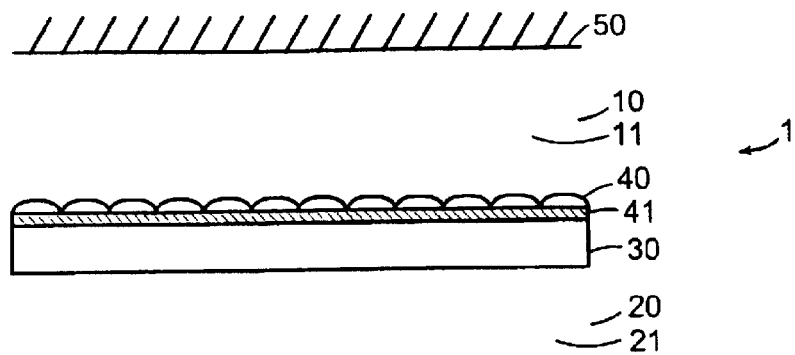
FIGS. 4a through 4f are schematic diagrams of embodiments of "two-compartment" cell culturing devices of the invention including a gas-permeable, liquid-impermeable membrane separating the two compartments.

FIG. 4a shows an alternate basic configuration for a two-compartment cell culturing device 1 comprising a cell compartment 10 containing a biological liquid 11; an oxygenated fluid compartment 20 containing an oxygenated fluid 21; a gas-permeable, liquid-impermeable membrane 30 with surface 41; cells 40; and rigid, impermeable walls 50. The liquid compartment 10 and the oxygenated fluid compartment 20 are separated by the gas-permeable, liquid-impermeable membrane 30, surface treated on the side of the membrane facing the liquid compartment. The cells 40 are cultured on the surface 41 while contacting the biological liquid 11 in the liquid compartment and are able to access oxygen through the gas-permeable, liquid-impermeable membrane 30 from an oxygen source that supplies oxygenated fluid 21 to the oxygenated fluid compartment 20.

The surface 41 may be advantageous or, as with some cells that do not adhere well, necessary, to induce cell adhesion and promote desired cell function. This surface, which may include one or more coating materials, is applied to at least a portion of the membrane and may extend into the interior of the membrane from the side facing the liquid compartment 10. Coating materials that can be applied to the membrane include, but are not limited to: biological coatings such as collagen and other extracellular matrix components, including fibronectin, preparations of extracted biological matrices, and proteoglycans; fibrin; RGD-containing and similar peptides; biosynthetic coatings chemically or biologically synthesized, and/or some other materials that will induce cell adhesion and/or desired cell functions. A preferred coating is collagen, more preferably collagen type I. These coatings may either passively adsorb to the membrane or chemically react (such as by covalent grafting) with the membrane. The membrane may need to be treated with one or more coatings or layers of coatings to make cells adhere and function; these coatings may be identical or dissimilar in composition and/or concentration.

Still another preferred means for improving cell compatibility to the membrane is to provide it with a collagen coating. Coatings, distinguished from bulk gels, are essentially two-dimensional as they are molecular in thickness and are dry on the membrane surface while bulk gels have bulk, three-dimensional thickness and are hydrated. Multiple surface treatments may be applied to the membrane in sequence, for example, treatment with corona discharge followed by coating of extracellular matrix, such as collagen, preferably with collagen type I.

Another method for treating the membrane 30 to improve cell adhesion is a physical surface treatment, such as corona discharge in the presence of an oxygen-bearing gas (e.g., air). Corona discharge incorporates oxygen atoms into the exposed surface such that it is oxidized, more hydrophilic, and sometimes charged. The extent of this treatment is such that the material now possesses a surface free energy (measured in terms of dynes/cm$^2$ by wettability) and other chemical characteristics similar to those characteristics typically associated with tissue-culture dishes. This treatment is conducted for a period of time sufficient to achieve modification of the exposed planar surface to this extent (or higher or lower, depending on whether the cells respond more favorably to a surface with a different free energy), but without significantly compromising the properties of the underlying base material itself. Multiple surface treatments may be applied in sequence, for example, treatment with corona discharge followed by coating with extracellular matrix, such as collagen, preferably with collagen type I.

Corona discharge treatment typically modifies only the surface chemistry of a material or membrane without altering its physical topography. Corona discharge involves exposing the surface to a high-frequency electrical discharge in the presence of air or other oxygen-bearing gas, such that oxygen atoms are incorporated into the surface of the material such that it is now oxidized. This treatment increases the surface fee energy and hydrophilicity of plastic, paper, and metalized films. Systems to apply a corona discharge to materials are commercially available from companies such as Corotec Corp., Farmington, Conn. These systems consist of a high voltage transformer and web of electrodes designed to apply up to kilowatt levels of energy to the surface at frequencies as high 40 kHz. Exposing oxygen to a high voltage electrical discharge generates ozone, which chemically reacts with the surface to incorporate oxygen into it. This treatment may be carried out at room temperature under environmental conditions typically found in chemical and biological laboratories. Operating conditions for corona discharge may vary with the material being surface modified and the extent to which the surface free energy is to be increased.

Figure 4B:
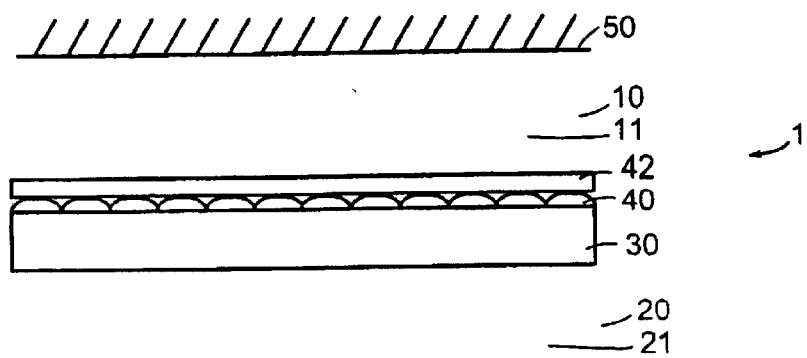

In another embodiment, the cells are sandwiched between the gas-permeable, liquid-impermeable membrane 30 and a bulk gel comprising extracellular matrix components. FIG. 4b shows a cell culturing device 1 comprising a liquid compartment 10 containing a biological liquid 11; an oxygenated fluid compartment 20 containing an oxygenated fluid 21; a gas-permeable, liquid-impermeable membrane 30; cells 40; a bulk gel 42, and rigid, impermeable walls 50. The liquid compartment 10 and the oxygenated fluid compartment 20 are separated by the gas-permeable, liquid-impermeable membrane 30 on which the cells 40 are cultured on the side of the membrane facing the liquid compartment. A bulk gel 42 is disposed over the cells on the side of the cells facing away from the membrane. Cells are provided with nutrients from the biological liquid 11 through the bulk gel 42 and can access oxygen through the gas-permeable, liquid-impermeable membrane 30 from an oxygen source 4 that supplies oxygenated fluid 21 to the oxygenated fluid compartment 20.

Figure 4C:
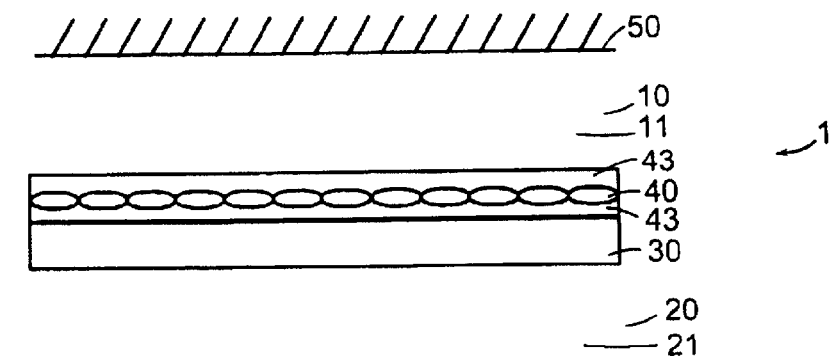

In another embodiment shown in FIG. 4c, the cells are sandwiched between two bulk gels, such as two bulk collagen gels 43 as described in International PCT Application Publication No. WO 96/34087 and in U.S. Pat. No. 5,602,026. In particular, FIG. 4c shows a cell culturing device 1 comprising a liquid compartment 10 containing a biological liquid 11; an oxygenated fluid compartment 20 containing an oxygenated fluid 21; a gas-permeable, liquid-impermeable membrane 30; cells 40; a two-layer gel 43, and rigid, impermeable walls 50. The liquid compartment 10 and the oxygenated fluid compartment 20 are separated by the gas-permeable, liquid-impermeable membrane 30 on which the cells 40 are cultured (on the side of the membrane facing the liquid compartment) deposited between the layers of a two-layer gel 43. Cells 40 are provided with nutrients from the biological liquid 11 through the gel 43, and can access oxygen through the gas-permeable, liquid-impermeable membrane 30 from an oxygen source 4 that supplies oxygenated fluid to the oxygenated fluid compartment 20.

Figure 4D:
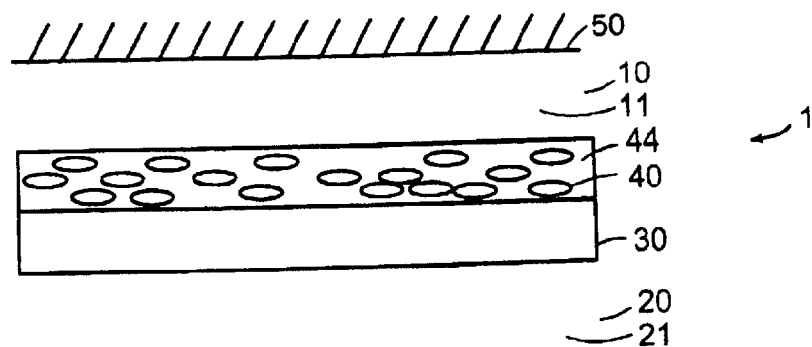

Another useful method for binding cells to the membrane is by using a matrix material. FIG. 4d shows another embodiment of a cell culturing device 1 comprising a liquid compartment 10 containing biological liquid 11; an oxygenated fluid compartment 20 containing an oxygenated fluid 21; a gas-permeable, liquid-impermeable membrane 30; cells 40 within a cell-supporting lattice or scaffold 44; and rigid, impermeable walls 50. This lattice preferably is collagen based, although it also may be based on alternative natural extracellular matrix materials and/or synthetic polymers and blends of polymers. Collagen and other extracellular matrix components can be formed in an uncontracted or contracted lattice comprising collagen to suspend cells in a matrix. When the material is collagen, the lattice with cells is deposited by casting a mixture of acid-solubilized collagen, a pH neutralizing solution, and a cell suspension. This cast gels to form a cell-containing collagen lattice 44. Methods for producing cell-containing collagen lattices, particularly contracted collagen lattices, are previously described in U.S. Pat. Nos. 4,485,096, 5,106,949, and 5,536,656.

Alternatively, the lattice may be a porous, natural or synthetic scaffold wherein the cells are cultured within the scaffold and the scaffold contacts the gas-permeable membrane cells. The porous support either is first applied to the membrane and the cells then seeded into the porous scaffold or first seeded with cells and then applied to the membrane. Examples of porous supports include scaffolds comprising extracellular matrix components, such as collagen sponges, dense fibrillar collagen membranes, and processed tissue membranes. Synthetic porous supports include polyurethane foams.

Figure 4E:
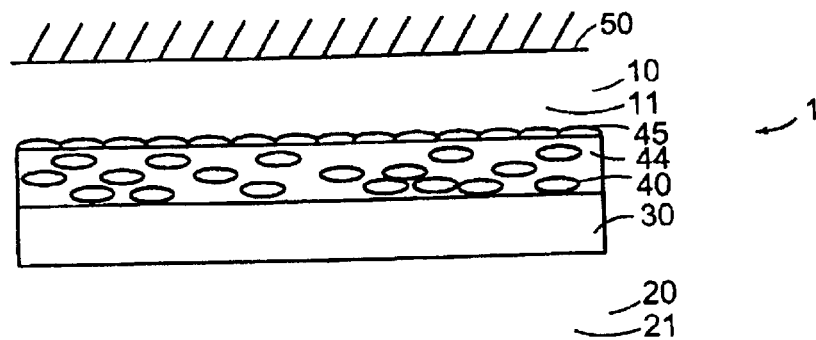
Figure 4F:
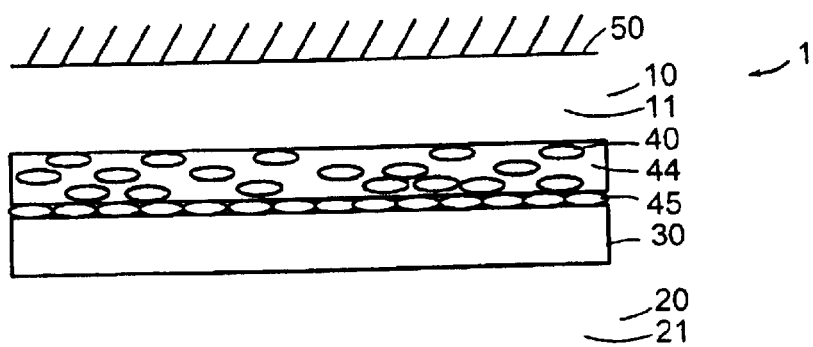

FIGS. 4e and 4f show two additional embodiments of a cell culturing device 1 comprising a liquid compartment 10 containing a biological liquid 11; an oxygenated fluid compartment 20 containing an oxygenated fluid 21; a gas-permeable, liquid-impermeable membrane 30; cells 40 within a cell-supporting lattice 44; a second layer of cells 45; and rigid, impermeable walls 50. FIG. 4e depicts an embodiment in which the second layer of cells 45 is on the side of the lattice 44 facing the liquid compartment 10. FIG. 4f depicts a second embodiment in which the second layer of cells 45 is between the lattice 44 and the membrane 30. The second layer of cells may be the same type or different from the cells within the lattice. An embodiment consisting of a combination of the arrangement of cells in the embodiments shown in FIGS. 4e and 4f also can be realized.

Because some cells have attachment or functional properties which can be adversely affected by direct contact with a flowing biological liquid and are shear sensitive, in some applications it may be desirable to place a liquid-permeable membrane between the flowing biological liquid and the cells to limit hydrodynamic interactions. In this arrangement an additional compartment, a cell compartment, containing the cells is located between the liquid compartment and oxygenated fluid compartment.

Figure 5A:
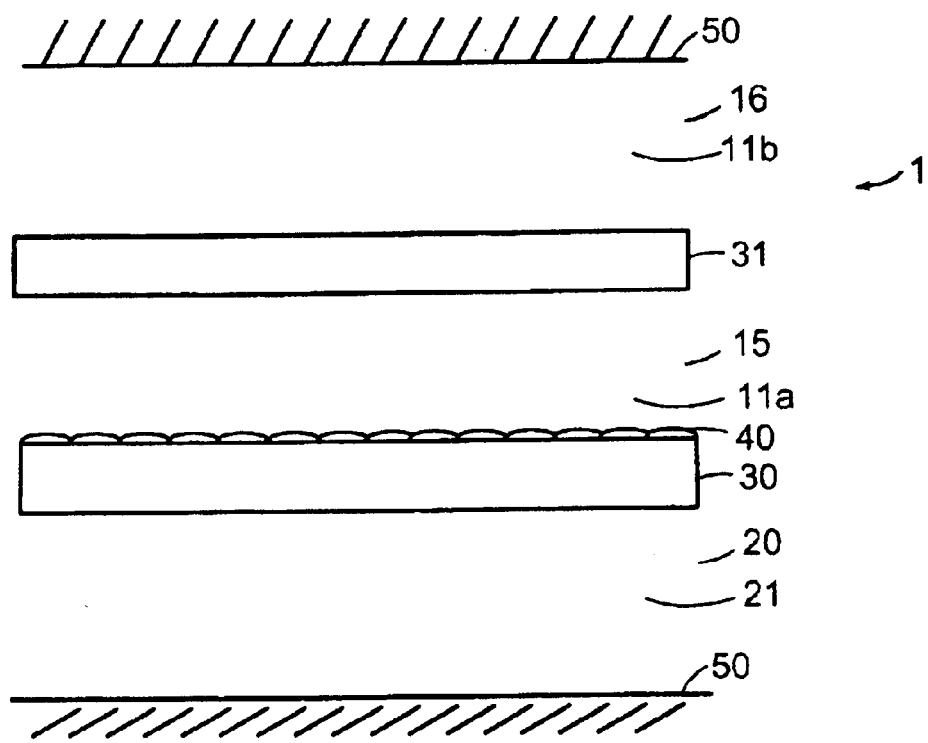
FIGS. 5a through 5f are schematic diagrams of embodiments of "three-compartment" cell culturing devices of the invention including separate gas-permeable, liquid-impermeable and liquid-permeable membranes.

FIG. 5a shows one embodiment of a three-compartment cell culturing device 1 having impermeable walls 50, a gas-permeable, liquid-impermeable membrane 30 separating a first compartment 20 from a second compartment 15, and at least one liquid-permeable membrane 31 separating the second compartment 15 from a third compartment 16. The first compartment 20 is the "oxygenated fluid" compartment and is defined by one of the impermeable walls 50, the side walls of the chamber, and the gas-permeable, liquid-impermeable membrane 30. The second compartment 15 is the "cell" compartment and is defined by the side walls of the chamber, the gas-permeable, liquid-impermeable membrane 30, and the liquid-permeable membrane 31. The third compartment 16 is the "liquid-perfusion" compartment and is defined by the remaining impermeable wall 50, the side walls of the chamber, and the liquid-permeable membrane 31.

Although FIG. 5a depicts the chamber 1 divided such that the liquid-perfusion compartment 16 is above the one or more liquid-permeable membranes 31 and the oxygenated fluid compartment 20 is below the gas-permeable, liquid-impermeable membrane 30, the chamber can be oriented in any direction as long as the cell compartment 15 intervenes between the liquid-perfusion and oxygenated fluid compartments and the gas-permeable, liquid-impermeable membrane 30 is located between the oxygenated fluid and cell compartments and one or more liquid-permeable membranes 31 are located between the cell and liquid-perfusion compartments.

The liquid-perfusion compartment 16 contains a biological liquid 11b, such as cell culture medium, a balanced solution, blood, or plasma. The cell compartment 15 contains both cells 40 substantially cultured on the gas-permeable, liquid-impermeable membrane 30 as well as a biological liquid 11a that may be the same or different from the biological liquid 11b in the liquid perfusion compartment 16. The biological liquids 11a and 11b are in liquid contact through the intervening one or more liquid-permeable membranes 31. The biological liquid 11a supplies the cells 40 with basic nutrients for cell culture, toxins, aminated molecules, and other biological waste products to be metabolized and carries away cell metabolites, detoxified products, secreted factors, and proteins. These molecules are transported across the liquid-permeable membrane 31 to and from the biological liquid 11a.

The cells 40 in the cell compartment 15 are substantially not in contact with the liquid-permeable membrane 31. The gap filled by the volume of the cells and the biological liquid 11a in the cell compartment preferably is uniform in thickness but may be nonuniform. This gap is at least the height of the layer of cells 40 attached to the gas-permeable, liquid-impermeable membrane 30, such that at least some biological liquid 11a intervenes between the cells 40 and the face of the liquid-permeable membrane 31 facing the cells. This gap is maintained by one or more spacers.

The biological liquid 11a in the cell compartment 15 flows very slowly or is static; its flow is substantially unaffected by the flow of the biological liquid 11b in the liquid-perfusion compartment 16. The biological liquid 11a preferentially is initially supplied to the cell compartment 15 during filling and is free to exchange with the biological liquid 11*b* across the liquid-permeable membrane 31. One or more ports can serve as vents for air displacement during filling and/or as means of draining the cell compartment 15 during operation. These other ports may also be manifolded to ports from cell compartments of other bioreactors units in parallel, in series, or both for venting and drainage.

The biological liquid 11*b* is preferentially supplied to and removed from the interior of the liquid-perfusion compartment 16 through an opening. More preferably there are at least two openings (not shown in FIG. 5*a*), one opening serving as an inlet opening to supply biological liquid 11*b* from a biological liquid source and another opening serving as an outlet to discharge or drain the biological liquid 11*b*. The openings communicate between the interior and exterior of the liquid-perfusion compartment 16 by a port or manifold. Ports can be connected with other liquid-perfusion compartments of other bioreactor units in parallel, in series, or both to create a flow circuit or loop for the biological liquid 11*b*. The additional of other ports can serve as vents for air displacement during filling or as a means of draining the liquid-perfusion compartment 16 when the other ports are attached to those of another unit.

An oxygenated fluid 21, typically a gas but also possibly a liquid capable of carrying oxygen or an oxygenated gas and allowing the transport of oxygen through the gas-permeable, liquid-impermeable membrane 30, flows through the oxygenated fluid compartment 20. Oxygen is available to the cells 40 in the cell compartment 15 via the gas-permeable, liquid-impermeable membrane 30. The oxygenated fluid in the oxygenated fluid compartment is preferentially supplied to and removed from the compartment interior through an opening. More preferably there are at least two openings (not shown in FIG. 5*a*), one opening serving as an inlet opening to supply oxygenated fluid from an oxygenated fluid source and another opening serving as an outlet to discharge or vent oxygenated fluid. The openings communicate between the interior and exterior of the oxygenated fluid compartment 20 by a port or manifold. Again, ports can be connected with other oxygenated fluid compartments of other bioreactor units in parallel, in series, or both to create a flow circuit or loop for the oxygenated fluid. Other ports for venting may also be added to the compartment wall.

Figure 5B:
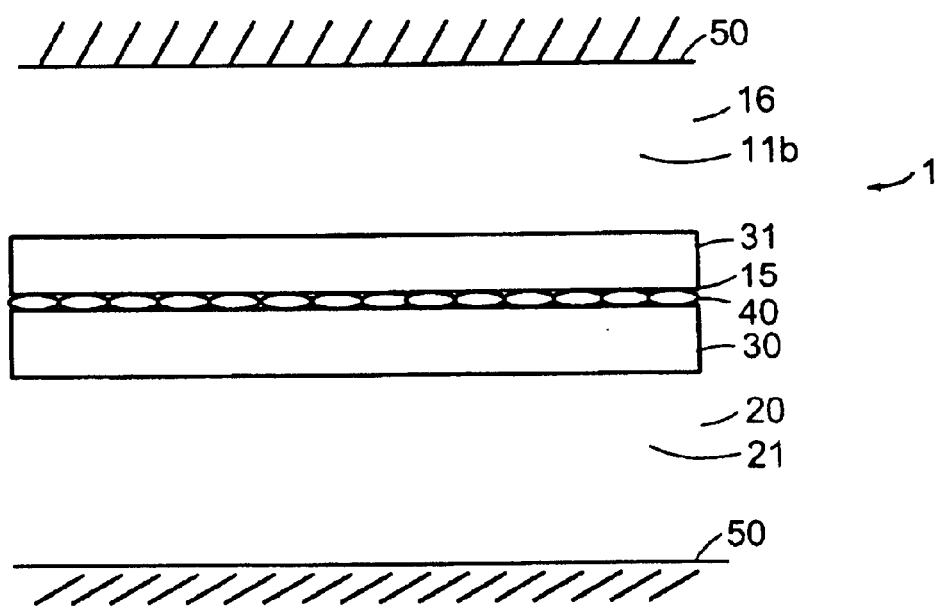

Various other specific embodiments of three-compartment cell culturing devices with separate gas-permeable, liquid-impermeable and liquid-permeable membranes will now be described. These embodiments are depicted schematically in FIGS. 5*b*–*f*. FIG. 5*b* shows one embodiment in which the cells 40 are in direct contact with both the gas-permeable, liquid-impermeable membrane 30 and the liquid-permeable membrane 31. In this embodiment, the cell compartment 15 is reduced in size to a minimal volume, specifically the size of the cells 40 in the cell compartment, when the liquid-permeable membrane 31 contacts the cells growing on the gas-permeable, liquid-impermeable membrane 30.

Figure 5C:
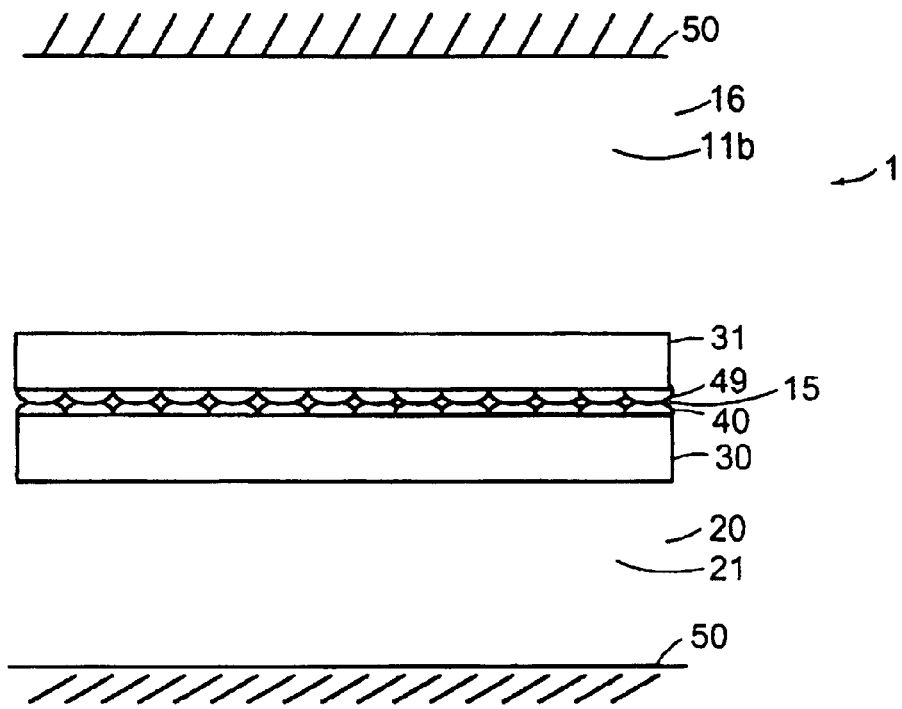

Another alternative embodiment is shown in FIG. 5*c*, in which one layer of cells 40 is attached to the gas-permeable, liquid-impermeable membrane 30 and a second layer of cells 49 is attached to the liquid-permeable membrane 31, to form a cell bilayer or multilayer culture. This embodiment comprises at least two layers of cells. Additional layers of cells may intervene between the layers of cells 40 and 49.

Figure 5D:
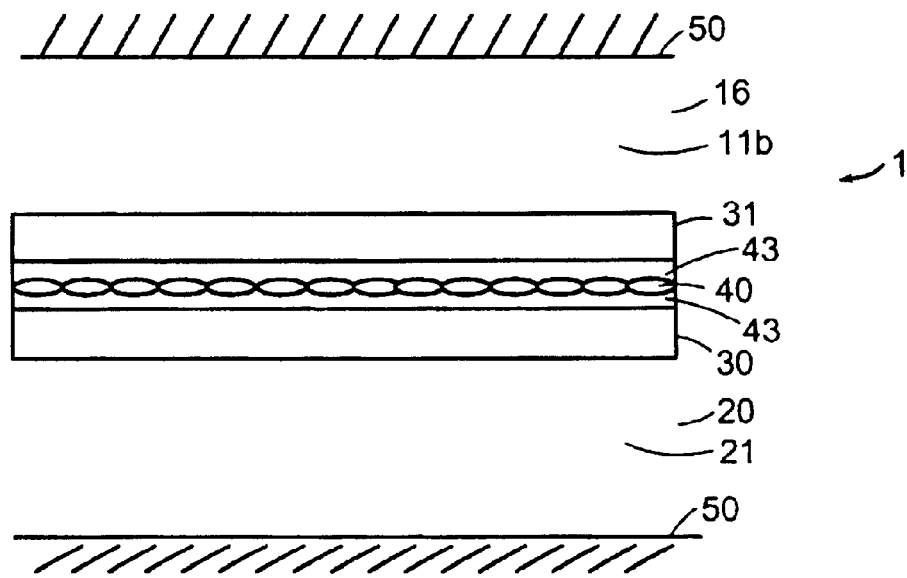

In another embodiment shown in FIG. 5*d*, the cells 40 are sandwiched between two bulk collagen gels 43. In particular, FIG. 5*d* shows a cell culturing device comprising a liquid-perfusion compartment 16 containing a biological liquid 11*b*, such as cell culture medium, a balanced solution, or plasma. The cell compartment 15 contains a first bulk collagen gel 43 disposed on a gas-permeable, liquid-impermeable membrane 30; one or more layers of cells 40 seeded on the gel; a second bulk collagen gel 43 disposed upon the cells; and a liquid-permeable membrane 31 contacting the second gel. The biological liquid 11*b* is in liquid contact through the intervening one or more liquid-permeable membranes 31. The biological liquid 11*b* supplies to, and removes from, the cells 40 components related to cell culture that are transported across the bulk collagen gels 43, the liquid-permeable membrane 31 to and from the biological liquid 11*b*.

Figure 5E:
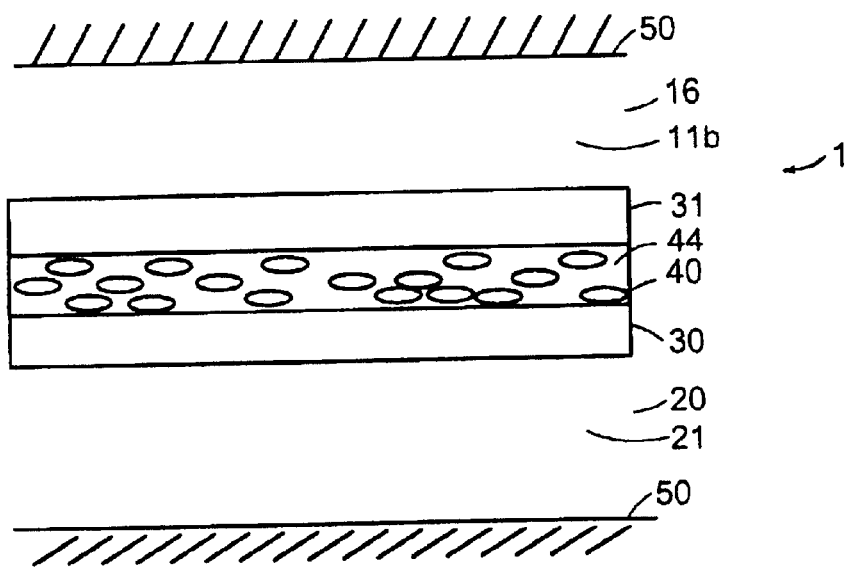

FIG. 5*e* illustrates another embodiment in which a cell-supporting lattice 43 containing cells 40 is sandwiched between the gas-permeable, liquid-impermeable membrane 30 and the liquid-permeable membrane 31. The cell-supporting lattice can be a collagen lattice or can be interchanged with a porous matrix containing cells as described elsewhere herein.

For the embodiments depicted in FIGS. 5*b*–5*e*, a spacer may be added to maintain the height of the cell compartment 15. For the embodiment of FIG. 5*b* this spacer may be omitted if the cells are first seeded onto one of the two membranes 30 and 31 and then the membranes brought together with the cells sandwiched between the two membranes. For the embodiment of FIG. 5*c* this spacer may be omitted if each cell layer 40 is seeded first onto its adjacent membrane and then the cell-seeded membranes brought together.

Figure 5F:
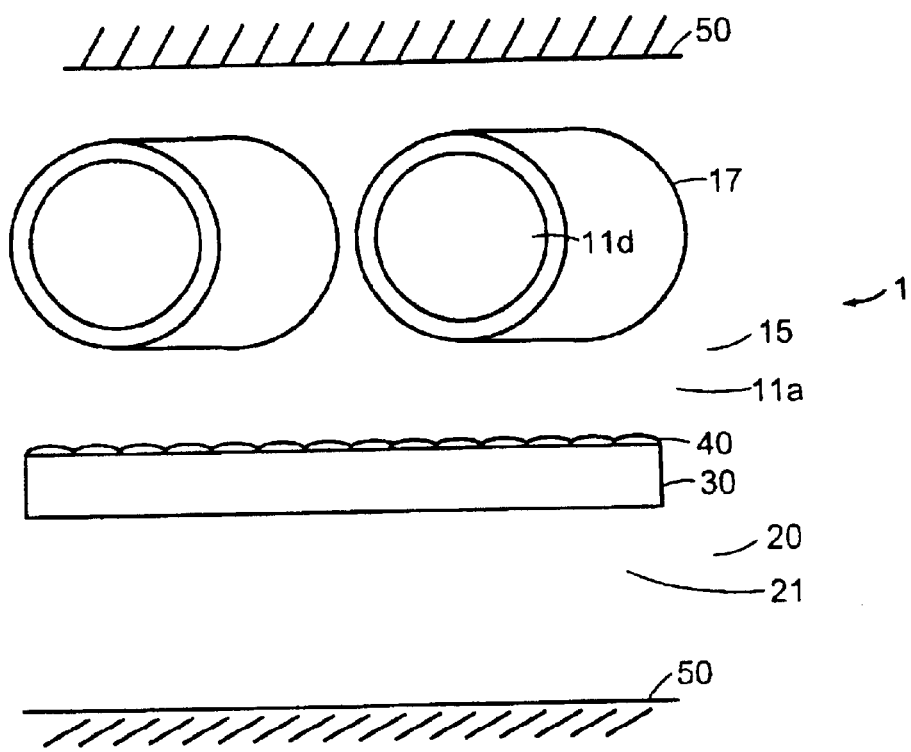

In another embodiment, hollow fibers can be used as the liquid-perfusion compartment 16. A variation of this embodiment is shown in FIG. 5*f*, in which cells 40 are attached to the planar, gas-permeable, liquid-impermeable membrane 30 and hollow fibers 17 extending in a plane above the cells and containing biological liquid 11*d* are located in cell compartment 15. Biological liquid 11*a* in cell compartment 15 can be static or can flow. Biological liquid 11*d* (which can be the same or different from biological liquid 11*a*) preferably flows within the hollow fibers 17. The hollow fibers 17 are made of a liquid-permeable material, much like the liquid-permeable membrane 31 described herein. In this way, nutrients in biological liquid 11*d* can be transported throughout the device at a flow rate that is independent of the flow rate of biological liquid 11*a* in the cell compartment (which is preferably low to reduce sheer stress on cells 40). The orientation of the hollow fibers 17 may be parallel, anti-parallel, or orthogonal to the direction of flow in the oxygenated fluid compartment 20.

To effectively separate the biological liquid 11*d* in the liquid-perfusion compartment 16 from the biological liquid 11*a* in the cell compartment 15, the liquid-permeable membrane 31 or hollow fibers 17 have a pore size large enough to allow for the transport of large molecule nutrients, toxins, factors, metabolites, and secreted proteins, across the membrane but small enough to prevent cell growth through the membrane. Suitable materials for the liquid-permeable membrane include, but are not limited to: cellulosic membranes; porous poly(sulfone) and poly(ether sulfone) membranes; porous untreated nylon and other polyamide membranes; porous polyesters; porous glass; perforated stainless steel; porous (i.e., track-etched) polycarbonate (wetted with PVP, ethanol, or other wetting agents), porous polyvinyl chloride, perforated polydimethylsiloxane; and porous ceramics. Other membrane materials having these characteristics for use in the invention can be selected from commercially available materials or can be prepared using standard techniques.

The flow of oxygenated fluids can be static, in any one direction, or in multiple directions. In relation to oxygenated fluid flow, flow of biological liquids may be in any direction: the same lateral direction, contralateral, or perpendicular, or any combination thereof. For maximal mass transfer preferably the directions of flow are contralateral, e.g. in opposite directions for the biological liquid and oxygenated fluid. For bioreactor units or cartridges connected in parallel, in series, or both the relative directions of flow in each cartridge can be the same or different. The flow of biological liquids and/or oxygenated fluids can be oscillating or time-dependent. Also, the volumetric flow rates of the biological liquids and oxygenated fluids are independent of each other.

The bioreactor unit of the invention includes at least one compartment containing cells and at least one compartment containing oxygenated fluid. The compartments are in a flat, planar arrangement and have a common shared plane between them. A single unit or cartridge can comprise one compartment containing cells and one compartment containing oxygenated fluid housed individually or together in a stacked configuration, with the units separated by a rigid, impermeable member. Because of the unitary nature of the cell culture cartridges or units, the bioreactor is scalable with the addition of surface area and volume to the compartments or the addition of units. In the case where additional units are added, it is preferred that the compartments communicate via the ports to allow flow of biological liquid or medium or oxygenated fluid between them.

Figure 6A:
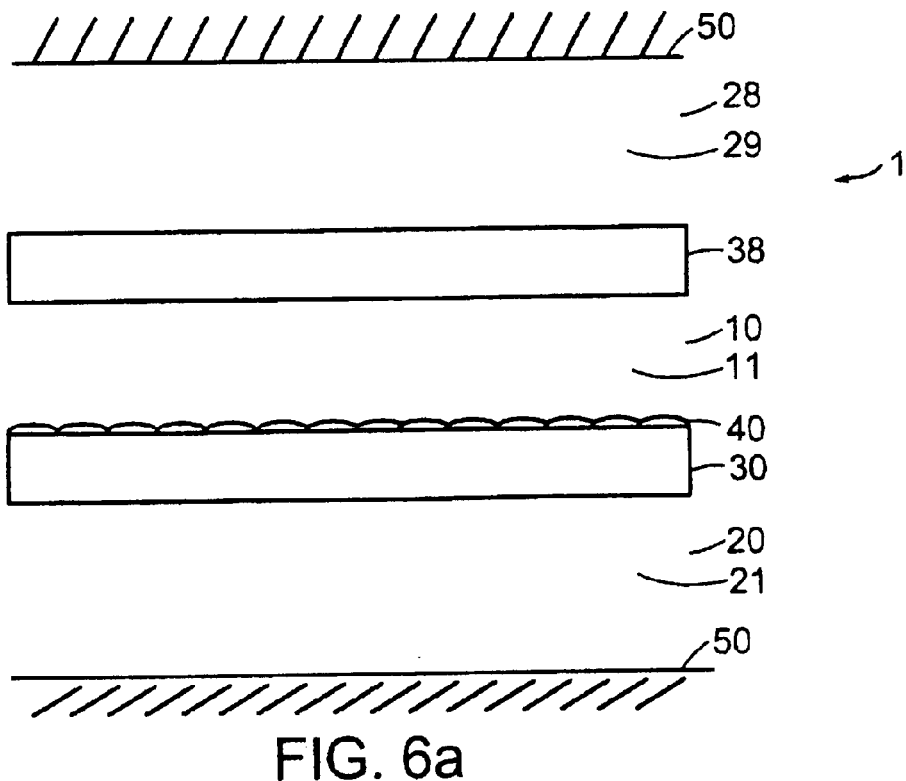
FIGS. 6a to 6c are schematic diagrams of embodiments of multi-compartmented cell culturing device comprising at least two gas-permeable, liquid-impermeable membranes.

FIG. 6a illustrates an embodiment of the cell culturing device comprising one bioreactor unit with two planar gas-permeable, liquid-impermeable membranes, 30 and 38, respectively. Only one of the membranes, 30, is seeded with cells 40 on its side facing the liquid compartment 10 and contacting the biological liquid 11. This embodiment features two oxygenated fluid compartments, 20 and 28, respectively. The oxygenated fluids in the oxygenated fluid compartments 20 and 28, 21 and 29, respectively, may be the same or different, may be flowing in the same or different directions, and may be flowing at the same or different flow rates. This embodiment allows simultaneous direct oxygenation of adherent cells 40 through transmembrane transport of oxygen across the membrane 30 while also providing additional direct oxygenation of the flowing biological liquid 11 through transmembrane transport of oxygen across the membrane 38.

Figure 6B:
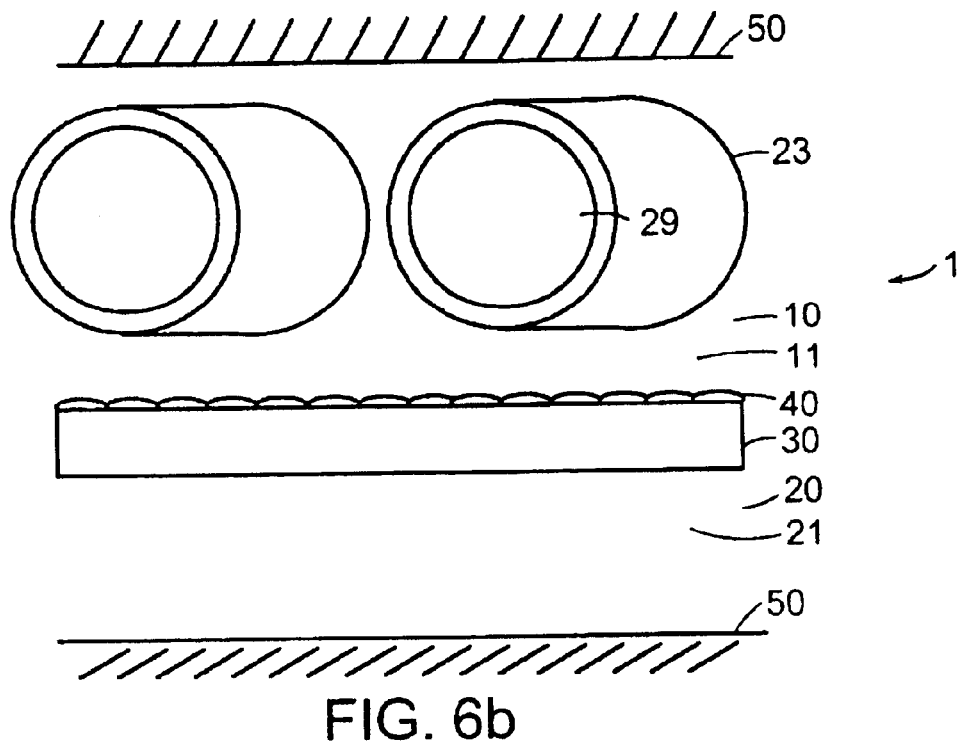

Another embodiment of the three-compartment cell culturing device featuring one liquid and two oxygenated fluid compartments is illustrated in FIG. 6b. One gas-permeable, liquid-impermeable membrane 30 is planar and seeded with cells 40 on its side facing the liquid compartment 10 and contacting the biological liquid 11. The second oxygenated fluid compartment 23 is formed by hollow fiber placed in a plane through the liquid compartment 10 and containing the oxygenated fluid 29. The oxygenated fluids 21 (contained in the oxygenated fluid compartment 20) and 29 may be the same or different, may be flowing in the same or different directions, and may be flowing at the same or different flow rates. This embodiment provides direct oxygenation of the flowing biological liquid 11 through transmembrane transport of oxygen across the hollow fibers 23 in addition to direct oxygenation of adherent cells 40 through transmembrane transport of oxygen across the membrane 30.

Figure 6C:
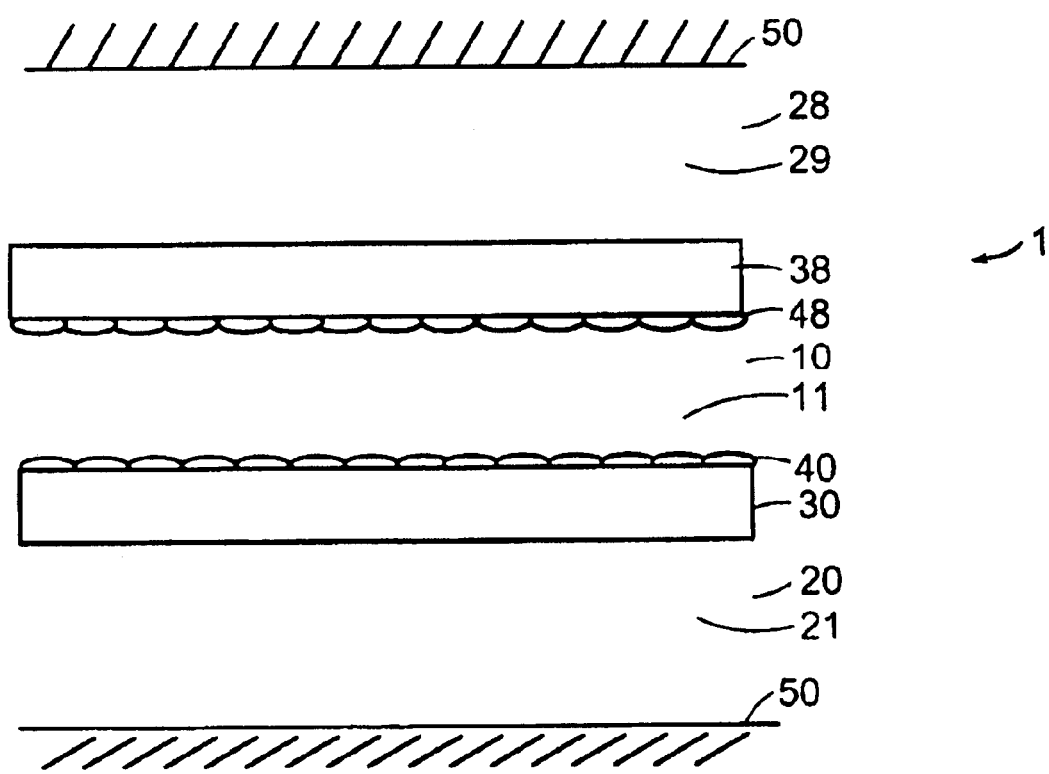

FIG. 6c illustrates a third embodiment of the three-compartment cell culturing device featuring one liquid and two oxygenated fluid compartments. This embodiment comprises one bioreactor unit in which the number of cells 40 contacting the flowing biological liquid 11 is increased by contacting the biological liquid with a second layer of cells 48 supported on the second gas-permeable, liquid-impermeable, substantially planar membrane 38. The directions of flow in oxygenated fluid compartment 20, oxygenated fluid compartment 28, and in the liquid compartment 10 may be the same lateral direction, contralateral, or perpendicular, or any combination thereof; one or both of the oxygenated fluids 21 and 29 may be static. The two layers of cells 40 and 48 may be at the same or different densities and may be the same or different types of cells. This embodiment allows increasing the treatment capacity of a single bioreactor unit without altering the number of cells per unit area of gas-permeable, liquid-impermeable membrane or changing the volume of biological liquid perfused through the system.

The cells 40 in the embodiments depicted in FIGS. 6a and 6c are substantially in contact with only one gas-permeable, liquid-impermeable membrane 30. The gap filled by the volume of the cells and the biological liquid 11 in the liquid compartment preferably is uniform in thickness but may be nonuniform. This gap is at least the height of the layer of cells 40 attached to the membrane 30, such that at least some biological liquid 11 intervenes between the cells and the face of the liquid-permeable membrane facing the cells. There is no absolute limit on the height of this gap for this invention. This gap may be maintained by a spacer.

Figure 7A:
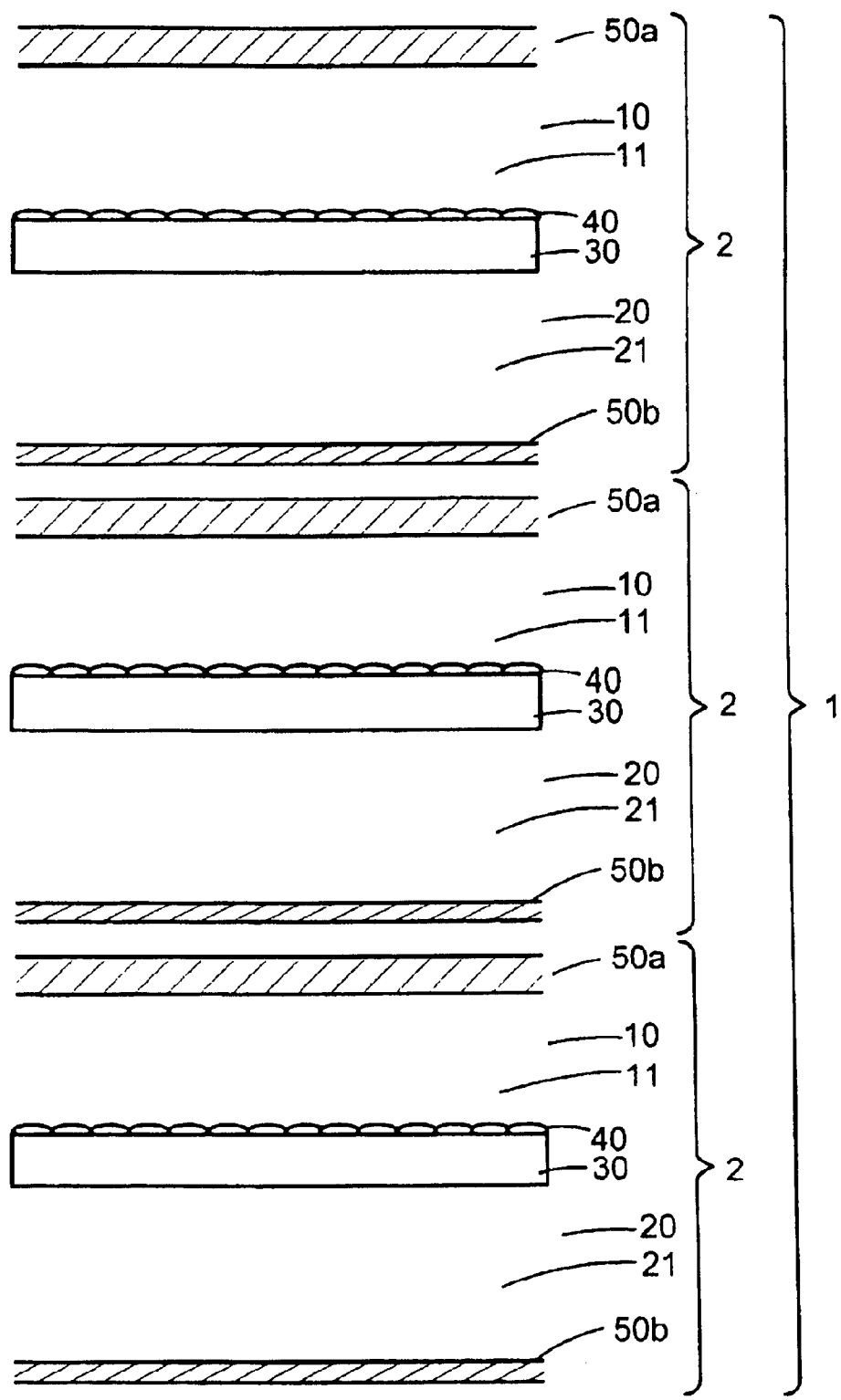
FIGS. 7a and 7b are schematic diagrams of embodiments of the cell culturing device comprising a plurality of stacked compartments.

One embodiment of a bioreactor comprising several stacked cartridges is shown in FIG. 7a, in which bioreactor 1 includes three stacked cartridges 2 (see also FIG. 1). Each cartridge 2 includes a housing including upper and lower walls 50a and 50b, respectively. Each cartridge includes a liquid compartment 10, through which the biological liquid 11 flows, and an oxygenated fluid compartment 20, through which the oxygenated fluid 21 flows. The two compartments of each cartridge or unit 2 are separated by a gas-permeable, liquid-impermeable membrane 30. The cells 40 are cultured on the membrane 30 on the side of the membrane facing the liquid compartment. The flow of oxygenated fluids and biological liquids can be in any direction: the same lateral direction, contralateral, or perpendicular, or any combination thereof. The number of compartments can vary up to 100 or more of each type of compartment. Further, the composition (e.g., percentage oxygen) and volumetric flow rates of the individual flows of oxygenated fluids 21 may be identical or differ among the oxygenated fluid compartments 20. Similarly, the composition (e.g., concentration of cytokines) and volumetric flow rates of the individual flows of biological liquid 11 may be identical or differ among the liquid compartments 10.

Figure 7B:
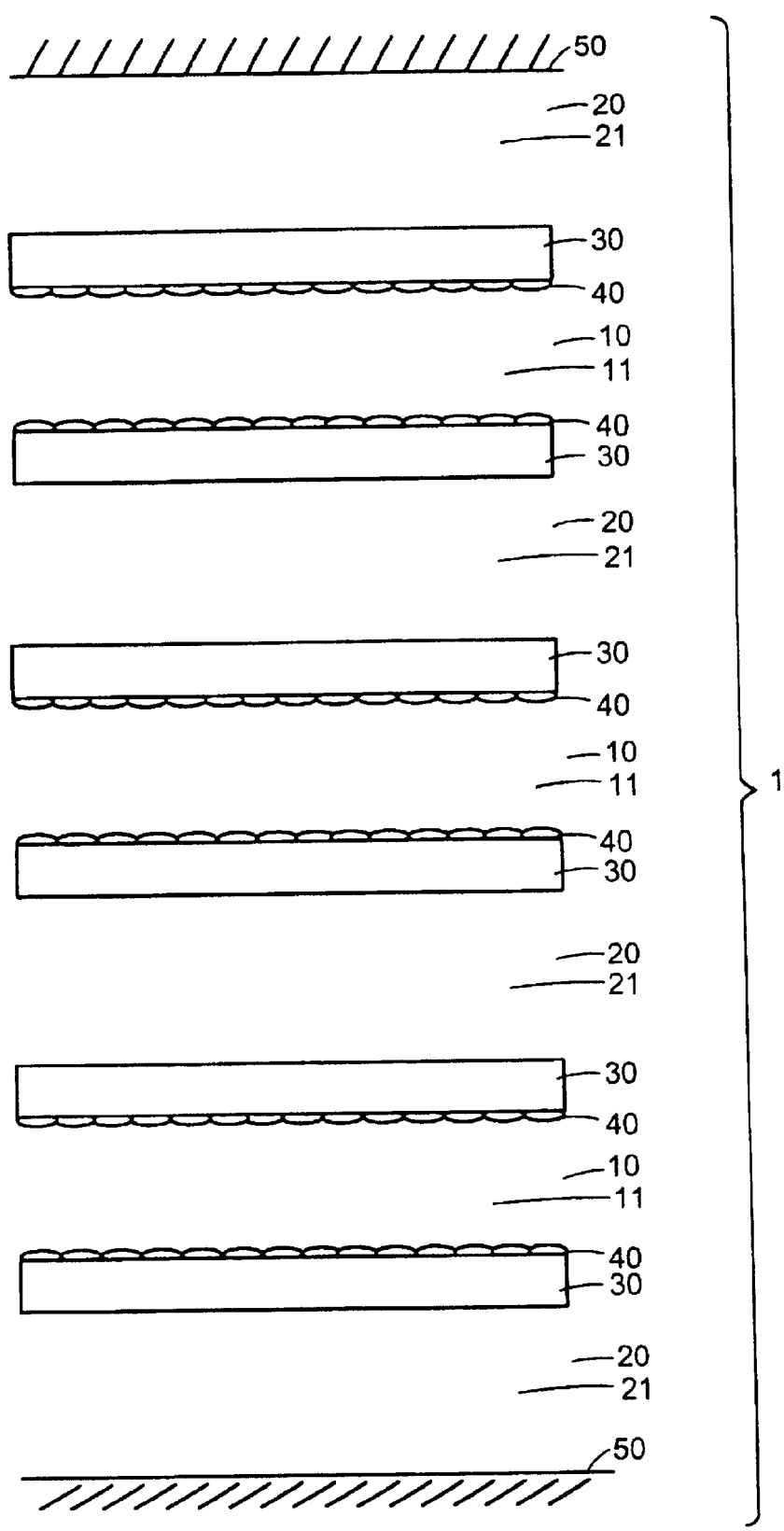

An alternative embodiment in which a bioreactor 1 comprises a plurality of stacked gas-permeable, liquid-impermeable membranes, with cells cultured on the side of the membrane facing towards a biological liquid and away from an oxygenated fluid, is shown in FIG. 7b. In this embodiment the bioreactor 1 comprises one large chamber having an inlet and an outlet for flow of the oxygenated fluid 21 through the bioreactor 1 and an inlet and an outlet for flow of the biological liquid 11 through the entire bioreactor 1. In this embodiment the bioreactor 1 does not contain individual cartridges but instead contains a plurality of stacked gas-permeable, liquid-impermeable membranes 30 (six in FIG. 7b), to create alternating cell compartments 10 (three in FIG. 7b) containing biological liquid 11 and oxygenated fluid compartments 20 (four in FIG. 7b) containing oxygenated fluid 21. Cells 40 are cultured on the side of each membrane 30 contacting the biological liquid 11. The number of compartments can vary up to 100 or more of each type of compartment. As indicated for the embodiment depicted in FIG. 7a, the compositions and flow of biological liquid 11 and oxygenated fluid 21 in each liquid and oxygenated fluid compartment, respectively, may be the same or different.

The inlet for oxygenated fluid to the bioreactor can be connected to a first manifold that distributes the flow of oxygenated fluid evenly or unevenly to each of the plurality of oxygenated fluid compartments to deliver oxygen and other gases to the oxygenated fluid compartments for gas exchange across the gas-permeable, liquid-impermeable membranes. After passage through the multiple oxygenated fluid compartments (in parallel), oxygenated fluid is collected in a second manifold common to all the oxygenated fluid compartments and then directed out of the bioreactor through an outlet for oxygenated fluid. Similarly, the inlet for biological liquid is connected to a manifold that distributes the flow of a biological liquid evenly to each of the plurality of liquid compartments to expose cells in the liquid compartments to the biological liquid. After passage through the multiple compartments (again, in parallel), the biological liquid is collected in a common manifold and is directed to an outlet to circulate in the flow loop for biological liquid.

The manifolds for this multi-compartment cell culturing device preferably are connected to their associated compartments by detachable connectors. These connectors allow easy installation and possible replacement of individual connections. Alternatively, the manifolds may be, if desired, permanently connected to each associated compartment.

Figure 8A:
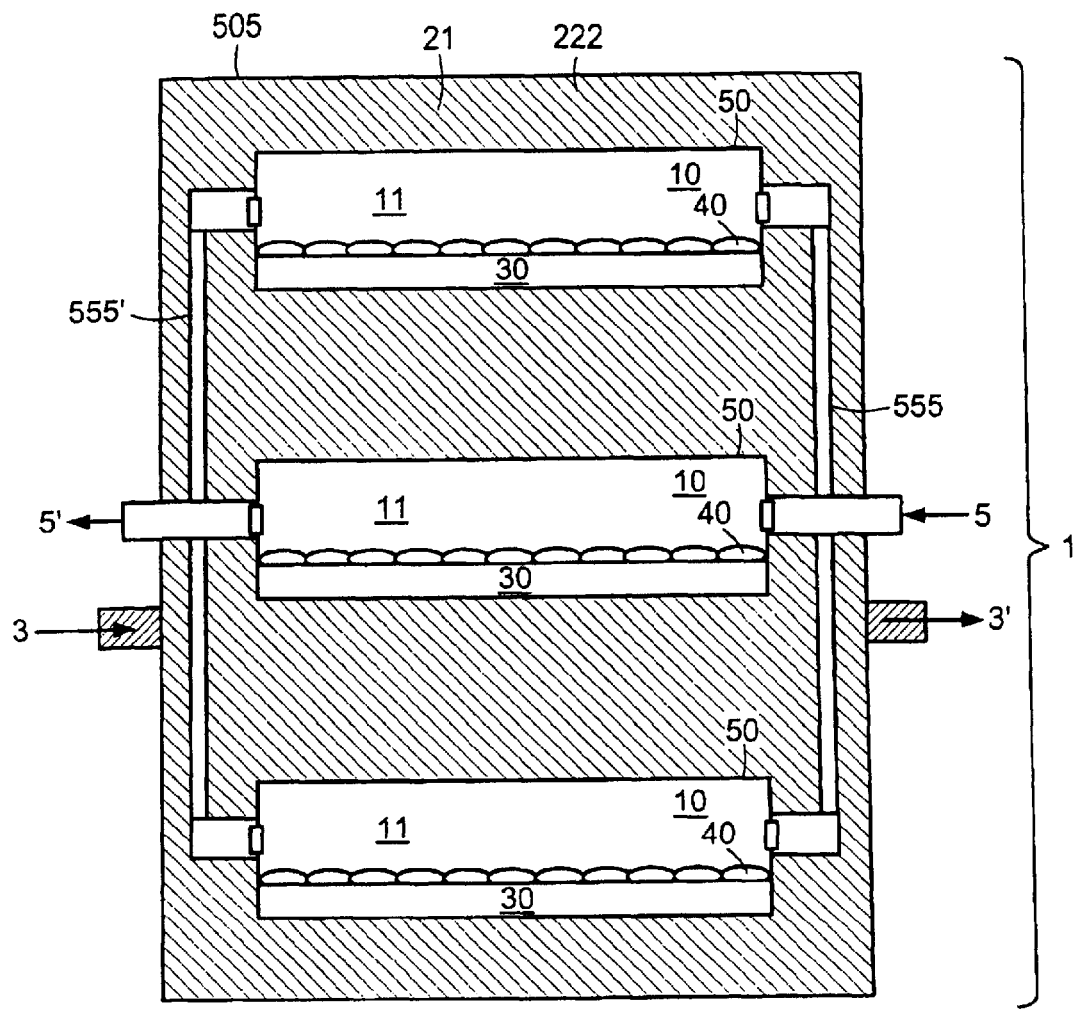
FIGS. 8a and 8b are schematic diagrams of embodiments of manifolding for a cell culturing device comprising a plurality of stacked "two-compartment" cell culturing chambers.

A specific embodiment of such a manifolded bioreactor 1 is shown in FIG. 8a, in which the bioreactor 1 has a plurality of stacked cartridges 2 (three in FIG. 8a), each comprising a liquid compartment 10, a gas-permeable, liquid-impermeable membrane 30, cells 40, and a rigid, impermeable housing 50. The bioreactor 1 also comprises a common oxygenated fluid compartment 222, oxygenated fluid inlet 3; oxygenated fluid outlet 3'; liquid inlet 5; liquid outlet 5'; liquid inlet manifold 555, and liquid outlet manifold 555'. Liquid inlet manifold 555 conducts biological liquid from liquid inlet 5 to the liquid compartment 10 of each cartridge 2. Liquid outlet manifold 555' conducts biological liquid to liquid outlet 5' from the liquid compartment 10 of each cartridge 2. The addition of other ports for each liquid compartment can serve as vents for air displacement during filling or as a means of draining each liquid compartment individually. Oxygenated fluid inlet 3 conducts oxygenated fluid into the common oxygenated fluid compartment 222 of the bioreactor 1 outside of the cartridges 2, where the oxygenated fluid contacts the gas-permeable, liquid-impermeable membrane 30. The oxygenated fluid is conducted out of the bioreactor vian oxygenated fluid outlet 3'. Other ports for venting oxygenated fluids may also be added to the impermeable wall 505 of the bioreactor 1. The number of compartments can vary up to 100 or more of each type of compartment.

Figure 8B:
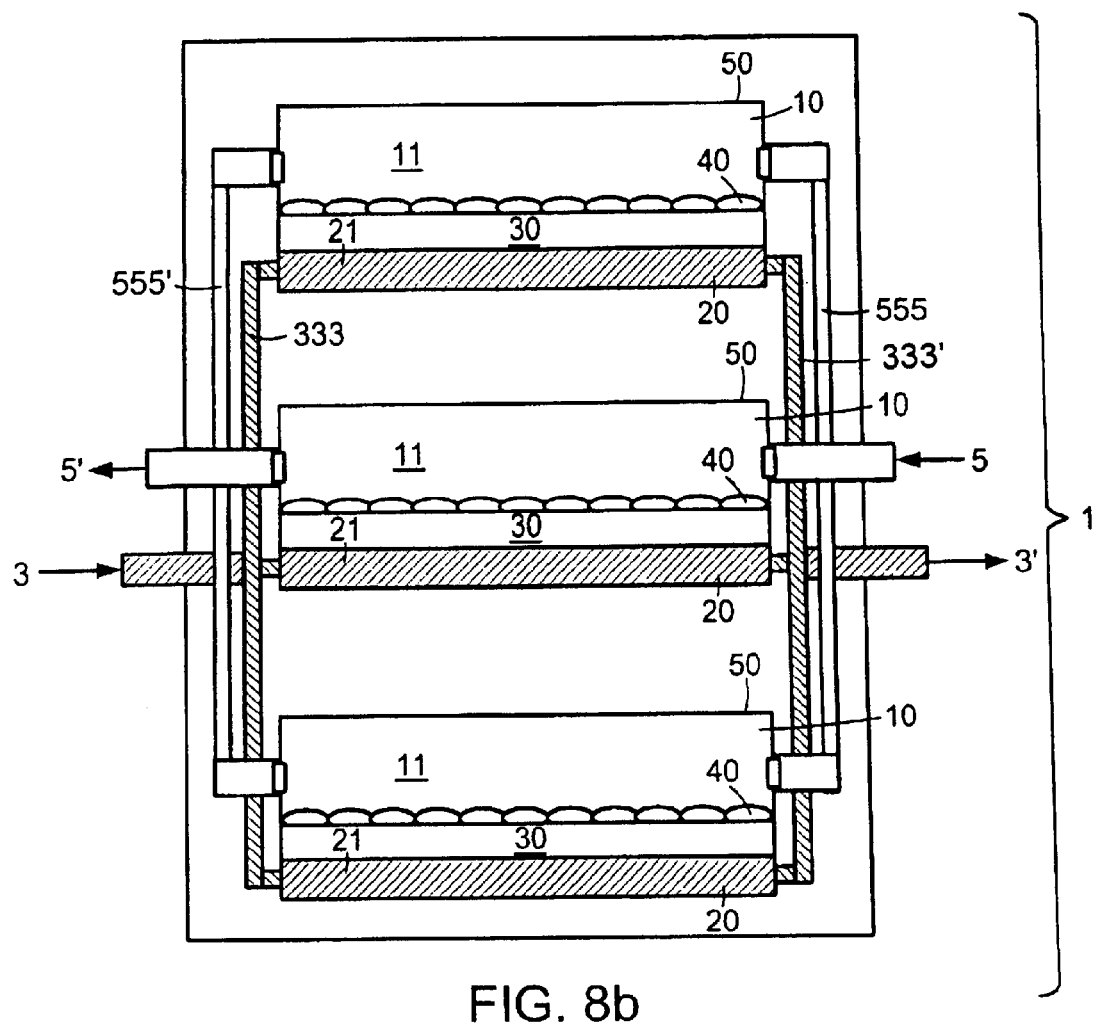

FIG. 8b shows an alternative configuration in which a bioreactor 1 has a plurality of stacked cartridges 2 (three in this figure), each comprising a liquid compartment 10; an oxygenated fluid compartment 20; a gas-permeable, liquid-impermeable membrane 30; cells 40; and a rigid, impermeable housing 50. The bioreactor 1 also comprises an oxygenated fluid inlet 3; oxygenated fluid outlet 3'; liquid inlet 5; liquid outlet 5'; liquid inlet manifold 555, and liquid outlet manifold 555'; oxygenated fluid inlet manifold 333; and oxygenated fluid outlet manifold 333'. Liquid inlet manifold 555 conducts biological liquid 11 from liquid inlet 5 to the liquid compartment 10 of each cartridge 2. Liquid outlet manifold 555' conducts biological liquid 11 to liquid outlet 5' from the liquid compartment 10 of each cartridge 2. The addition of other ports for each liquid compartment can serve as vents for air displacement during filling or as a means of draining each liquid compartment individually. Oxygenated fluid inlet manifold 333 conducts oxygenated fluids from oxygenated fluid inlet 3 to the oxygenated fluid compartment 20 of each cartridge 2. Oxygenated fluid outlet manifold 333' conducts oxygenated fluids to oxygenated fluid outlet 3' from the oxygenated fluid compartment 20 of each cartridge 2. Other ports for venting oxygenated fluids may also be added to each oxygenated fluid compartment 20. The number of compartments can vary up to 100 or more of each type of compartment.

In still another embodiment, the cells are separated from the flowing biological liquid by one or more intervening liquid-permeable membranes, such that the liquid compartment now becomes separate liquid-perfusion and cell compartments, which are either completely or incompletely divided by the one or more intervening liquid-permeable membranes. Any number of alternating compartments may be employed and are not bound by the chamber housing as shown in FIG. 7b. The chamber housing is made of impermeable material.

The bioreactor is seeded with functional cells; more preferably, the seeded cells function together to simulate the types and levels of function possible for cells in an organ. Cells can either grow in the bioreactor, remain stable in number, or switch between modes of growth and numerical stability. Cells also can either maintain their previous phenotype or change phenotype upon culture in the bioreactor. The bioreactor is to be used as an in vitro culture system and its oxygenated fluid and liquid circuits make it suitable for use as an organ assist device to treat a patient in need of organ assistance. The device is seeded with organ cells that are cultured to function similarly as in the organ from which the cells were derived.

One source of cells for the bioreactor is a mammalian organ. When this organ is the liver, the cells that are cultured for use in a liver assist device comprise hepatocytes, the principal cells of the liver which are capable of fulfilling the functional requirements typically associated with the liver when placed in an appropriate chemical and structural environment. Other cells present in liver may also be included in the device, such as endothelial cells; Ito cells; Kupfer cells, a specialized macrophage-like cell; and fibroblasts. A co-culture of hepatocytes with one or more of these or other types of cells may be desirable in a LAD. For bioreactors comprising a plurality of units each unit may be seeded with the same numbers of cells and/or combinations of types of cells or different numbers and/or combinations.

Given the limited availability of human hepatocytes, non-human sources can be used in the invention. Cells from other mammals including, but not limited to, equine, canine, porcine, bovine, ovine, and murine sources can be used. Cell donors can vary in development and age, sex, species, weight, and size. Cells may be derived from donor tissues of embryos, neonates, or older individuals including adults. Embryonic progenitor cells such as parenchymal or mesenchymal stem cells can be used in the invention and induced to differentiate to develop into the desired tissue. In addition, mixtures of cells from different cell strains, mixtures of normal and genetically modified cells, or mixtures of cells from two or more species or tissue sources may be used.

One source of hepatocytes for use in the invention is porcine liver. The best current estimates of the number of viable hepatocytes for each clinical LAD is approximately $10^{10}$ cells, roughly the number of cells from a small (20 lb.) pig liver. An alternative source of cells is by culturing either cells previously obtained from a mammalian organ or by culturing cells that have been previously cultured such that they exist as a cell line. Cells for use in the invention may be normal or genetically engineered by spontaneous, chemical, or viral transfection. Recombinant or genetically engineered cells can be created for immortality, reduced allogenicity, or differentiated hepatocyte function. Procedures for genetically engineering cells are generally known in the art, and are described in Sambrook et al., Molecular Cloning, A Laboratory Manual, Cold Spring Harbor Press, Cold Spring Harbor, N.Y. (1989).

Cells are seeded from fresh, processed tissue, from cells cultured previously in vitro, thawed from cryopreserved tissue, or some combination thereof. Prior to seeding cells are suspended in a seeding medium. In the new methods and devices the cells are seeded onto the gas-permeable, liquid-impermeable membrane. Prior to seeding cells the gas-permeable, liquid-impermeable membrane is treated, if desired, and the liquid compartment drained of most but not necessarily all of its liquid contents. It also is possible to replace some of the liquid contents with, e.g., a biological liquid, prior to seeding cells. These transfers of liquid may be conducted either by draining through one or more of the ports for the liquid compartment, by removing the impermeable wall contacting the liquid compartment and dispensing and aspirating liquid directly into the liquid compartment through the opening created by the removal of the above-mentioned impermeable wall, or a combination thereof.

Multiple embodiments are possible for seeding of cells. In one embodiment the cells are introduced by first removing the impermeable wall contacting the liquid compartment and dispensing (with a manual or automated pipette) cells, in a liquid suspension or suspended in a natural or synthetic polymer matrix, onto the gas-permeable, liquid-impermeable membrane. In an alternative embodiment cells are introduced by first making sure at least two ports for the liquid compartment are opened and then allowing the suspension of cells to flow into the liquid compartment. For either of these embodiments the cells are allowed to attach and establish functionality on the membrane. The seeding medium then may be drained (by any of the methods described in the above paragraph for removal and addition of liquids from the liquid compartment) and replenished with a biological liquid.

For a bioreactor containing a plurality of culture units or cartridges, each unit or cartridge may be seeded with cells either together with the other units in the assembled state by one of the above embodiments or seeded with cells separately as individual units not bundled together with manifolds and then subsequently manifolded together into a complete bioreactor system. The time at which seeded units are assembled together in this latter embodiment may be soon after seeding or after allowing further establishment of cultures.

Once cultures have become established and the bioreactor is functional as a liver assist device, it is used to treat a patient in need of liver assistance, as shown in FIG. 1. As shown in FIG. 1 and as described herein, the liver assist device of the invention comprises a bioreactor 1 having an inlet 3 and an outlet 3' for the supply of oxygenated fluid and an inlet 5 and an outlet 5' for the supply of biological liquid. The inlet 3 for the supply of oxygenated fluid to the oxygenated fluid compartments is fed by an oxygenated fluid supply 4. The oxygenated fluid outlet 3' is preferably vented to the atmosphere or a collection vessel. Also associated with the oxygenated fluid supply 4 are controllers to monitor the oxygenated fluid mixture, pressure, and flow rates (not shown).

The inlet 5 and outlet 5' for the biological liquid are connected in a closed loop. It is desirable, but not necessary, to have in the loop for the biological liquid an immunoisolation unit 7 to isolate the blood flow of the patient from the bioreactor. The bioreactor 1 may be associated with a plasmapheresis unit 8 to separate the treated patient's plasma from blood to make blood detoxification more efficient. Within the flow of the biological liquid are various pumps 6, 6', and 6" to ensure the flow of medium or biological liquid through the bioreactor and the immunoisolation unit and pH, temperature, and flow sensors (not shown).

EXAMPLES

The invention is further described in the following examples, which do not limit the scope of the invention described in the claims.

Examples 1, 2, and 14 describe new cell culturing devices. Examples 3 through 8 describe assays used to measure hepatocellular function. Examples 9 through 14 demonstrate certain embodiments of the invention.

Example 1

Cell Culture Device—Static Arrangement

Figure 9A:
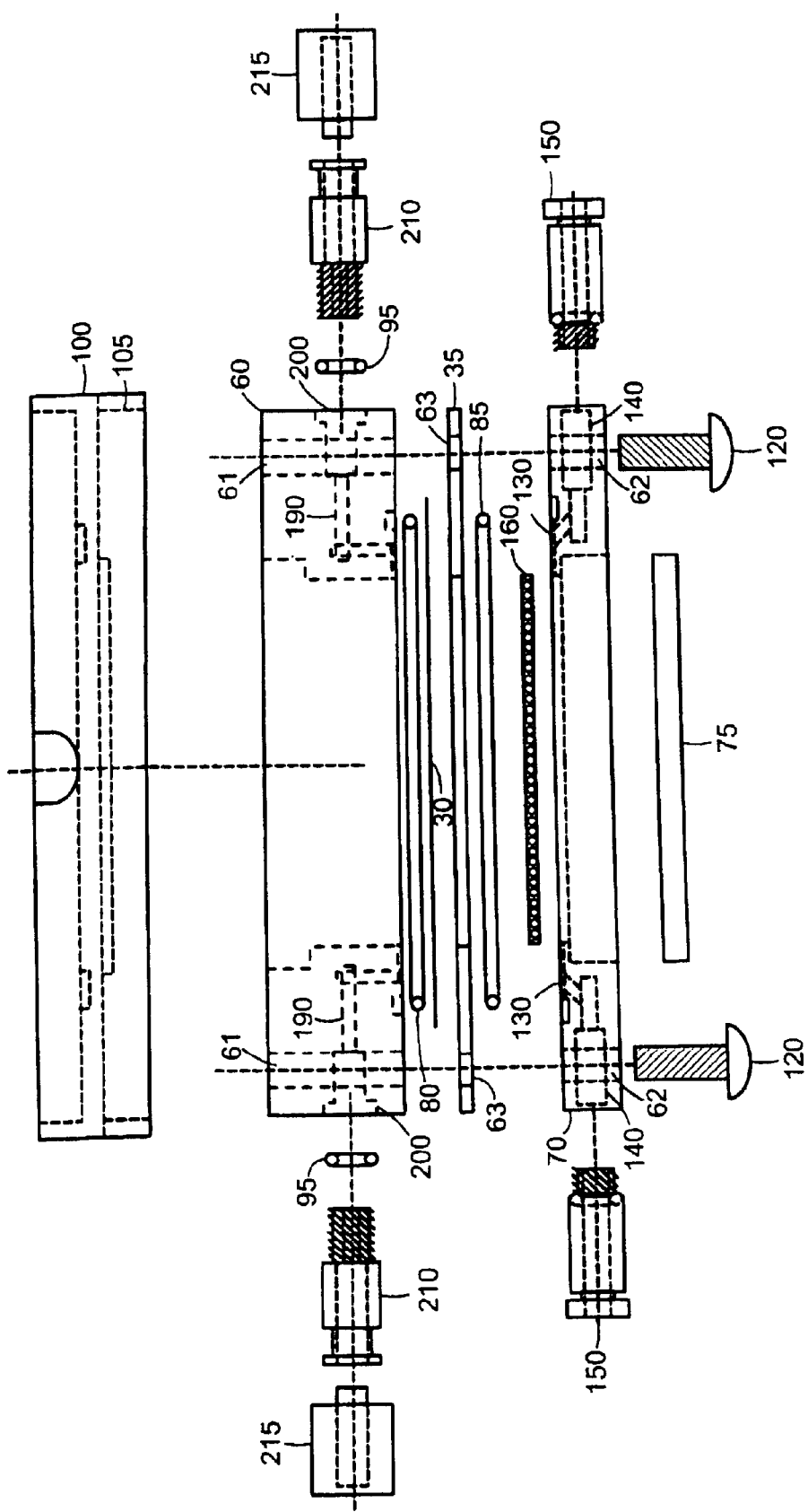
FIGS. 9a and 9b are schematic diagrams of side views of cell culture devices.
Figure 9B:
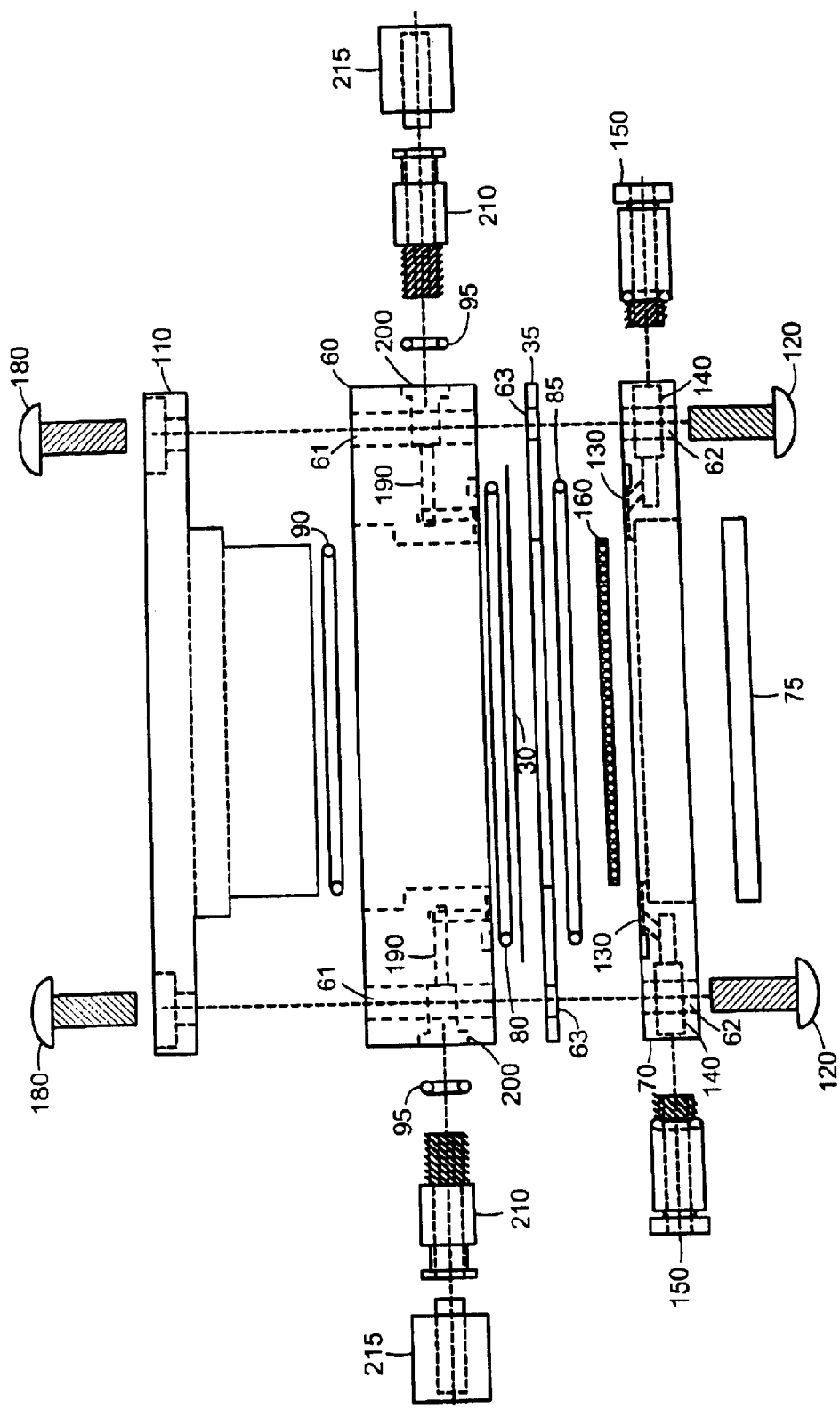

The ability of the new cell culturing device to support the function of hepatocytes in vitro was evaluated by constructing a laboratory-scale device 1 based on this configuration. The device, as depicted in FIGS. 9a and 9b, comprised an assembly of upper 60 and lower 70 housings, a gas-permeable, liquid-impermeable membrane 30, a frame 35, a window 75 for the lower housing, a set of O-rings 80, 85, 90, and 95, a cover 100, a cap 110, and ancillary screws and fittings 120, 150, 180, 210, and 215. The membrane used typically was either Polyflex® (Plastics Suppliers, Inc., Columbus, Ohio), a 0.002"-thick film of polystyrene, or TYVEK® 1073 (E.I. du Pont de Nemours and Co, Inc., Wilmington, Del.), a microporous non-woven membrane composed of USP Class VI polyolefin, although other materials were also used in some studies. The membrane was epoxied onto one face of the frame 35, a 0.0625"-thick aluminum annulus with an axisymmetric 2.122"-diameter through-hole, to form a membrane/frame assembly 400 prior to use.

A set of four symmetrically-spaced stainless steel #10-32×½" truss-headed screws 120 bolted the opposing 4"-diameter upper 60 (0.750"-thick) and lower 70 (0.315"-thick) polycarbonate housings together to sandwich the membrane/frame assembly 400, with the membrane/assembly oriented with the membrane 30 facing the upper housing. Through-holes 63 in the frame 35 allowed insertion of the screws 120. through counter-bored clearance holes 62 in the lower housing 70 into tapped holes in the upper housing 60. A liquid-tight seal was formed between the upper face of the membrane/frame assembly and the lower face of the upper housing using a #039 O-ring 80 seated in an axisymmetric groove in the upper housing. Similarly, a gas-tight seal was formed between the lower face of the membrane/frame assembly and the upper face of the lower housing using a second #039 O-ring 85 seated in an axisymmetric groove in the lower housing. With these components the minimum diameter of the membrane was 2.9" to match the outer diameter of the O-rings, although membranes with larger diameters could be used by cutting away sections of the membrane to prevent interference with the path of the screws.

An axisymmetric 2.125"-diameter, 0.062"-deep chamber 30 for gas beneath the membrane was formed by securing a 2.330"-diameter, 0.125"-thick polycarbonate window 75 into an axisymmetric thru-hole in the lower housing 70. Two channels 130 connected to tapped holes 140 fitted with #10-32×⅛" tube OD Legris fittings with integral O-rings to provide ports for external access to this chamber. Additional mechanical support of the membrane could be provided by placing in this chamber a highly porous 2.0"-diameter, 0.06"-thick block 160.

Two methods were used to form a 2.125"-diameter chamber 10 holding liquid 11 bathing cells 40 attached to the membrane 30 in an axisymmetric 2.125"-diameter thru-hole in the upper housing 60. In one method (depicted in FIG. 9a) a 0.750"-deep chamber 170, used when seeding cells onto the membrane, was formed by placement of a 4.216"-diameter polycarbonate cover 100 onto the upper face of the upper housing. This cover, which was intended to allow aseptic transportation of the assembled device after seeding with cells and stacking of multiple devices, had 0.25"-high rims 105 along the perimeter of both its upper and lower faces to prevent spillage of liquid out of the chamber and penetration of external contaminants into the chamber.

In the second method (depicted in FIG. 9b) a 0.062"-deep chamber 10, used after removal of the liquid containing the suspension for seeding cells, was formed by securing a 4.000"-diameter polycarbonate cap 110 into the through-hole in the upper housing 60. A liquid-tight seal between the cap and upper housing was formed using a #020 O-ring 90 and four symmetrically spaced stainless steel #10-32×½" truss-headed screws 180 which fastened into tapped holes on the upper face of the upper housing. Two channels 190 connected to tapped holes 200, fitted with #10-32×¼" 316 stainless steel female luer-lock fittings 210 with #006 O-rings 95, provided ports for external access to these chambers. These ports were plugged for static cultures using 316 stainless steel male luer-lock plugs 215.

All assembly steps, unless otherwise noted, were conducted in a biological safety cabinet and occurred after sterilizing all parts (other than the membrane/frame assembly 400 and the fittings 150 for the lower housing 110) by autoclaving or other proven treatment (e.g., gamma irradiation or exposure to an oxidizing gas such as ethylene oxide, peracetic acid, and/or hydrogen peroxide). All materials were handled with either sterile tweezers or gloves within the cabinet. Some membranes were used without sterilization for relatively short durations of a 1–3 days or less; other membranes were either epoxied onto frames and gamma irradiated prior to installation (e.g., Polyflex®) or gamma irradiated without frames prior to installation (e.g., TYVEK® 1073).

The initial steps in assembly consisted of mating the upper 60 and lower 70 housings, the #039 O-rings 80 and 85, the membrane/frame assembly 400, the threaded fittings 150 and 210, and the #006 O-rings 95 and tightening the four screws 120 holding these parts together. Next, the fittings were tightened and plugs 215 for the fittings for the upper housing affixed. The cover 100 then was installed and the device 1 stored under aseptic conditions until use.

Primary hepatocytes 40 in complete medium (Williams E medium supplemented with 4.5 g/L glucose, 0.5 U/mL bovine insulin, 7 ng/mL glucagon, 7.5 µg/mL hydrocortisone, 10 mM HEPES, 20 ng/mL EGF, 20 mM glutamine, 10 IU penicillin, and 10 µg streptomycin) with 1% new-born calf serum (NBCS) were obtained from porcine donors with the following procedure.

Hepatocytes were isolated from livers of Yorkshire/Hampshire crossbred pigs, obtained from E M Parsons (Hadley, Mass.), weighing 8.3+3.0 kg. Heparin (Elkins-Sinn, Cherry Hill, N.J.) was administered intravenously at 0.5 mg/kg and donors anesthetized with a mixture of Telazol (7–10 mg/kg, Fort Dodge Laboratories, Fort Dodge, La.) and Rompun (5 mg/kg, Miles, Inc., Shawnee, Mission, Kans.). Plane of anesthesia was maintained with isoflurane gas. All procedures were performed in compliance with ACUC guidelines.

Cells 40 were isolated using a modification of the Seglen method which has been described previously (P Selgen, Preparation of isolated rate liver cells, In Method in Cell Biology (D M Prescott, et al.), Vol. 13, Academic Press (New York, N.Y.), 1976). Briefly, the exposed liver was cannulated and perfused in situ with cold Lactated Ringers (Baxter, Deerfield, Ill.) at 20 mL/min before excision. The liver was quickly warmed and perfused with 0.2% EDTA at 37° C. This was followed by perfusion of 1 mg/mL collegians (Life Technologies, Grand Island, N.Y.) at 37° C. until digestion appeared complete (mean digestion 22+4 min). Further digestion was stopped with the addition of cold Hank's buffered saline solution (BioWhittaker, Walkerville, Md.) supplemented with 10% NBCS (Cyclone, Logan Utah). Undigested tissue and gall balder were excised and the remainder of the tissue passed sequentially through 200 and 100 micron stainless steel sieves (Fisher Scientific, Pittsburgh, Pa.), respectively. The cell suspension was washed twice and the cell pellet resuspended in culture media. Viability was determined by Trypan blue exclusion.

The cells were then seeded onto the membrane. In some studies the membrane 30 was pre-coated with a sterile 4 mL volume solution of 40 µg/mL Type I collagen in water for 45 minutes, followed by aspiration of this solution and rinsing with an equal volume of sterile phosphate-buffered saline (PBS), prior to seeding of cells. A suspension of cells in medium 11 was evenly suspended by swirling the receiver containing the cells and triturating the suspension multiple times with a sterile pipette prior to seeding. For most studies cells were seeded at an initial density of 2×106 cells per device 1. In some studies, however, higher densities were examined (see Example 13). The cover 100 to the device 1 was removed, 4 mL of the cell suspension pipetted onto the membrane 30, the device agitated carefully to distribute the liquid evenly onto the surface of the membrane, and the cover replaced. The cell-seeded device was transferred to an incubator (held at 37° C. and 85% relative humidity) where the gas chamber 20 was connected, through one of the ports 150 in the lower housing 70, to a gas tank 4 supplying 10% $CO_2$ and a concentration of oxygen ranging from 0 to 90% at 2–5 psi and no greater than 1.0 mL/min.

After approximately 18–24 hours the device was removed from the incubator, placed back in the biological safety cabinet, cover 100 removed, and the medium 11 aspirated using a sterile Pasteur pipette. The cap 110 with associated #020 O-ring 90 then was placed onto the thru-hole in the upper housing 60 and secured in place using the four screws 180. Approximately 2.7 mL of fresh medium 11 was introduced into the liquid chamber 10 by removing the luer-lock plugs 215, transferring in medium at a rate of 1.5 mL/min with the ports oriented vertically (such that all air bubbles were removed from the chamber), and closing the ports by reinstalling the luer-lock plugs. The device then was transferred back to the incubator and reconnected as above to the oxygenated fluid supply 4. Devices were sampled subsequently by disconnection of the oxygenated fluid supply, transfer from the incubator to a biological safety cabinet, removal of the luer-lock plugs, and draining of the liquid contents into a small collection vial. This procedure resulted in a device 1 that allowed culture of cells 40 on the membrane 30 with direct transmembrane oxygenation and independent perfusion.

Example 2
Cell Culture Device—Perfused Arrangement

Figure 10A:
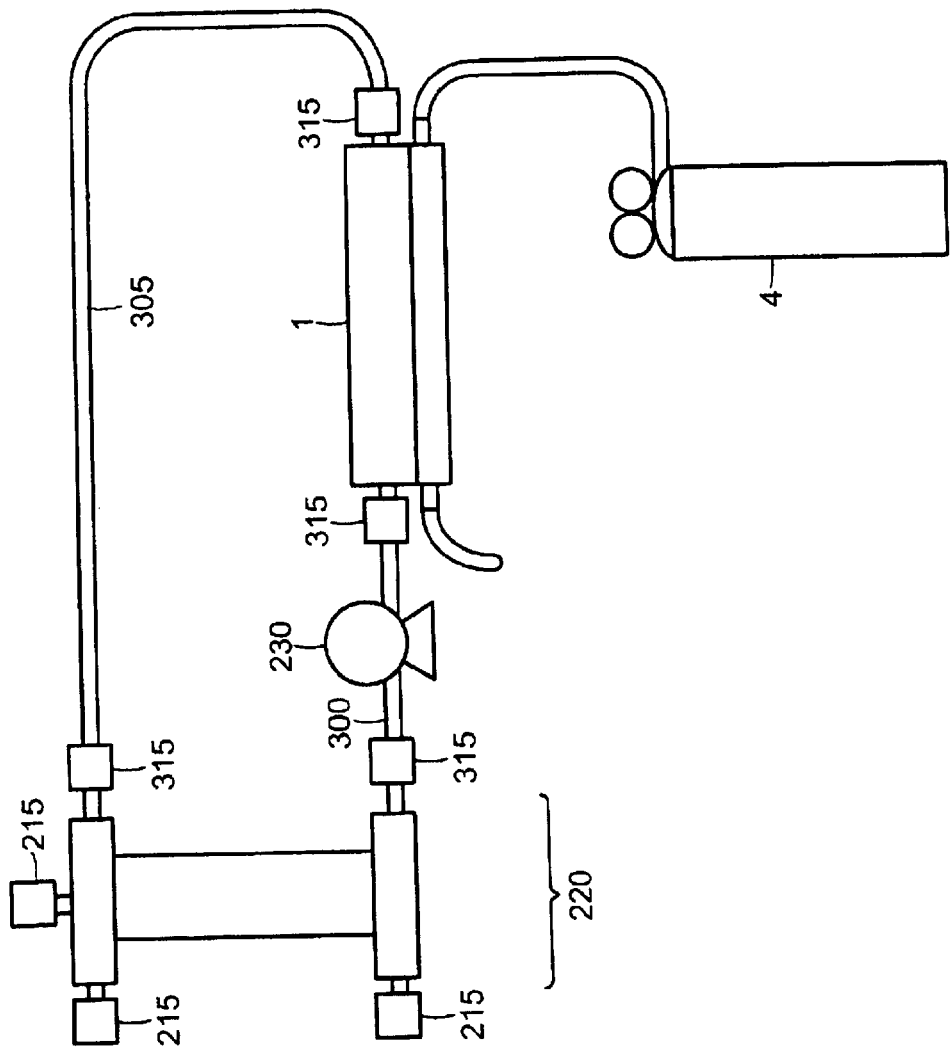
FIGS. 10a and 10b are schematic diagrams of the components of a perfusion circuit for cell culture devices.
Figure 10B:
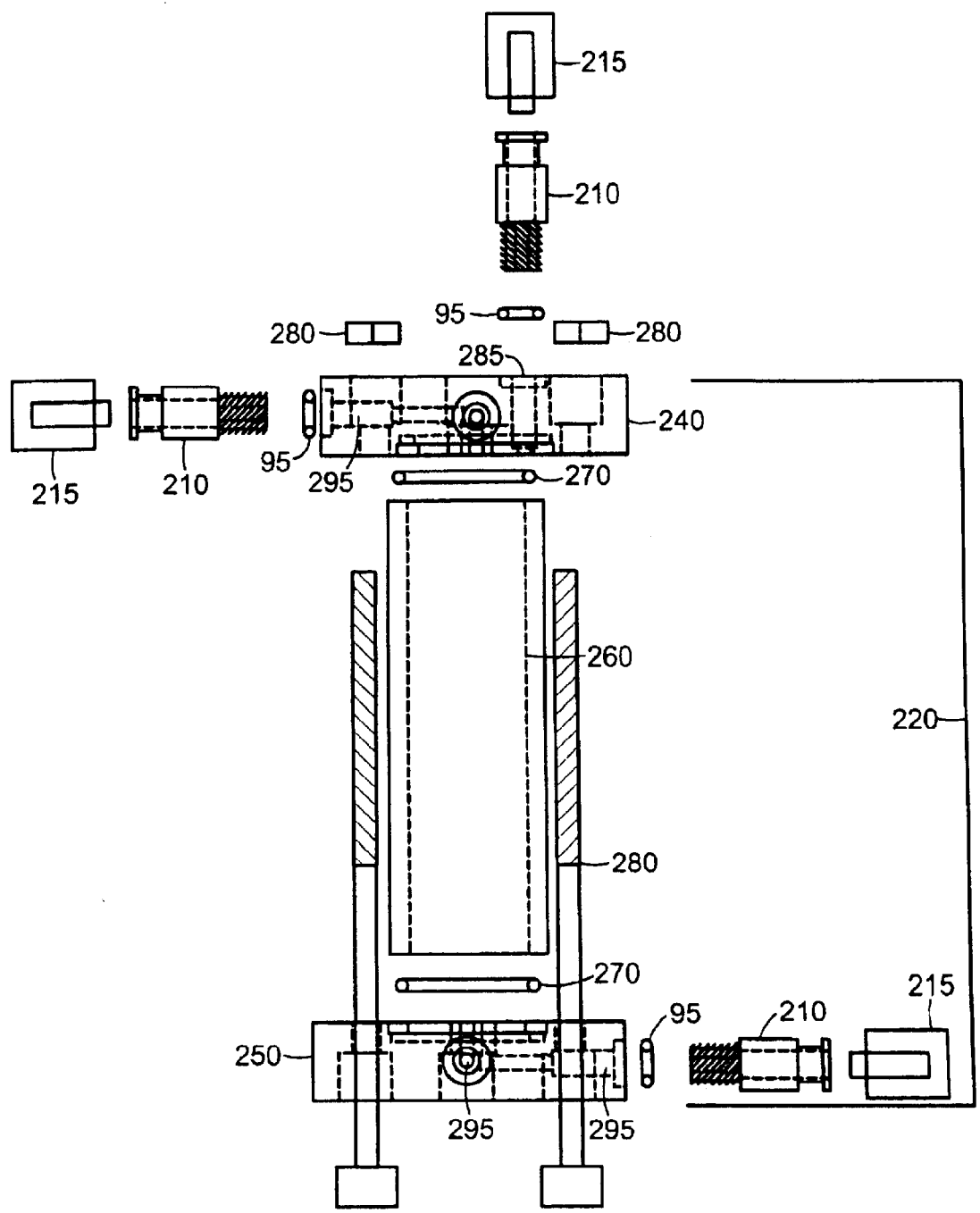

The apparatus of Example 1 also was adapted to study the function of hepatocytes in vitro under closed-loop perfusion of medium. The apparatus was assembled and handled as described in Example 1 through installation of the cap 110. A simple flow circuit, as depicted in FIGS. 10a and 10b, was assembled aseptically to the device in a biological safety cabinet. Components for this circuit (illustrated schematically in FIG. 5a) comprised a cell-seeded device 1 (with installed cap 110 as described in Example 1), a reservoir 220, a pump 230, connecting tubings 300 and 305, and luer-lock fittings 215 and 315. All components were sterilized by autoclaving (or equivalent treatment) prior to assembly except the cell-seeded device (which had been handled aseptically). Prior to connecting the cell-seeded device the male luer-lock plugs 215 were removed from the luer-lock fittings 210.

FIG. 10b depicts the reservoir, which functioned also as a bubble trap, comprising a polycarbonate top 240 and bottom 250 (each 2.00" in diameter and 0.500" thick), a 3.00"-tall×0.75"-ID×1.00"-OD polycarbonate tube 260, a pair of #019 O-rings 270, 3 metal screws and bolts 280, and 5 #10-32×¼" 316 stainless steel female luer-lock fittings 210 with #006 O-rings 95. The O-rings 270 sat in 0.785"-ID× 0.965"-OD×0.052"-deep axisymmetric grooves at the bottom of 0.75"-ID×1.00"-OD×0.062"-deep recesses (to align the tube) in the upper and lower faces of the bottom and top, respectively. Liquid-tight seals were formed between the tube and top and bottom, respectively, by seating the tube in these grooves after installation of the O-rings 270 and tightening of the 3 symmetrically spaced screws and bolts 260. Pairs of luer-lock fittings 290 were installed in tapped holes 295 on the circumference of the bottom and top. A fifth luer-lock fitting 210 was installed in a tapped hole 285 on the upper face of the top.

A closed-loop circuit for perfusion was formed by establishing two sets of connections using approximately 18"-long Tygon LFL L/S size #13 tubing (300 and 305, respectively) with male luer-lock×¹⁄₁₆"-ID barbed 316 stainless steel fittings 315 on both ends. One length of tubing 300 connected one of the luer-lock fittings 210 on the bottom of the reservoir 220 to one of the luer-lock fittings 210 on the cell-seeded device 1; this tubing functioned as a flow passage to introduce flowing medium 11 into the cell-seeded device. A second length of tubing 305 connected one of the luer-lock fittings 210 on the top of the reservoir to the remaining luer-lock fitting 210 on the cell-seeded device; this tubing functioned as a flow passage to remove medium from the cell-seeded device. A 316 stainless steel luer-lock plug 215 was installed on the remaining fitting on the bottom of the reservoir. This plug was removed when medium in the reservoir was sampled or the reservoir was drained.

A volume of perfusate 11, typically ranging from 10–20 mL, then was added to the reservoir 220 through the luer-lock fitting 210 on the upper face of the top 240 of the reservoir. During this addition the unconnected luer-lock fittings 210 on the circumference of the top of the reservoir were unplugged to allow venting. Luer-lock plugs 215 then were installed on the remaining luer-lock fittings 210 prior to transfer of the assembled circuit from the biological safety cabinet to the incubator. In the incubator the tubing 300 was loaded into the head of a pump 230 (typically a peristaltic pump comprising a Cole-Parmer Easy-Load pump head with PSF housing and Cole-Parmer stainless steel rotor regulated by a Cole-Parmer controller). The device 1 was reconnected to the oxygenated fluid supply 4 as described in Example 1. The pump then was powered to the desired volumetric flow rate (ranging between 0 and 12 mL/min but typically 0.1–1.5 mL/min), and the liquid 11 in the reservoir recirculated through the tubing 300 and pump head, into the cell-seeded device 1, through the tubing 305, and back into the reservoir. During this procedure the device may be tilted to facilitate removal of air bubbles.

Two methods of further operation of the perfusion circuit were implemented. In one method (Perfusion Method I) the medium 11 was completely exchanged for fresh medium after every 24–72 hours of operation; in the second method (Perfusion Method II) the medium was never exchanged but rather was introduced initially as a large enough volume to support the cells for a period of one to many days. For Perfusion Method I the pump 230 first was stopped, the oxygenated fluid supply 4 disconnected, and the perfusion circuit transferred into a biological safety cabinet. The medium remaining in the reservoir 220 was drained by removing the luer-lock plug 215 from the luer-lock fitting 210 on the bottom 250 of the reservoir not connected to the tubing 300 and then tilting the reservoir. The circuit then was reconfigured temporarily by detaching the tubing 305 from the luer-lock fitting 210 on the top 240 of the reservoir. After removing the luer-lock plug 215 from the luer-lock fitting on the top face of the top of the reservoir, the reservoir was refilled with the volume of medium added initially and the pump restarted. The pump was operated in this open-loop configuration for a period of time equal to the ratio of the volume retained after draining the circuit (calculated as the difference between the volume added initially and the volume drained) to the volumetric flow rate. The pump then was stopped and the circuit reconfigured to the original closed-loop configuration prior to transfer back to the incubator, reconnection to the oxygenated fluid supply, and restarting of the pump.

For Perfusion Method II the pump 230 was stopped, the oxygenated fluid supply 4 disconnected, the tubing 300 unloaded from the pump, and the perfusion circuit without the pump returned to the biological safety cabinet without emptying the device of liquid. A 750 μL sample was removed with a sterile pipette from the port 210 for sampling on the reservoir 220 (after unplugging the luer-lock plug 215 for the port for venting). The perfusion circuit then was returned to the incubator, the appropriate section of tubing reinstalled into the pump head, pump turned on, and oxygenated fluid supply reconnected to the device.

Although the above perfusion circuit had a closed-loop configuration, we anticipate forms of the embodiment described in this Example 2 with an open-loop configuration in which the flow path is from a supply reservoir, through a pump, through the device, and into a collection reservoir. Assembly and operation of this open-loop circuit follows the general procedures described above.

The procedures and operations described above resulted in a device that was operated for in vitro studies in a manner simulating the use of a LAD for extracorporeal treatment of human and animal subjects experiencing compromised liver function.

Example 3
Hepatocellular Detoxification Activity Based on Conversion of Alkoxyresorufin to Resorufin Cytochrome P450 (CYP450) isozymes are Phase I mixed-function monooxygenases which, along with complementary Phase II conjugative enzymes, catalyze the biotransformation of xenobiotics as well as endogenous lipophiles into soluble compounds more easily cleared by the renal system. As monooxygenases the function of CYP450 isozymes requires the presence of molecular oxygen. Accordingly, the activity of CYP450 isozymes is believed to depend on the availability of oxygen.

The O-dealkylation of non-fluorescent alkoxyresorufin ethers to fluorescent resorufin offers a tool for investigating the activities of CYP450 isozymes. For example, the dealkylation of the phenoxazone ethers benzyloxyresorufin (BROD) and ethoxyresorufin (EROD) has allowed researchers to study the activity of the individual isozymes CYP IIB2 and IA1, respectively. To measure CYP450 activity in static cultures, standard complete medium 11 with 1% NBCS was replaced in the cell-seeded device 1 from Example 1 with complete medium lacking serum but containing 5 μM of BROD or EROD (Molecular Probes, Eugene, Oreg.) and 80 μM of dicumarol (Sigma Chemical Co., St. Louis, Mo.). Dicumarol was included in the incubation to limit cytosolic degradation of resorufin, the product of the dealkylation of alkoxyresorufin by CYP450 isozymes, by subsequent Phase II reactions.

Samples were collected after incubation for 3 hours and analyzed in a Turner 450 fluorimeter at excitation and emission wavelengths of 540 nm and 585 nm, respectively. Data were collated as stimulation indices (ratios of fluorescence in samples after biotransformation for three hours to fluorescence in aliquots of equal volume prior to addition to the cell-seeded device 1). Data were expressed as ratios of the stimulation index for a device containing a gas-permeable cell culture support being tested to the stimulation index for cells from the same donor and day post seeding but seeded into equivalently-sized 60 mm-diameter tissue-culture dishes. This assay typically was performed on the first day post seeding of cells but also was occasionally performed up to seven or more days post seeding.

In this assay, conversion of alkoxyresorufin to resorufin corresponds to an increase in fluorescence, such that the stimulation index and detoxification activity correspond to the level of P450 activity of a particular set of isozymes and intensity of the detoxification response of cultured hepatocytes.

Example 4
Activity of Hepatocellular P450 Isozymes Based on Clearance of Diazepam Metabolism of the drug diazepam provided an alternative method to evaluate the activity of P450 isozymes in hepatocytes supported in device 1 of Example 1. The clearance of diazepam and its biotransformation to nordiazepam and temazepam were evaluated using a method similar to that of Jauregui et al. (H O Jauregui, S F Ng, K L Gann, D J WaxmanXenobiotic induction of P-450 PB-4 (IIB1) and P-450c (IA1) and associated monooxygenase activities in primary cultures of rat hepatocytes, Xenobiotica 21:1091–1106, 1991). In this method the medium added to the device from Example 1 on the first day post seeding after installation of the cap 110 was supplemented with 70 μM diazepam (Sigma). A 750 μL sample was collected after incubation for 24 hours and frozen until extraction; a sample of the diazepam-supplemented medium prior to addition to the device also was collected and frozen. Solid-phase extraction was performed with Oasis cartridges (Waters Corp., Milford, Mass.) and a Waters extraction manifold. Cartridges were primed sequentially with first methanol and then reverse-osmosis deionized water (RODI). Samples were loaded onto the column and washed with 5% methanol in RODI, eluted off the column with methanol, and evaporated and reconstituted with 250 μL of a mobile phase of 65% methanol/35% 0.01 M ammonium acetate at pH 6.0. Reverse-phase HPLC was conducted at a flow rate of 1.0 mL/min on a Waters Micro-Bondpak C18 column at 24.5° C. Elution was measured by optical absorbance at 254 nm. Diazepam eluted at approximately 11 minutes; the metabolites nordiazepam and temazepam eluted at 10 and 8 minutes, respectively. Data were expressed as percentage of the initial diazepam cleared and as percentages of the initial diazepam converted to nordiazepam or temazepam.

In this assay, high percentages of initial diazepam cleared and converted to nordiazepam and temazepam correspond to high P450 isozyme activity. The higher these percentages, the greater the P450 activity.

Example 5
Hepatocellular Detoxification Activity Based on Metabolism of Lidocaine Metabolism of the drug lidocaine provided another method to evaluate the detoxification activity of hepatocytes supported in device 1 of Example 1. The clearance of lidocaine was evaluated using a method similar to that of Nyberg et al. (S L Nyberg, H J Mann, R Remmel, W-S Hu, F B Cerra, Pharmacokinetic analysis verifies P450 function during in vitro and in vivo application of a bioartificial liver, ASAIO J 39:M252–256, 1993). In this method the medium added to the device from Example 1 on the first day post seeding after capping was supplemented with 740 μM lidocaine (Paddock Laboratories Inc., Minneapolis, Minn.). A 600 μL sample was collected after incubation for 24 hours and frozen until extraction; a sample of the lidocaine-supplemented medium prior to addition to the device also was collected and frozen. Solid-phase extraction was performed with Oasis cartridges (Waters Corp.) and a Waters extraction manifold. Cartridges were primed 99% MeOH 1% HCl and 0.5 M Borax. Samples were loaded onto the column and washed with 0.5 M Borax, eluted with MeOH/HCl and then evaporated and reconstituted with 250 μl of mobile phase of 85% (50 mM $NH_4HPO_4$+10 mM hexane-sulfonic acid, pH 3.0)/15% acetonitrile. Reverse-phase HPLC was conducted at a flow rate of 1 mL/min on a Microsorb C8 column (Rainin Instrument Co., Woburn, Mass.) at room temperature. Elution was measured by optical absorbance at 214 nm. Lidocaine eluted at approximately 37 minutes; MEGX, the major metabolite, eluted at 27 minutes. Data were expressed as percentage of the initial lidocaine cleared.

In this assay, high percentages of initial lidocaine cleared and converted to metabolites correspond to high P450 isozyme activity. The higher these percentages, the greater the P450 activity.

Example 6
Hepatocellular Ureagenesis of Medium Based on Synthesis of Urea

Urea synthesis was determined by either of two methods for device 1 of Examples 1 and 2.

Method 1

The clearance of ammonia, its salts, and aminated components in the medium, through deamination and ureagenesis, is believed to be a critical function of hepatocytes in vivo and a desired function of these cells as part of a LAD. Deamination results in the formation of urea, which in vivo is cleared by the renal system. The synthesis of urea was measured with devices 1 from Examples 1 and 2 using a colorimetric method for the determination of nitrogen, available as Kit #640-B from Sigma Diagnostics (St. Louis, Mo.). Samples were collected periodically after seeding of cells into devices and treated with urease to hydrolyze urea to $NH_3$ and $CO_2$. The resulting $NH_3$ then was reacted with hypochlorite and phenol in the presence of the catalyst, sodium nitroprusside, to form indophenol. The optical absorbance of the resulting solution of indophenol was measured at 570 nm and converted to concentration of urea in the original sample using a standard curve. Data were expressed as amount of urea produced per device per day by multiplying the concentrations by volume of medium 11 in the device and dividing by number of days since sampling.

Method 2

In this assay, hepatocyte cultures were challenged with ammonium chloride and ornithine in order to increase urea production. The synthesis of urea is part of the process of deamination and ureagenesis. Accordingly, increases in the synthesis of urea, particularly in response to challenge with exogenous ammonia, represent increased functional capacity to deaminate media. After challenge, the medium from the cultures was tested to measure the amount of urea produced.

A stock solution of 1 M ammonium chloride ($NH_4Cl$; Sigma #A-0171) was prepared by adding 1.07 g $NH_4Cl$ to 10 mL of RODI. The solution was stored at 4° C. until use. A stock solution of 0.2 M ornithine (Sigma #O-6503) was prepared by adding 0.34 g to 10 mL of RODI. This solution also was stored at 4° C. until use.

Culture plates were then rinsed with 1× phosphate buffered saline (PBS). To each plate was added 10 μL of each ammonium chloride and ornithine for each 1 mL of William's 1% medium (supplemented with the following: 4.5 g/L glucose, 0.5 U/mL bovine insulin, 7 ng/mL glucagon, 7.5 μg/mL hydrocortisone, 10 mM HEPES, 20 ng/mL, EGF, 20 mM glutamine, 10 IU penicillin, and 10 μg streptomycin and 1% new-born calf serum (NBCS)), that is, 40 μL were added as 4 mL of William's medium is used to culture porcine hepatocytes in 60 mm culture plates. Plates with regular culture medium not treated with ammonium chloride and ornithine were included as controls. The plates were returned to the incubator for 24 hours. After incubation, 2 mL of medium was removed from plates and transferred into appropriately labeled test tubes (Falcon #2054) and the tubes stored at −20° C.

The amount of urea present in frozen samples was determined using a Blood Urea Nitrogen (BUN) kit (Sigma, kit #535). Thawed 40 μL samples were added with 3.0 mL of the BUN acid reagent and 2.0 mL of the BUN color reagent to 100 mm disposable borosilicate glass tubes. Tubes were incubated at 100° C. for 10 minutes and then at room temperature for 3–5 minutes. Once cooled tubes were mixed well using the Vortex shaker. Resulting solutions were sampled colorimetrically in 96-well plates in triplicate at 546 nm. Optical absorbances were converted to concentrations of urea using a standard curve and data expressed as amount of urea produced per device per day by multiplying concentrations by volume of medium 11 in the device and dividing by number of days since sampling.

In this assay, high rates of formation of urea correspond to expected high levels of deamination and clearance of ammonia, clinically desired target functions. The higher the rate of urea synthesized, the greater the expected level of deamination.

Example 7

Synthesis and Secretion of Hepatocellular Proteins Based on Secretion of Albumin The synthesis and secretion of serum proteins, including albumin, is believed to be a critical function of hepatocytes in vivo and in a LAD. Albumin is used as a marker of the secretory activity of hepatocytes. The secretion of albumin was measured using a standard competitive ELISA with samples for device 1 of Examples 1 and 2. Samples were collected periodically after seeding cells 40 into devices 1 and frozen until analyzed by ELISA. For ELISAs individual wells in 96-well plates were coated overnight with 200 μg/mL porcine albumin (Accurate Chemical, Westbury, N.Y.). Following a wash step with Tween 20 (Pierce, Rockford, Ill.), 50 μL of a sample or standard (Accurate) in individual wells of a multiwell plate was incubated with a horseradish peroxidase-conjugated goat anti-pig albumin antibody (Bethyl Labs, Montgomery, Tex.) for 90 minutes. Color was produced by addition of O-phenylenediamine dihydrochloride (Pierce) and the reaction stopped by adding $H_2SO_4$. The optical absorbance of individual wells was measured at 490 nm using a Molecular Devices SpectraMax 250 plate reader with SoftMax Pro software and converted to concentration of albumin in the original sample using a standard curve. Data were expressed as amount of albumin produced per device per day by multiplying the concentrations by volume of medium in the device and dividing by number of days since sampling.

In this assay, higher rates of albumin secretion are marks of clinically desired function by differentiated hepatocytes.

Example 8

Determination of Adherent Cell Mass Based on Measurement of Total Hepatocellular Protein Hepatocyte cell mass and attachment was determined for device 1 of Examples 1 and 2 based on amount of associated protein using a BCA Protein Assay Kit (Pierce, catalogue no. 23225). Assay reagents were prepared according to the instructions contained therein. Reagent A was prepared as 1 L of base reagent-with sodium carbonate, sodium bicarbonate, BCA detection reagent, and sodium tartrate in 0.2 N NaOH. Reagent B was prepared as a 25 mL of 4% copper sulfate solution. Bovine Serum Albumin (BSA, Pierce, Cat. No 23209) was used as standards at 2 mg/mL in 0.9% sodium chloride and 0.05% sodium azide.

Devices 1 were removed from the incubator, caps 110 removed, and medium 11 aspirated from cultures. The medium was replaced with phosphate buffered saline (PBS) and cultures frozen at 0° C. for 24 hours. Cultures were then thawed and scraped from gas-permeable, liquid-impermeable membranes 30 into appropriately-labeled test tubes.

A solution of working reagent was prepared by combining 50 parts reagent A with 1 part reagent B. A set of protein standards was prepared by serially diluting 0 to 2 mg/mL of the stock BSA solution in the same diluent. Next, 10 μL of each sample or standard and 200 μL of the working reagent were sequentially was added to individual wells of 96-well plates. Samples were mixed for 30 seconds by gently shaking prior to covering and incubating at 37° C. for 30 minutes. Wells then were assessed colorimetrically at 560 nm. Protein concentrations for unknowns were determined from a standard curve.

Example 9

Comparison of Alternative Gas-Permeable Membranes for Hepatocytes in Cell Culturing Devices The apparatus of Example 1 was used to evaluate the potential of different gas-permeable, liquid-impermeable membranes as supports for hepatocytes in culture. Hepatocytes lose their functionality if not seeded onto a solid support following isolation from a donor. Further, the level of function that they achieve in culture can depend critically on the properties of the culture support, including whether it is coated with a layer or gel of collagen or substances that promote adhesion and function.

Membranes evaluated included Polyflex® (a non-porous 0.002"-thick film of polystyrene manufactured by Plastics Suppliers, Inc., Columbus, Ohio), Breathe-Easy™ (a non-porous film of polyurethane manufactured by Diversified Biotech, Boston, Mass.), a three-layered co-extruded film of styrene-butadiene-styrene/ethyl vinyl acetate/styrene-butadiene-styrene (SBS/EVA/SBS, a non-porous film supplied by BASF, Germany to Baxter Healthcare Corporation, Nivelles, Belgium), a two-layered co-extruded film of styrene-butadiene-styrene/polyethylene (SBS/PE, manufactured by Cypress Cryovac/Sealed Air Corp., Rochester, N.Y.), non-porous polyester sheet (manufactured by Perfecseal Inc., Philadelphia, Pa.), HDPE in the form of TYVEK® 1073 (a microporous non-woven membrane composed of USP Class VI polyolefin and manufactured by E. I. du Pont de Nemours and Co, Inc., Wilmington, Del.), microporous polyethylene (PE) sheet (obtained from 3M, Inc. (Minneapolis, Minn.) with a mean pore size of 1.7 $\mu$m as determined by a bubblepoint test), PolySep® (microporous polypropylene sheet manufactured by Micron Separations, Westborough, Mass.), microporous poly (tetrafluoroethylene) (PTFE) and Hydrulon® (microporous hydrophobized nylon 6,6) (both manufactured by Pall Corporation, Port Washington, N.Y.), and track-etched polycarbonate (manufactured by Micron Separations). Membranes with two different pore sizes were examined for the microporous PTFE, Hydrulon, and track-etched polycarbonate.

Each of the membranes tested would be expected to have sufficient permeability to oxygen and carbon dioxide to support direct transmembrane oxygenation of adherent hepatocytes. Further, each of these membranes would be expected to be water-impermeable for the pressure differences across the membrane expected for oxygenation and perfusion in a cell culture device or organ assist system.

Each of these membranes was evaluated without coating with collagen type I prior to seeding of cells at a density of 2×10$^6$ hepatocytes per device. An oxygenated fluid supply with 19% $O_2$, 10% $CO_2$, and balance $N_2$ was used. Data for detoxification activity by methods of conversion of alkoxyresorufin to resorufin (Example 3) for cells from donor 54 (polyurethane, PTFE, and hydrophobized nylon), donor 61 (HDPE), donor 76 (track-etched polycarbonate), donor 80 (SBS/EVA/SBS, PS/PE, and PE), donor 84 (polyester), and donor 89 (polystyrene) on day 1 post seeding are presented in Table 1.

TABLE 1

Detoxification Activity for Hepatocytes in Static Cultures in Cell Culturing Devices for Different Gas-Permeable, Liquid-Impermeable Membranes

| Gas-Permeable Membrane | | Detoxification Activity | |
|---|---|---|---|
| Material (Source) | Pore Size | BROD | EROD |
| Polystyrene (Polyflex ®, Plastics Suppliers) | Nonporous | 1.44 | 1.11 |
| Polyurethane (Breathe-Easy ™, Diversified Biotech) | Nonporous | 0.33 | 0.84 |
| SBS/EVA/SBS (BASF) | Nonporous | — | 0.65 |
| Co-extruded poly-ethylene/polystyrene (Cryovac) | Nonporous | — | 0.72 |
| Polyester (Perfecseal) | Nonporous | 1.10 | 1.68 |
| HDPE (TYVEK ® 1073, Dupont) | 4.2 $\mu$m | 0.22 | 0.81 |
| Polyethylene (3M) | <10 $\mu$m | 0.77 | 0.95 |
| Polypropylene (Pylysep ®, Micron Separations) | 0.45 $\mu$m | 0.48 | 0.74 |
| PTFE (Pall) | 0.1 $\mu$m | 0.38 | 0.87 |
| PTFE (Pall) | 1 $\mu$m | 0.47 | 0.93 |
| Hydrophobized nylon 6,6 (Hydrulon ®, Pall) | 0.2 $\mu$m | 0.35 | 1.38 |
| Hydrophobized nylon 6,6 (Hydrulon ®, Pall) | 1.2 $\mu$m | 0.31 | 1.29 |
| Track-etched polycarbonate (Micron Separations) | 0.1 $\mu$m | 0.45 | 0.91 |
| Track-etched polycarbonate (Micron Separations) | 1 $\mu$m | 0.24 | 0.48 |

Highest levels of detoxification activity for the biotransformation of BROD to resorufin were observed for cells cultured in devices comprising Polyflex® or the polyester membrane. The microporous polyethylene membrane supported intermediate levels of detoxification activity for conversion of BROD in the cell-seeded device 1. Highest levels of detoxification activity for the biotransformation of EROD to resorufin were observed for cells cultured in devices comprising Polyflex®, the polyester membrane, or Hydrulon®. Increasing pore size decreased detoxification activity for both alkoxyresorufins on track-etched polycarbonate but had relatively minor effects for microporous PTFE and hydrophobized nylon 6,6. In general, detoxification activity was more dependent on membrane type for BROD than for EROD. Further, the highest overall detoxification activities were observed for cell-seeded devices comprising non-porous polystyrene or polyester.

These results demonstrate how changing the chemical composition and physical structure of a gas-permeable, liquid-impermeable membrane 30 can affect the ability of hepatocytes 40 cultured in a device 1 to perform detoxification.

The apparatus of Example 1 also was used to compare the ureagenesis potential of hepatocytes cultured in a device 1 comprising Polyflex® with hepatocytes 40 cultured in equivalently sized 60 mm-diameter tissue-culture dishes. Tissue-culture dishes present to cells a surface effectively impermeable to gas, including oxygen, relative to Polyflex®: Polyflex® has a permeability to oxygen on the order of 2.0×10$^4$ mL/m$^2$-day-atm, whereas the permeability to oxygen of tissue-culture dishes is below the ability of state-of-the-art techniques to measure.

Figure 11:
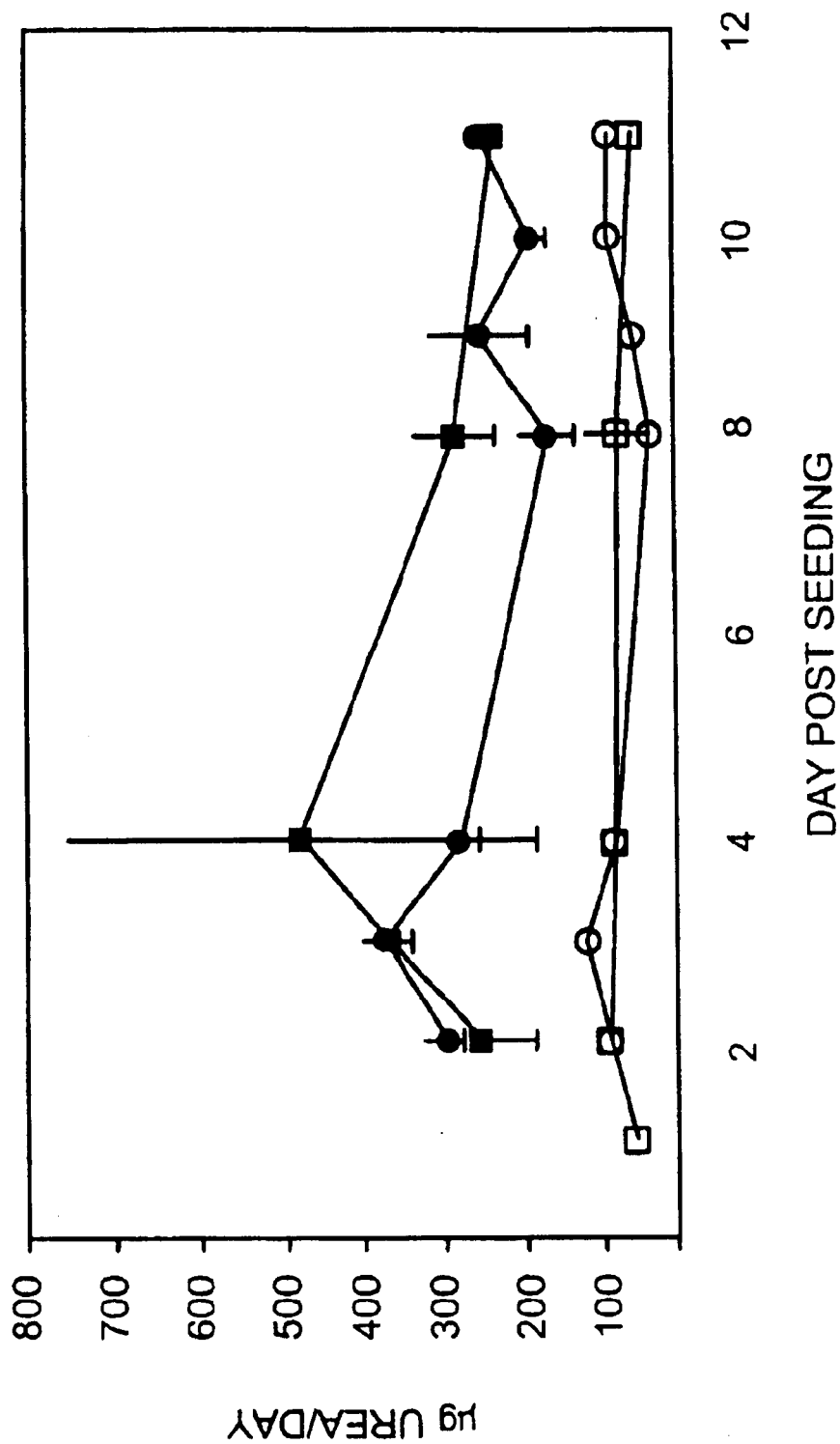
FIG. 11 is a graph comparing the synthesis of urea by hepatocytes cultured statically in devices comprising collagen-coated, corona treated 0.002"-thick gas-permeable polystyrene and in tissue-culture dishes.

For this study 2×10$^6$ hepatocytes from donor 93 were seeded into either a device 1 with Polyflex® or into a tissue-culture dish. The device was supplied with a gas feed of 19% $O_2$, 10% $CO_2$, and balance $N_2$. Data for the synthesis of urea, in terms of both the basal level (open symbols based on Example 6, Method 2 without addition of exogeneous ammonia and ornithine) and in response to challenge with 20 mM exogeneous ammonia (closed symbols based on Example 6, Method 2 with addition of exogeneous ammonia and ornithine), is presented in FIG. 11 for devices (squares) and tissue-culture dishes (circles). The basal level of synthesis of urea for devices over the course of 11 days of culture is indistinguishable from the basal level for hepatocytes maintained in tissue-culture dishes over this period of time. Further, the synthesis of urea in response to challenge with ammonia is the same as or greater in the devices than in the tissue-culture dishes. These results demonstrate that not only can higher levels of detoxification be achieved upon culturing hepatocytes on a gas-permeable membrane such as Polyflex® but also ureagenesis, particularly in response to exogenous ammonia, can be enhanced by culturing hepatocytes adherent on a gas-permeable membrane in a device.

Example 10
Effect of Surface Treatment of Gas-Permeable Membranes on Hepatocytes in Cell Culturing Devices The effect of modification of the surface of gas-permeable, liquid-impermeable membranes 30 also was evaluated using the apparatus of Example 1. Specific modification (e.g., by coating or covalent attachment of specific molecules) and non-specific modification (e.g., by treating the surface with an oxidizing chemical or physical process) alters the cell-adhesive properties of surfaces and the ability of these surfaces to promote cell function. These treatments modify only the surface of the cell-supporting membrane and not the membrane's bulk properties.

We evaluated the effects of two independent treatments 41, applied prior to seeding cells 40, to control the function of hepatocytes cultured on gas-permeable, liquid-impermeable membranes 30 in a device 1. One treatment comprised coating the surface of the membrane with a sterile solution of 1.1 mg/mL collagen type I for 45 minutes, followed by rinsing with sterile phosphate-buffered saline. The resulting coating was on the order of one to a few molecules of collagen thick. This type of treatment enhances the adhesion of many types of cells to many otherwise less-adhesive surfaces. The second treatment comprised exposure of the cell-supporting side of membranes to a corona discharge to oxidize this surface. Treatment of polystyrene dishes with a corona discharge oxidizes the cell-supporting surface, such that the dyne level (critical surface tension) is 40–50 dynes/cm, and promotes cell attachment for many types of cells. This treatment modifies only a thin surface-most layer of the surface, of thickness less than approximately 1 micron, without increasing the thickness of the membrane or depositing macroscopic amounts of material onto the membrane. This treatment was applied to both the non-porous Polyflex® (polystyrene) and porous TYVEK® 1073 (non-woven HDPE) membranes such that their dyne levels (critical surface tensions) became approximately 45 dyne/cm.

Table 2 presents data for detoxification activity by methods of conversion of alkoxyresorufin to resorufin (Example 3) for cells, seeded at $2 \times 10^6$ hepatocytes per device 1, from donor 61 (HDPE), donor 76 (track-etched polycarbonate), donor 80 (SBS/EVA/SBS, PS/PE, and PE), and donor 89 (polystyrene) on day 1 post seeding for devices supplied with 19% $O_2$, 10% $CO_2$, and balance $N_2$. Changes in detoxification in response to surface treatment 41 depended on the specificity of detoxification (BROD or EROD) as well as membrane type. For some membranes (e.g., HDPE and track-etched polycarbonate with 1 micron-diameter pores), coating with collagen improved both specificities of detoxification. For other membranes (e.g., polystyrene, co-extruded polyethylene/polystyrene, track-etched polycarbonate with 0.1 micron-diameter pores) coating with collagen improved only one specificity of detoxification with minor changes in the alternative specificity. The remaining membranes experienced minor reductions in detoxification upon treatment with collagen.

TABLE 2

Effect of Surface Treatment of Gas-Permeable Membranes on Detoxification Activity for Hepatocytes in Static Cultures in Cell Culturing Devices

| | Gas-Permeable Membrane | | | |
|---|---|---|---|---|
| | Surface Treatment | | Resorufin Activity | |
| Material | Collagen coated | Corona treated | BROD | EROD |
| Polystyrene | No | No | 1.44 | 1.11 |
| | Yes | No | 2.04 | 0.94 |
| | No | Yes | 1.64 | 1.08 |
| | Yes | Yes | 1.51 | 1.60 |
| SBS/EVA/SBS | No | No | — | 0.65 |
| | Yes | No | — | 0.45 |
| Co-extruded polyethylene/polystyrene | No | No | — | 0.72 |
| | Yes | No | — | 0.79 |
| HDPE | No | No | 0.22 | 0.81 |
| | Yes | No | 0.32 | 0.99 |
| | No | Yes | 0.60 | 1.00 |
| Polyethylene | No | No | 0.77 | 0.95 |
| | Yes | No | 0.54 | 0.86 |
| Polycarbonate (0.1 µm pores) | No | No | 0.45 | 0.91 |
| | Yes | No | 0.31 | 1.23 |
| Polycarbonate (1 µm pores) | No | No | 0.24 | 0.48 |
| | Yes | No | 0.59 | 0.91 |

Surface treatment with corona discharge in the absence of coating with collagen significantly improved the detoxification activity of both polystyrene and HDPE. Sequential treatment by corona discharge followed by coating with collagen further improved the overall detoxification activity of polystyrene. This combination, when applied to Polyflex®, produced the system with the greater detoxification activity.

Culturing hepatocytes in a device 1 comprising corona discharge-treated, collagen-coated Polyflex® also supported sustained detoxification activity over the evolution of a culture. For these evaluations detoxification activity based on the biotransformation of BROD and EROD (Example 3) was measured on days one, three, and seven post seeding. The values for BROD decreased slightly (from 1.51 on day one to 1.47 on day three to 1.20 on day seven), whereas the values for EROD increased from day one to day three (1.60 to 4.25) before decreasing on day seven (0.87). All of these values for detoxification activity were higher than for other membranes.

These results demonstrate the utility of modifying gas-permeable, liquid-impermeable membranes 30 with one or more surface treatments 41, in which only the surface of the membrane exposed to cells 40 (and not the membrane's gas permeability) is modified, in order to achieve desired increases in hepatocyte function in a cell culturing device 1.

Example 11
Effect of Oxygenation on Hepatocytes in Unperfused Cell Culturing Devices The apparatus of Example 1 was used to compare the effect of various gas compositions on the functions of static hepatocyte cultures. The partial pressure of oxygen to which cells, and in particular hepatocytes, are exposed can significantly influence their function. Direct transmembrane oxygenation of adherent cells can be achieved in device 1 by feeding a gas with desired concentration of oxygen to one side of a gas-permeable membrane and culturing cells on the opposing side. This mode of oxygenation offers reduced resistance to the transport of oxygen to cells compared to oxygenation through saturation of medium with oxygen. Further, direct transmembrane oxygenation effectively decouples oxygenation and perfusion of cells.

For this Example oxygenation of adherent hepatocytes in static cultures was controlled by setting the concentration of oxygen in the gas fed to the device 1 and contacted with the gas-permeable, liquid-impermeable cell-supporting membrane 30. Two different membranes were examined: corona discharge-treated, collagen-coated polystyrene (Polyflex®) and uncoated, non-woven HDPE (TYVEK® 1073). Gas compositions tested comprised 10% $CO_2$ with 0%, 19%, 40%, 60%, 65%, or 90% $O_2$, and balance $N_2$. Carbon dioxide was included to maintain a physiological pH based on the used of a standard bicarbonate-based buffer.

FIGS. 12a–d show data for the attachment of cells one day post seeding (Example 6), for ureagenesis (Example 5), for detoxification activity based on biotransformation of alkoxyresorufins (Example 3), and detoxification activity based on the metabolism of lidocaine (Example 5) for hepatocytes 40 cultured statically in devices 1 containing 0.002"-thick corona-treated, collagen-coated polystyrene. Data were obtained for $2\times10^6$ hepatocytes seeded from donor 100 and 101 and were expressed relative to devices fed 19% $O_2$. Attachment one day post seeding (FIG. 12a), measured as the amount of total protein associated with adherent cells, doubled with an increase in concentration of $O_2$ in the feed gas to 60%.

Figure 12:
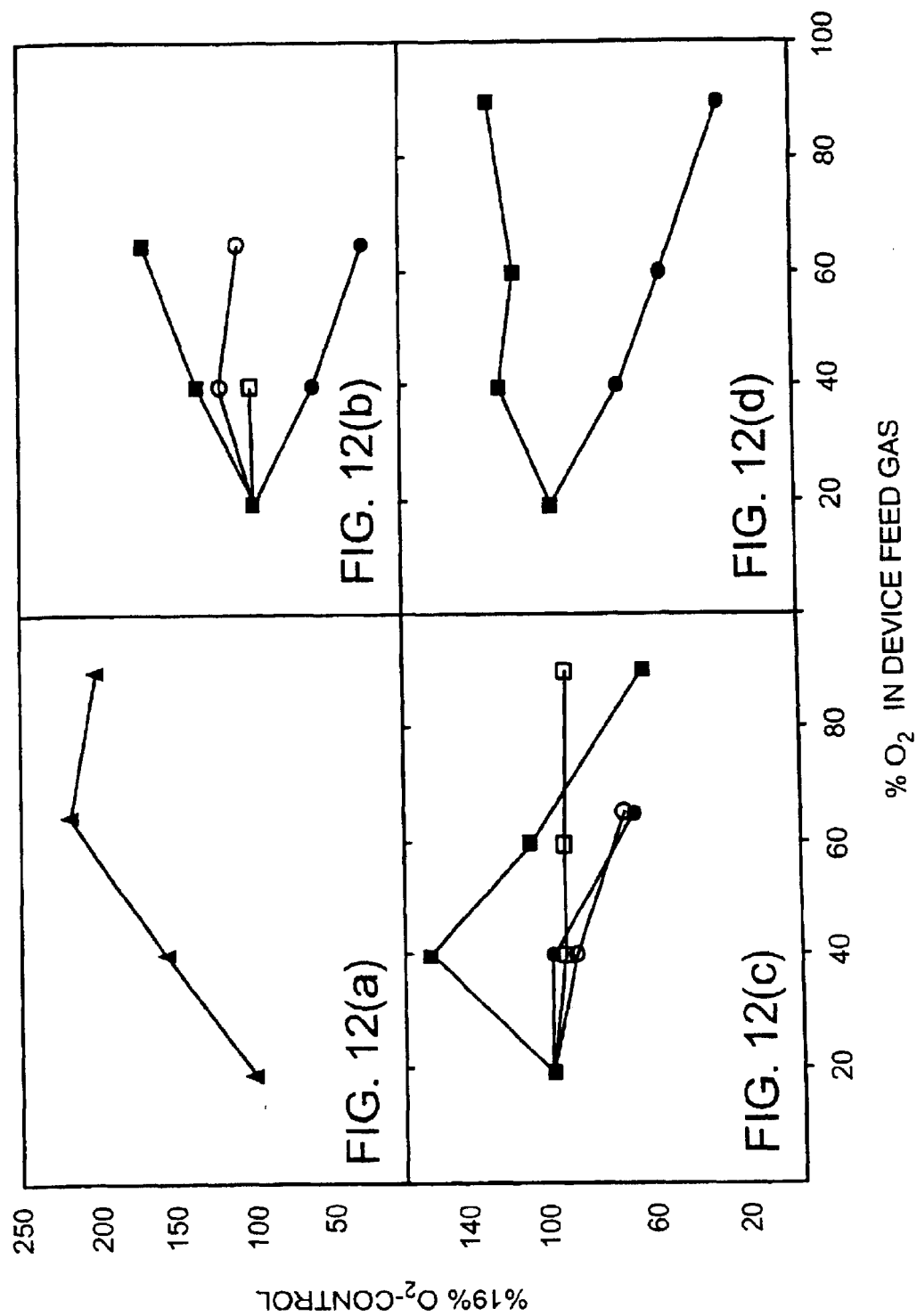
FIGS. 12a, 12b, 12c, and 12d are graphs showing the effects of oxygenation on (12a) attachment of cells one day post seeding, (12b) basal and challenged synthesis of urea, (12c) detoxification activity for alkoxyresorufins, and (12d) metabolism of lidocaine by hepatocytes cultured statically in devices comprising a 0.002"-thick corona-treated, collagen-coated polystyrene gas-permeable membrane.

Data for the synthesis of urea, in terms of both the basal level (open symbols) and in response to challenge with 20 mM exogenous ammonia (closed symbols), are presented in FIG. 12b for devices 1 on days two (squares) and five (circles) post seeding. Basal levels are relatively independent of the concentration of $O_2$ in the feed gas. Conversely, challenged rates of urea synthesis increased with concentration of $O_2$ on day two post seeding but decreased with concentration of $O_2$ on day five post seeding.

Data for detoxification activity based on the conversion of BROD (squares) and EROD (circles) to resorufin is presented in FIG. 12c for days one (closed symbols) and four (open symbols) post seeding. On day one post seeding greatest detoxification activities were observed for an intermediate concentration of $O_2$ of 40%. On day four post seeding detoxification activity for BROD was independent of concentration of $O_2$, but detoxification activity for EROD decreased monotonically with concentration of $O_2$ on this day in culture.

Complementary trends were observed for the amounts of metabolites of lidocaine (FIG. 12d). On day two post seeding (closed squares) the amount of metabolites increased slightly with increasing concentration of $O_2$, but on day five post seeding (closed circles) the amount of metabolites for lidocaine decreased sharply with increasing concentration of $O_2$.

These results demonstrate that controlling the concentration of oxygen fed into a device 1 comprising corona discharge-treated, collagen-coated Polyflex®, thereby controlling the extent of oxygenation of static cultures of hepatocytes 40, can be used to control a wide range of functions of hepatocytes. Further, by selecting the concentration of oxygen and varying it over different days in culture, different functions can either be promoted or down-regulated.

Similar types of data were obtained for hepatocytes 40 cultured statically in devices 1 comprising TYVEK® 1073 as the gas-permeable, liquid-impermeable membrane/cell support 30. Hepatocytes in this system were seeded at a density of $2\times10^6$ cells per device and evaluated for the effect of oxygenation on their detoxification activity by methods of conversion of alkoxyresorufin to resorufin (Example 3) on day 1 post seeding for cells from donor 73 and clearance of diazepam (Example 4) on days 2 and 4 post seeding for cells from donor 78, ureagenesis based on basal levels of synthesis of urea (Example 5) for day 3 post seeding for cells from donor 76, and synthesis and secretion of albumin (Example 6) for cells from donor 74. Data were collected for these assays from different porcine donor and are summarized in FIG. 13 and Tables 3 and 4.

Figure 13:
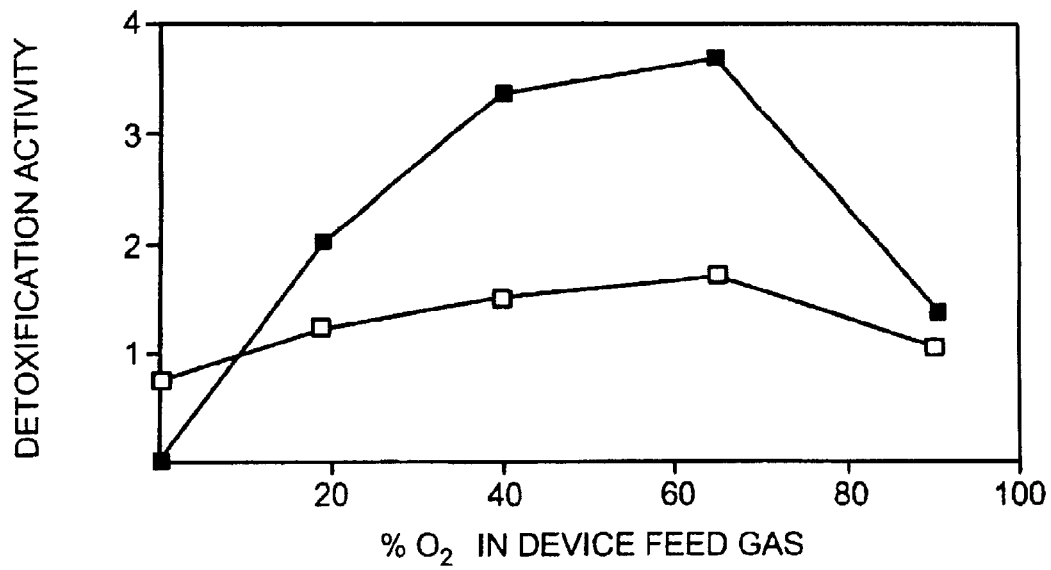
FIG. 13 is a graph showing the effect of transmembrane oxygenation on detoxification activities for alkoxyresorufin by hepatocytes cultured statically in devices comprising TYVEK® 1073.

FIG. 13 shows that greatest detoxification activities for BROD (closed squares) and EROD (open squares) were observed for transmembrane oxygenation with 65% $O_2$. Exposure to higher or lower concentrations of $O_2$ resulted in lower detoxification activity: exposure to 0% $O_2$ asphyxiated cells, exposure to 19% and 40% $O_2$ was limiting for detoxification activity, and exposure to 90% $O_2$ was hyperoxic and deleterious for cells. Similarly, Table 3 shows that higher percentages of diazepam were cleared and metabolized to nordiazepam and temazepam for an increase in oxygenation to 40% from 19%.

TABLE 3

Metabolism of Diazepam for Hepatocytes in Static Cultures in Cell Culturing Devices as Function of Oxygenation

|  | %-Diazepam Cleared | %-Diazepam Converted to Nordiazepam | %-Diazepam Converted to Temazepam |
|---|---|---|---|
| Day 2 |  |  |  |
| 19% $O_2$ | 47.8% | 3.0% | 2.9% |
| 40% $O_2$ | 51.6% | 3.3% | 3.2% |
| Day 4 |  |  |  |
| 19% $O_2$ | 39.7% | 0.8% | 1.5% |
| 40% $O_2$ | 52.3% | 1.8% | 3.7% |

Further, devices 1 comprising TYVEK® 1073 and connected to 19% and 65% $O_2$ produced 20.5 and 42.5 μg/day of urea, respectively, demonstrating that the exposure to a more oxygen-rich gas increased the level of ureagenesis on this membrane material.

As shown in Table 4, a different trend with respect to level of oxygenation was observed for albumin secretion on TYVEK® 1073 in devices 1: the maximum rate of secretion of albumin was detected for exposure to 19% $O_2$, with lower rates for exposure to higher concentrations of $O_2$. Together these results show the potential benefits of direct transmembrane oxygenation, controlled by manipulating the concentration of $O_2$ in the gas, on control of hepatocyte function, and how change of gas composition can be used to manipulate hepatocyte function.

TABLE 4

Secretion of Albumin for Hepatocytes in Static Cultures in Cell Culturing Devices as Function of Oxygenation

| | Rate of Albumin Secretion (μg/day) | | | |
|---|---|---|---|---|
| % $O_2$ in Device Feed Gas | Day 3 Post Seeding | Day 6 Post Seeding | Day 8 Post Seeding | Day 10 Post Seeding |
| 19 | 0.186 | 0.342 | 2.699 | 3.443 |
| 40 | 0.076 | 0.075 | 0.227 | 0.254 |
| 65 | 0.063 | 0.052 | 0.082 | 0.082 |
| 90 | 0.055 | 0.023 | 2.98 | 0.567 |

Example 12
Effect of Perfusion on Hepatocytes in Cell Culturing Devices

Figure 14:
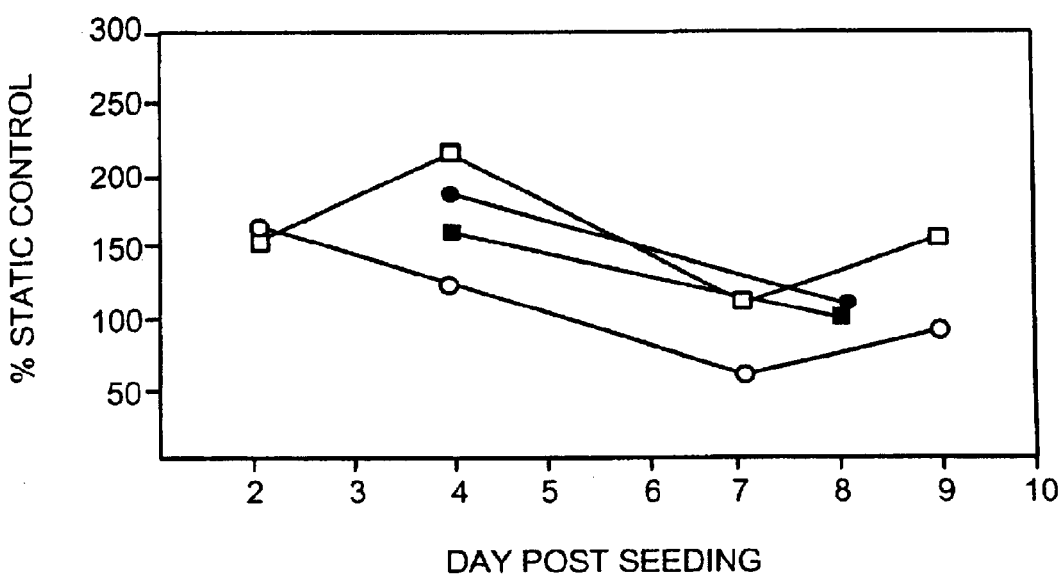
FIG. 14 is a graph showing the effect of changes in the volumetric flow rate of medium on synthesis of urea by hepatocytes cultured in perfused devices comprising 0.002"-thick corona-treated, collagen-coated polystyrene.

The apparatus of Example 2 was used to compare the effect of perfusing hepatocyte cultures at different volumetric flow rates in laboratory-scale devices comprising corona discharge-treated, collagen-coated Polyflex®. Devices 1 were seeded with $2\times10^6$ hepatocytes from donor 96, loaded with 10 mL of complete medium as perfusate, and fed gas containing 19% $O_2$, 10% $CO_2$, and balance $N_2$. FIG. 14 presents data for both basal levels of synthesis of urea (open symbols) and rates of synthesis of urea in response to challenge with 20 mM exogenous ammonia (closed symbols) for devices perfused at 1.5 mL/min (squares) and at 0.1 mL/min (circles). Data are expressed as percentages of static controls. Relative increases in the synthesis of urea, expected to be reflective of greater deamination, were observed for nearly every day in culture examined for both volumetric flow rates and for both basal and ammonia-challenged levels of urea. Neither volumetric flow rate was preferred for both greater basal and challenged ureagenesis. Data for devices seeded with $4\times10^6$ hepatocytes from donor 108 and 109, operated under similar conditions but with higher volumetric flow rates up to 12 mL/min, similarly showed no effect of flow rate on ureagenesis. These results demonstrate that devices 1 can be operated successfully with a range of volumetric flow rates without deleterious effects of hepatocyte function.

The apparatus of Example 2 also was used to compare the effect of perfusing hepatocyte cultures at a constant volumetric flow rate—but with different volumes of perfusate on cell growth and ureagenesis in devices comprising corona discharge-treated, collagen-coated Polyflex®.

For studies of cell growth and ureagenesis devices 1 were seeded with $2\times10^6$ hepatocytes from donor 96, loaded into perfusion circuits with 10 mL of complete medium as perfusate, and fed gas containing 19% $O_2$, 10% $CO_2$, and balance $N_2$. Table 5 presents data for the growth of cells, measured as cell mass by determination of total protein associated with adherent hepatocytes, for covered and capped devices. Data for cell density is expressed as percentage of cell mass observed for cultures in tissue-culture dishes. The static covered device and capped device perfused at 0.1 mL/min show increases in cell mass relative to tissue-culture dishes on day three post seeding. All configurations show extensive increases in cell mass by day nine post seeding. These results demonstrate that perfusion is not deleterious to growth of cultures.

TABLE 5

Effect of Device Configuration and Perfusion on Growth of Hepatocytes in Cell Culturing Devices

| Configuration | System Volume (mL) | Perfusion Rate (mL/min) | Cell Density (%-TC Control) Day 3 | Day 9 |
|---|---|---|---|---|
| Device 1 with Cover 100 | 4 | Static | 189 | 706 |
| Device 1 with Cap 110 | 3 | Static | 79 | 774 |
| Device 1 with Cap 110 | 10 | 0.1 | 127 | 933 |
| Device 1 with Cap 110 | 10 | 1.5 | 91 | 706 |

Figure 15:
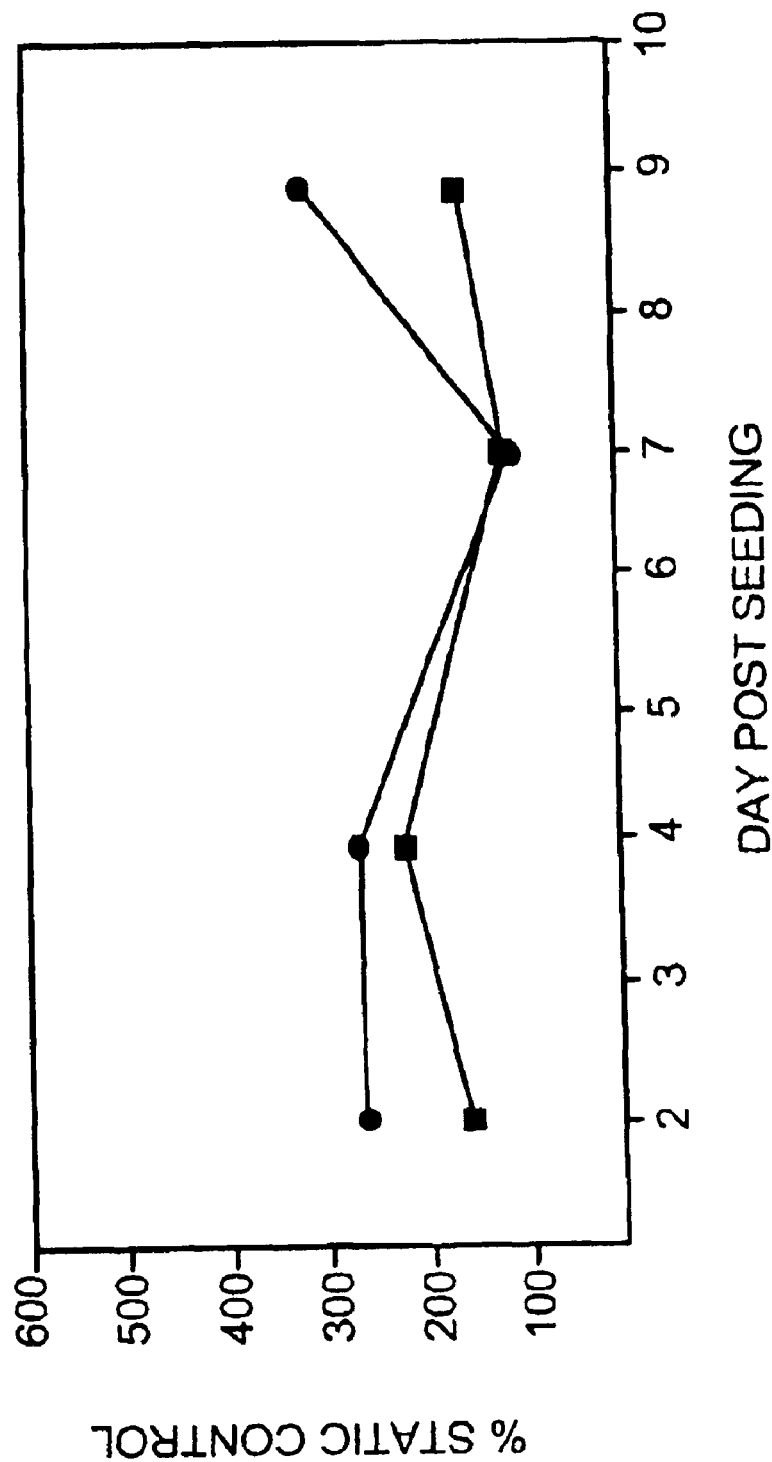
FIG. 15 is a graph showing the effect of changes in the volume of medium on synthesis of urea by hepatocytes cultured in perfused devices comprising 0.002"-thick corona-treated, collagen-coated polystyrene.

FIG. 15 presents data for basal levels of synthesis of urea for single devices perfused at 1.5 mL/min with 10 mL (squares) or 20 mL (circles) of perfusate. Data again are expressed as percentages of static controls. Relative increases in the basal synthesis of urea, expected to be reflective of greater deamination, were observed for every day in culture examined for all three systems. Larger relative increases were observed for devices perfused with 20 mL than with 10 mL. These results demonstrate that controlling the volume of perfusate can be an effective means to control hepatocyte function, and in particular ureagenesis.

Figure 16:
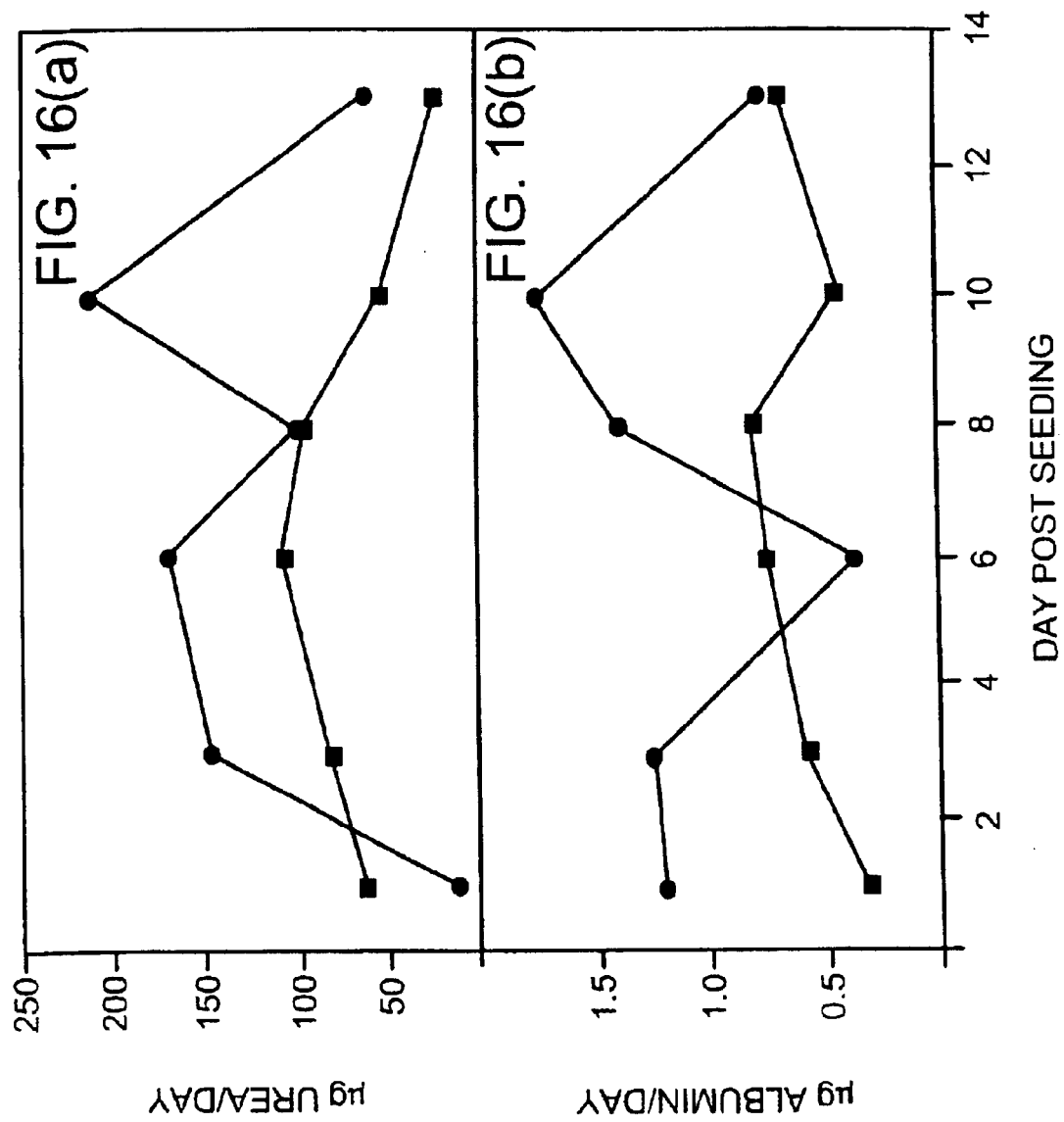
FIGS. 16a and 16b are graphs showing the effect of changes in the volume of medium on (a) synthesis of urea, and (b) on the secretion of albumin for hepatocytes cultured in perfused devices comprising TYVEK® 1073.

The apparatus of Example 2 further was used to compare the effect of perfusing hepatocytes cultures at 1.5 mL/min with different volumes of perfusate in devices 1 comprising TYVEK® 1073 as the gas-permeable, liquid-impermeable membrane/cell culture support 30. In these studies devices were seeded with $2\times10^6$ hepatocytes, loaded with either 10 or 20 mL of complete medium as perfusate, and fed gas containing 40% $O_2$, 10% $CO_2$, and balance $N_2$. Hepatocytes were evaluated for the synthesis of urea (Example 6, Method 1) and synthesis and secretion of albumin (Example 7) for cells from donor 75 for days 1–13 post seeding. Data are presented in FIGS. 16a and 16b.

For almost all time points examined, the synthesis of urea and secretion of albumin was greater with 20 mL of perfusate than with 10 mL of perfusate. These results demonstrate that greater levels of ureagenesis and secretion of albumin can be obtained using perfusion and by increasing the volume of perfusate. This example shows the utility of perfusion with direct transmembrane oxygenation for improved function.

Example 13

Effect of Cell Seeding Density on Hepatocytes in Perfused Cell Culturing Devices The economic efficiency, practicality, and utility of a cell culturing device can be influenced by the density of cells that can be supported in the device: support of greater densities of cells frequently is associated with lower costs and the potential to build smaller devices and units. It further is typically desired that increases in cell density do not result in a significant loss of function on a per cell basis.

To address these issues the apparatus of Example 2 also was used to compare the effect of perfusing hepatocyte cultures seeded at different initial densities of cells on ureagenesis in devices comprising corona discharge-treated, collagen-coated Polyflex®. Devices 1 were seeded with either $4\times10^6$, $8\times10^6$, or $12\times10^6$ hepatocytes 40 from donor 109, loaded into perfusion circuits with 10 µL of complete medium as perfusate 11, fed gas 4 containing 19% $O_2$, 10% $CO_2$, and balance $N_2$, and perfused from Day 1 to Day 2 of culture at 1.5 mL/min. Ureagenesis was determined based on Method 2 of Example 6. Table 6 shows that the rate of synthesis of urea increased approximately linearly with initial seeding density: the rate of ureagenesis per cell seeded varied from 98 to 106 to 85 upon increasing the number of cells seeded per device from $4\times10^6$ to $8\times10^6$ to $12\times10^6$. These results demonstrate that the invention allows linear scaling of hepatocellular function with cell number.

TABLE 6

Ureagenesis for Hepatocytes in Perfused Cell Culturing
Devices as Function of Cell Seeding Density

| Cells Seeded Per Device | Ureagenesis | |
|---|---|---|
| | Total (µg/dev/day) | Per Cell Seeded (pg/cell seeded/day) |
| $4 \times 10^6$ | 390 | 98 |
| $8 \times 10^6$ | 845 | 106 |
| $12 \times 10^6$ | 1019 | 85 |

Figure 17:
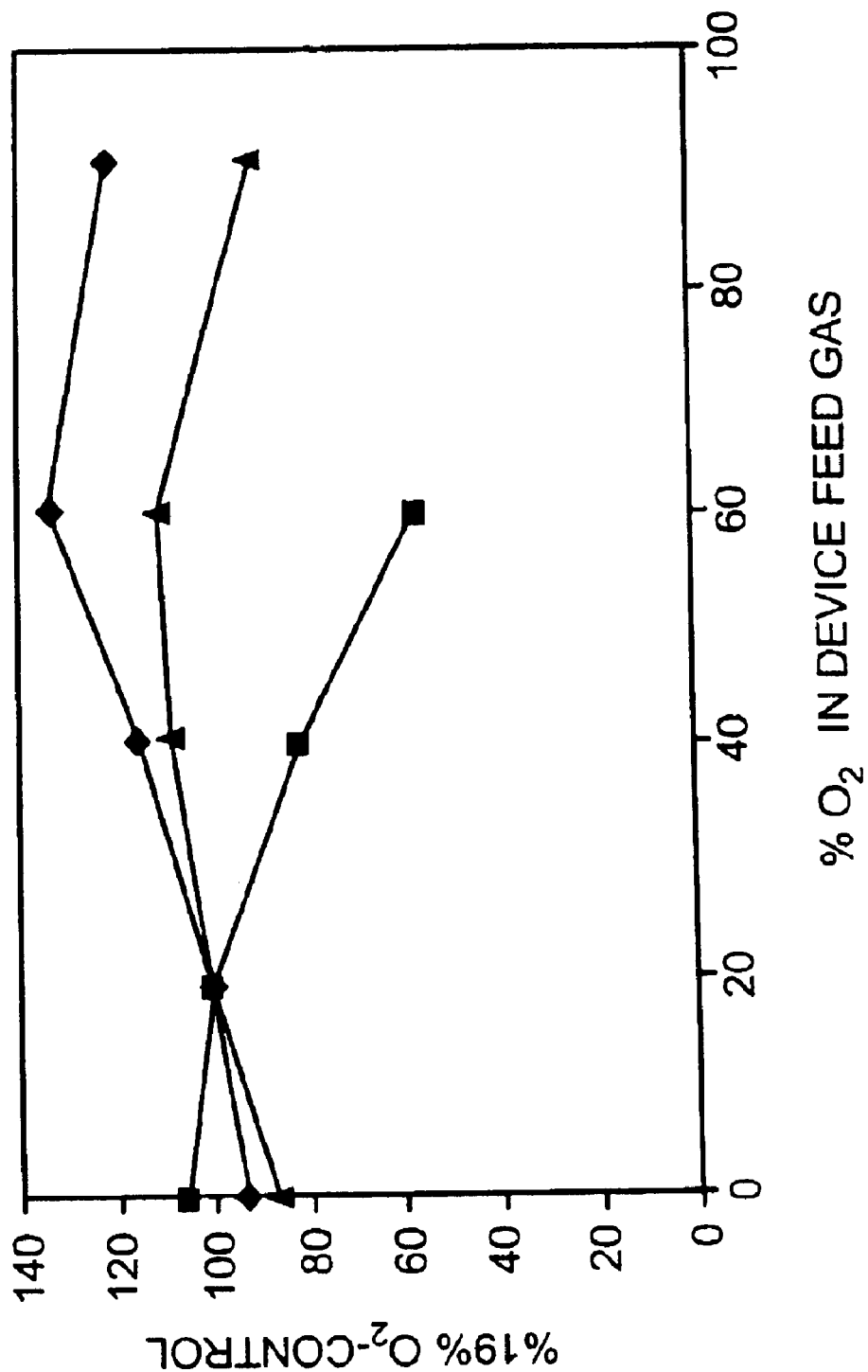
FIG. 17 is a graph showing the effects of transmembrane oxygenation and cell seeding density on ureagenesis for hepatocytes cultured in perfused devices comprising 0.002"-thick corona-treated, collagen-coated polystyrene.

The possible utility of manipulating oxygenation on the function of higher density, perfused cultures also was examined using the apparatus of Example 2. Devices 1 comprising corona discharge-treated, collagen-coated Polyflex® were seeded with either $4 \times 10^6$, $8 \times 10^6$, or $12 \times 10^6$ hepatocytes 40 from donor 105, 109, and 110, loaded into perfusion circuits with 10 mL of complete medium as perfusate 11, fed gas 4 containing 10% $CO_2$ with between 0 and 90% $O_2$ (and balance $N_2$), and perfused from Day 1 to Day 2 of culture at 1.5 mL/min. Ureagenesis again was determined based on Method 2 of Example 6. FIG. 17 depicts data for these studies plotted as percentage of 19% $O_2$ controls. For lower density cultures (e.g., closed squares for $4 \times 10^6$ cells seeded initially), the synthesis of urea in response to challenge with 20 mM exogenous ammonia was greatest under conditions of reduction of oxygenation compared to 19% $O_2$. Further, for this lower density increasing oxygenation decreased ureagenesis. In contrast, for higher density cultures (e.g., closed diamonds for $8 \times 10^6$ cells and closed triangles for $12 \times 10^6$ cells) the rate of ureagenesis was greatest for an intermediate extent of oxygenation with 60% $O_2$.

These results demonstrate that manipulation of oxygenation can be used as a further means of controlling the performance and function of hepatocytes supported in the new cell culturing devices and that the optimal level of oxygenation can depend on the density of cells supported.

Example 14
Scaling of Performance with Size of Cell Culturing Device

The economic efficiency, practicality, and utility of a cell culturing device further can be influenced by the ability to increase the overall size of the device without loss of per-unit-area function. For example, it typically is desired to have 10 times the total function in a device 1 seeded with 10 times as many cells but also 10 times the projected area of the gas-permeable, liquid-impermeable membrane 30, such that the seeding density of cells does not change. This need is dictated by the inability to increase the density of cells seeded without bound without loss of function on a per cell basis.

The present invention allows at least two methods for increasing device size without losing function on a per-area basis: increasing the size of a single unit or coupling multiple units together in parallel, series, or both. The first method involves using devices with units that are larger in absolute size; the second method involves using modular units.

Figure 18:
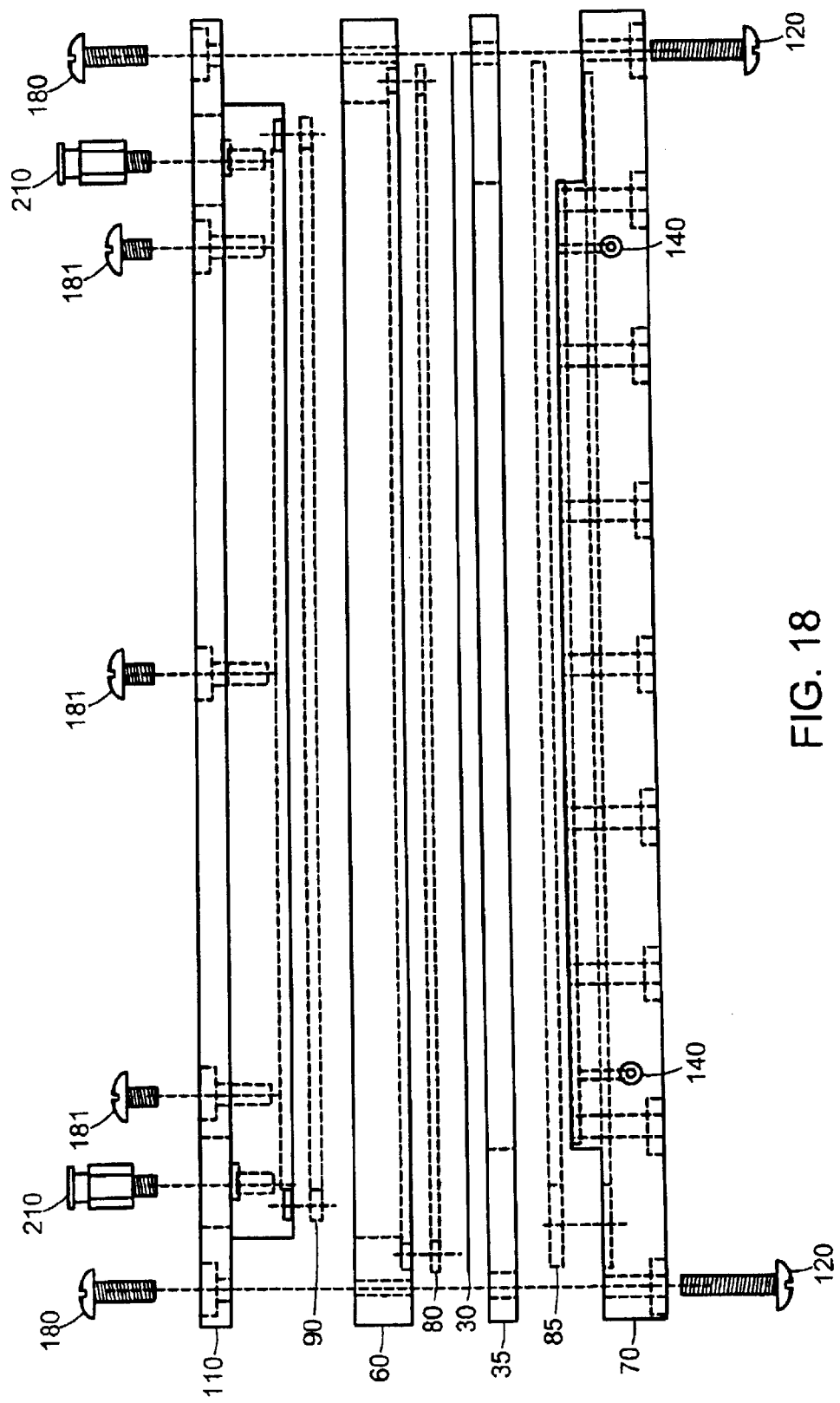
FIG. 18 is a schematic diagram of a side view of cell culture device sized to treat a rat.

The feasibility of scaling absolute device size with single units was examined by comparing the performance of the apparatus of Example 2 with a larger version of the device 1 using the perfusion circuit of Example 2. This larger device is depicted schematically in FIG. 18 and was sized with five times the projected area of gas-permeable, liquid-impermeable membrane 30 as the device of Example 1. This sizing allowed this device to be applied to treat rats with liver failure; hence it was denoted the "rat-scale" device to distinguish it from the "laboratory-scale" or "lab-scale" device depicted in FIG. 4.

The rat-scale device comprised a set of aluminum parts, including upper 60 and lower 70 housings, a frame 35, and cap 110, in addition to gas-permeable, liquid-impermeable membrane 30, three silicone gaskets (Specialty Silicone Products, Inc., Balston Spa, N.Y.) 85, 80, and 90, and ancillary screws and fittings 120, 180, 181, and 210. A membrane/frame assembly 400 was constructed and sterilized by gamma irradiation as described in detail in Example 1. The rat-scale device 1 was also assembled and handled (including seeding of cells 40) as described in detail in Example 1 for the lab-scale device with the following exception: the rat-scale device was seeded with cells suspended in 33 mL of medium rather than 4 mL of medium. The numbers of cells in the suspension was adjusted so that the seeding densities (per unit area) were similar for the two scales.

For this study ureagenesis in the lab- and rat-scale devices were compared for hepatocyte cultures obtained from donor 101 perfused with 20 mL of complete medium 11 at similar hydrodynamic shear stresses for Day 1 to Day 2 post seeding. Both devices were fed gas 4 containing 19% $O_2$, 10% $CO_2$, and balance $N_2$. Ureagenesis was determined based on Method 2 of Example 6. Table 7 shows that by adjusting the number of cells seeded in each device, similar densities of cells were obtained. Further, the rate of synthesis of urea was approximately five times greater in the rat-scale device (with approximately five times as many cells) compared to the lab-scale device, such that the rate of ureagenesis per unit area was similar in the two devices.

TABLE 7

Scaling of Ureagenesis with Size of Cell Culturing Device

| Device Scale | Area (cm²) | Cells Seeded | | Ureagenesis | |
|---|---|---|---|---|---|
| | | Total | Density (cells/cm²) | (µg/day) | (µg/cm² – day) |
| Lab | 23 | $2.0 \times 10^6$ | $8.7 \times 10^4$ | 87 | 3.8 |
| Rat | 100 | $9.6 \times 10^7$ | $9.3 \times 10^4$ | 450 | 4.3 |

These results demonstrate that the invention allows linear scaling of hepatocellular function with size of the gas-permeable, liquid-impermeable membrane 30.

Figure 19:
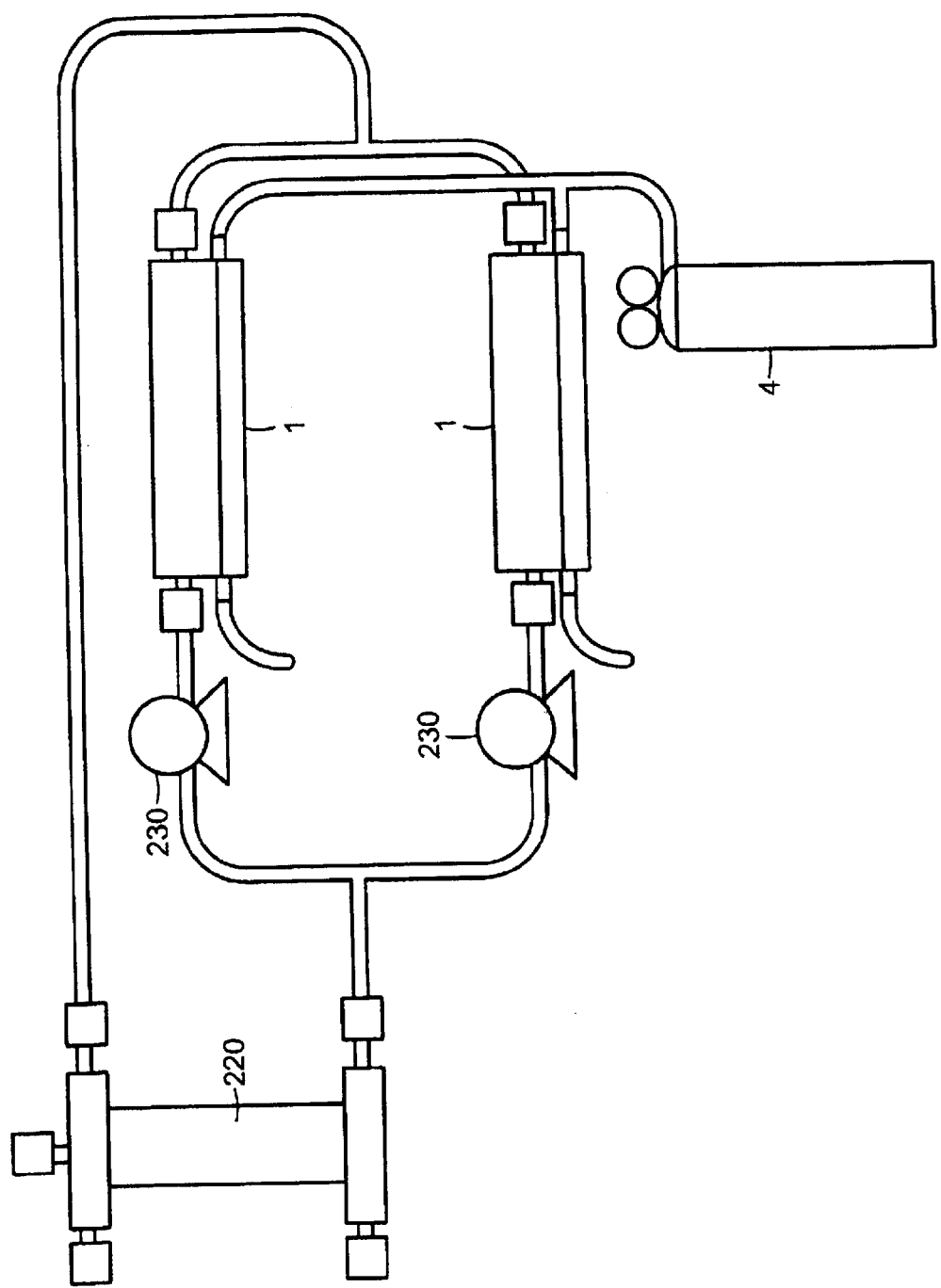
FIG. 19 is a schematic diagram of a pair of cell culture devices arranged in a parallel configuration in a single perfusion circuit.

The feasibility of scaling device size with a plurality of modular units was examined by comparing the performance of the apparatus of Example 2 with a modular system similar to this apparatus. FIG. 19 illustrates the configuration of such a modular system in which two devices 1 are placed in parallel in a single perfusion circuit. Pumps 230 drive both devices at the same volumetric flow rate from a single reservoir 220, such that both devices share the same volume of perfusate 11. Both devices are also fed the same gas 21 from the same source 4. With such a system the number of cells used to treat a perfusate can be increased without changing the density of cells in the system or the size of any individual unit.

For this study devices 1 were seeded with $8 \times 10^6$ hepatocytes 40 from donor 110, loaded as either single devices or paired parallel devices into perfusion circuits with 20 mL of complete medium as perfusate 11, and fed gas 4 containing 19% $O_2$, 10% $CO_2$, and balance $N_2$. Perfusion was conducted such that each device—whether as a singleton or paired in parallel—received 1.5 mL/min of complete medium with 20 mM exogenous ammonia from Day 1 to Day 2 at 1.5 mL/min. Ureagenesis was determined based on Method 2 of Example 6. Table 8 shows that doubling the number of cells seeded into the system with a pair of devices doubles the rate of ureagenesis for the system, such that the rate of ureagenesis per unit is constant. These results demonstrate that the overall function of the system scales linearly with the number of modular units in the system, such that increasing the size of the system through addition of devices operated in parallel increases the overall performance of the system.

TABLE 8

Scaling of Ureagenesis with Modularity of Cell Culturing Device

| Number Of Units | Total Area (cm$^2$) | Cells Seeded Total | Density (cells/cm$^2$) | Ureagenesis ($\mu$g/day) | ($\mu$g/unit/day) |
|---|---|---|---|---|---|
| Single | 23 | $8.0 \times 10^6$ | $3.5 \times 10^5$ | $9.5 \times 10^2$ | $9.5 \times 10^2$ |
| Pair in parallel | 46 | $1.6 \times 10^7$ | $3.5 \times 10^5$ | $2.1 \times 10^3$ | $1.0 \times 10^3$ |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for culturing hepatocytes, the method comprising:
   providing a gas-permeable, liquid-impermeable membrane having a first surface and a second surface;
   seeding hepatocytes on the first surface of the gas-permeable, liquid-impermeable membrane, wherein the hepatocytes are seeded directly on the membrane or directly on a molecularly-thick coating material on the surface of the membrane;
   contacting the hepatocytes directly with a nutrient-containing culture medium;
   providing an oxygenated fluid to the second surface of the gas-permeable, liquid-impermeable membrane at a pressure sufficient to provide transmembrane oxygenation to the hepatocytes seeded on the first surface; and
   culturing the hepatocytes under conditions that promote viability and function of the hepatocytes.

2. The method of claim 1, wherein the oxygen contained in the oxygenated fluid is at or above the critical partial pressure of oxygen.

3. The method of claim 1, wherein the hepatocytes are cultured in a device seeded with 2 to 20 billion hepatocytes.

4. The method of claim 1, wherein the hepatocytes are porcine, equine, ovine, bovine, rabbit, rat, canine, feline, or murine hepatocytes.

5. The method of claim 1, wherein the hepatocytes are human hepatocytes.

6. The method of claim 1, wherein the seeded hepatocytes are preserved hepatocytes.

7. The method of claim 6, wherein the preserved hepatocytes are cryopreserved, hypothermically stored, or lyophilized hepatocytes.

8. The method of claim 1, wherein the gas-permeable, liquid-impermeable membrane material is selected from the group consisting of polystyrene, polyolefin, polyethylene, polypropylene, polyvinylidene fluoride, polycarbonate, hydrophobic-treated nylon, polyurethane, polyester, layered styrene-butadiene-styrene/ethyl vinyl acetate/styrene-butadiene-styrene, and layered styrene-butadiene-styrene/polyethylene.

9. The method of claim 1, wherein the first surface of the gas-permeable, liquid-impermeable membrane is corona treated.

10. The method of claim 1, wherein the first surface of the gas-permeable, liquid-impermeable membrane is coated with a molecularly-thick coating of collagen.

11. The method of claim 1, wherein the concentration of oxygen in the oxygenated fluid is between about 0% to about 90% at a pressure of 2–5 psi.

12. The method of claim 11, wherein the concentration of oxygen in the oxygenated fluid is between about 19% to about 60% at a pressure of 2–5 psi.

13. The method of claim 11, wherein the concentration of oxygen in the oxygenated fluid is between about 40% to about 60% at a pressure of 2–5 psi.

14. The method of claim 1, wherein the concentration of oxygen in the oxygenated fluid is controlled to promote or downregulate cell function.

15. The method of claim 1, wherein the nutrient-containing culture medium is perfused.

16. The method of claim 1, wherein the nutrient-containing culture medium comprises blood plasma.

17. The method of claim 1, wherein the hepatocytes are seeded across the entire membrane from above the membrane.

18. The method of claim 1, wherein the hepatocytes are seeded directly onto the gas-permeable, liquid-impermeable membrane.

* * * * *